(12) United States Patent
Antoni et al.

(10) Patent No.: US 9,272,075 B2
(45) Date of Patent: Mar. 1, 2016

(54) COATING FOR SUBSTRATE

(71) Applicants: Per Antoni, Upplands Vasby (SE);
Daniel Nystrom, Upplands Vasby (SE);
Lars Vincent, Upplands Vasby (SE);
Krzysztof Pietrzak, Flagstaff, AZ (US)

(72) Inventors: Per Antoni, Upplands Vasby (SE);
Daniel Nystrom, Upplands Vasby (SE);
Lars Vincent, Upplands Vasby (SE);
Krzysztof Pietrzak, Flagstaff, AZ (US)

(73) Assignee: W.L. Gore & Associates, Inc., Newark, DE (US)

(*) Notice: Subject to any disclaimer, the term of this patent is extended or adjusted under 35 U.S.C. 154(b) by 0 days.

(21) Appl. No.: 14/172,342

(22) Filed: Feb. 4, 2014

(65) Prior Publication Data
US 2014/0221522 A1   Aug. 7, 2014

Related U.S. Application Data

(60) Provisional application No. 61/760,258, filed on Feb. 4, 2013.

(51) Int. Cl.
*A61L 31/10* (2006.01)
*A61L 31/16* (2006.01)
*A61L 27/34* (2006.01)
*A61L 27/54* (2006.01)
*A61L 29/08* (2006.01)
*A61L 29/16* (2006.01)

(52) U.S. Cl.
CPC ............ *A61L 31/10* (2013.01); *A61L 27/34* (2013.01); *A61L 27/54* (2013.01); *A61L 29/085* (2013.01); *A61L 29/16* (2013.01); *A61L 31/16* (2013.01); *A61L 2300/404* (2013.01); *A61L 2300/416* (2013.01); *A61L 2300/42* (2013.01); *A61L 2300/452* (2013.01); *A61L 2400/10* (2013.01); *A61L 2420/06* (2013.01)

(58) Field of Classification Search
CPC ...... A61L 27/34; A61L 31/10; A61L 33/0076
USPC .............................. 428/355 EN; 524/105, 107
See application file for complete search history.

(56) References Cited

U.S. PATENT DOCUMENTS

| | | | |
|---|---|---|---|
| 4,289,872 A | 9/1981 | Denkewalter et al. | |
| 4,613,665 A | 9/1986 | Larm | |
| 4,642,267 A | 2/1987 | Creasy et al. | |
| 5,229,490 A | 7/1993 | Tam | |
| 5,643,575 A | 7/1997 | Martinez et al. | |
| 5,932,462 A | 8/1999 | Harris et al. | |
| 6,461,311 B2 | 10/2002 | DuBois et al. | |
| 6,585,765 B1 | 7/2003 | Hossainy et al. | |
| 6,653,457 B1 | 11/2003 | Larm et al. | |
| 7,087,658 B2 | 8/2006 | Swan et al. | |
| 7,094,418 B2 | 8/2006 | Chudzik et al. | |
| 7,696,259 B2 | 4/2010 | Hanley et al. | |
| 2003/0135195 A1 | 7/2003 | Jimenez et al. | |
| 2003/0143596 A1 | 7/2003 | Bentley et al. | |
| 2006/0009550 A1 | 1/2006 | Messersmith et al. | |
| 2010/0189877 A1 | 7/2010 | Finley | |
| 2011/0046255 A1* | 2/2011 | Rooijmans | A61L 29/08 522/11 |
| 2012/0077049 A1* | 3/2012 | Lin | 428/520 |

FOREIGN PATENT DOCUMENTS

| | | |
|---|---|---|
| CN | 102000658 | 4/2011 |
| EP | 1063975 | 1/2001 |
| EP | 1131167 | 9/2001 |
| JP | 2010261001 | 11/2010 |
| KR | 20110128637 | 11/2011 |
| WO | 9321259 | 10/1993 |
| WO | 9621469 | 7/1996 |
| WO | 02060505 | 8/2002 |
| WO | 2004020012 | 3/2004 |
| WO | 2008049108 | 4/2008 |
| WO | 2008130604 | 10/2008 |
| WO | 2008133646 | 11/2008 |
| WO | 2009062146 | 5/2009 |
| WO | 2010006196 | 1/2010 |
| WO | 2011005258 | 1/2011 |
| WO | 2012047755 | 4/2012 |

OTHER PUBLICATIONS

Lee et al., "Mussel-inspired surface chemistry for multifunctional coatings", Science, 2007, 318, 426-430.

(Continued)

*Primary Examiner* — Tae H Yoon
(74) *Attorney, Agent, or Firm* — Klauber & Jackson LLC

(57) ABSTRACT

There is provided inter alia a substrate with a surface having a hydrophilic coating comprising a cross-linked copolymer of components A and B, and optional components C and D; wherein component A comprises one or more $C_2$-$C_{16}$ hydrophilic monomers each bearing one or more alkene and/or alkyne groups;

component B comprises one or more hydrophilic polymers each bearing two or more alkene and/or alkyne groups;

component C, if present, comprises one or more beneficial agents each bearing one or more alkene or alkyne groups; and component D, if present, comprises one or more low molecular weight cross-linking agents each bearing two or more functional groups independently selected from thiol, alkene and alkyne groups;

wherein the cross-linked copolymer is formed by radical polymerization involving the alkene and/or alkyne groups of components A, B and C (if present) and involving the functional groups of component D (if present);

wherein the hydrophilic coating optionally comprises component E which comprises one or more beneficial agents, wherein component E does not form a copolymer with components A, B, C (if present) and D (if present);

and wherein the hydrophilic coating is covalently attached to the surface of the substrate.

27 Claims, 6 Drawing Sheets

(56) References Cited

OTHER PUBLICATIONS

Lee, et al., Science, "Mussel-inspired Surface Chemistry for Multifunctional Coatings," 2007; 318: 426-430.

Yuan, et al., Langmuir, "Lysozyme-coupled Poly (poly(ethylene glycol)methyacrylate-Stainless Steel Hybrids and Their Antifouling and Antibacterial Surfaces," 2011; 27: 2761-2774.

Wei, et al., Polym. Chem., "Oxidant-induced dopamine polymerization for multifunctional coatings," 2010; 1: 1430-1433.

Kang, et al., Langmuir Letter, "Bio inspired Single Bacteria Cell Force Spectroscopy," 2009; 25: 9656-9659.

Dreyer, et al., Langmuir, "Elucidating the Structure of Poly(dopamine)," 2012; 28: 6428-6435.

United States Pharmacopeia (USP) Monograph 788, <788> Particulate Matter in Injections, 2008.

Ekdahl, et al., Advances in Experimental Medicine and Biology, "Chapter 18: Evaluation of Blood Compatibility of Materials, Cells, and Tissues: Basic Concepts, Test Models, and Practical Guidelines," 2013; 735: 257-270.

International Standard ISO 10993-5, "Biological evaluation of medical devices—Part 5: Tests for in vitro cytotoxicity," 2009.

Kang, et al., Angewandte Chemie, "Electrochemically Driven, Electrode-Addressable Formation of Functionalized Polydopamine Films for Neural Interfaces," 2012; 124: 13278-13281.

* cited by examiner

STRUCTURE A

STRUCTURE B

STRUCTURE C

STRUCTURE D

STRUCTURE E

COATING FOR SUBSTRATE

CROSS-REFERENCE TO RELATED APPLICATIONS

This application claims the priority of U.S. Provisional Application No. 61/760,258 filed on Feb. 4, 2013 which is incorporated by reference herein in its entirety.

FIELD OF THE INVENTION

The present invention relates to hydrophilic coatings for substrates such as medical devices, analytical devices, separation devices and other industrial articles including membranes and fabrics, and methods for preparing such coatings.

BACKGROUND OF THE INVENTION

Medical devices such as catheters, guide wires, retractable sheaths and stents commonly have surface coatings that are intended to increase the physical performance of the device and enhance longevity. Of particular interest are hydrophilic coatings which may also impart lubricity to the coated device.

Lubricity describes the property of "slipperiness" or "smoothness". Lubricious coatings are particularly useful for intracorporeal devices where their lubricity results in reduced frictional forces once a device is introduced and moved within the body, thereby enhancing patient comfort and reducing inflammation and tissue trauma. Lubricious coatings vary in composition but for use in an aqueous environment in vivo, such coatings are typically hydrophilic and wettable. As well as reducing friction, hydrophilic coatings also tend to be resistant to protein adhesion, therefore they have the potential to reduce or eliminate thrombosis. Examples of hydrophilic coating materials include coatings based on polyvinylpyrrolidone, poly(ethylene oxide) and polyurethane, as described in U.S. Pat. No. 4,642,267 and U.S. Pat. No. 6,461,311.

The manufacture of hydrophilic, lubricious coatings for use in vivo can present various difficulties. Such coatings are often prepared using organic solvents where residual traces of which must be removed to be below toxic limits according to current guidance and practice. Coated medical devices must also be able to withstand sterilisation procedures without the coating being chemically and/or physically altered or delaminated from the device.

One approach to forming a hydrophilic coating is to physically entrap functional hydrophilic polymers within a network of a supporting polymer that provides the necessary adherence to the surface of a substrate. These coatings are often referred to as interpenetrating networks (IPNs) and generally consist of a first functional polymer that imparts the desired properties to the coating (in this case hydrophilicity) and a supporting polymer that is chemically cross-linked in order to form a cross-linked polymer network. WO2008/130604 discloses an IPN formed by interspersing a hydrophilic polymer network such as polyethylene glycol with ionisable monomers such as acrylic acid, then polymerising the ionisable monomer to form the IPN, which when swollen with water is said to form coatings of high compressive strength and lubricity.

However, a disadvantage of having the hydrophilic polymer entrapped within an IPN rather than being chemically bonded to the coating is that the hydrophilic polymer may migrate out of the IPN over time. As such, the coating will gradually lose hydrophilicity. More significantly, however, the release of such particulates from the coatings of intracorporeal devices may pose a health risk for patients. Therefore, minimizing particulation is of importance for many medical devices. It should be noted that particulation is not just a concern for IPNs—all polymer coatings can potentially form particulates on the surface which can be released in vivo.

While the release in vivo of particulates/aggregates (known as particulation) from the surface of a coating may pose difficulties in the design and manufacture of the coating, removal of the coating itself via delamination or detachment from the substrate is also potentially a problem, both in terms of the health risks mentioned above and of the durability of the coating.

Considering durability, a coating can be removed from a substrate either by gradual erosion of the substance of the coating and/or by the coating being detached from surface of the substrate. Thus, one way to enhance the durability of a coating is to strengthen the binding between the coating and the surface of the substrate. This can be achieved, inter alia, by treating the surface to be coated with a primer in order to achieve better adhesion between the coating and the surface.

An ideal primer is one that can be universally applied to any substrate. In this regard, the use of polydopamine as a primer has attracted great interest since the discovery that simple immersion of a substrate in a dilute aqueous solution of dopamine, buffered to alkaline pH, results in the spontaneous deposition of a polydopamine film on the substrate. Messersmith et al. (Science, 2007, 318, 426-430) demonstrated that a polydopamine coating is able to form on virtually any type of substrate surface, including metals, metal oxides, ceramics, synthetic polymers and a wide range of other hydrophilic and hydrophobic materials. Polydopamine coatings have been used as a platform for the conjugation of synthetic polymers or biomolecules to a surface, as illustrated in WO2011/005258 which discloses the attachment of amine-functionalised polyethylene glycol ("PEG-NH$_2$") to a polydopamine coating, to provide a hydrophilic outer layer for the prevention of biofilm formation.

Coatings which are hydrophilic and preferably lubricious can be advantageously modified to include an agent having pharmacological activity, such as an anticoagulant, to impart further beneficial properties to the coating. US 2003/0135195 teaches a medical device such as a catheter with a highly lubricious hydrophilic coating formed from a mixture of colloidal aliphatic polyurethane polymer, an aqueous dilution of poly(1-vinylpyrrolidone-co-2-dimethylaminoethyl-methacrylate)-PVP and dendrimers. The document teaches that the coating can be applied to the device by dipping the device in a colloidal dispersion of the aliphatic polyurethane polymer in a solution of poly(1-vinylpyrrolidone-co-2-dimethylaminoethylmethacrylate)-PVP and an active agent (e.g. heparin) in a mixture of dendrimer, water, N-methyl-2-pyrrolidone and triethylamine. The document also teaches that heparin can be contained in the voids within the dendrimers, and that the loaded heparin will elute from the hydrophilic polymer matrix at a predetermined rate.

In summary, there remains a need for improved hydrophilic coatings for surfaces, particularly for the surfaces of devices that are inserted into the body. Preferably, such coatings are lubricious, durable, non-toxic, low particulating, sterilizable, biocompatible and readily applied to a surface.

SUMMARY OF THE INVENTION

In one aspect, the invention provides a substrate with a surface having a hydrophilic coating comprising a cross-linked copolymer of components A and B, and optional components C and D; wherein component A comprises one or more $C_2$-$C_{16}$ hydrophilic monomers each bearing one or more alkene and/or alkyne groups;

component B comprises one or more hydrophilic polymers each bearing two or more alkene and/or alkyne groups;

component C, if present, comprises one or more beneficial agents each bearing one or more alkene or alkyne groups; and component D, if present, comprises one or more low molecular weight cross-linking agents each bearing two or more functional groups independently selected from thiol, alkene and alkyne groups;

wherein the cross-linked copolymer is formed by radical polymerisation involving the alkene and/or alkyne groups of components A, B and C (if present) and involving the functional groups of component D (if present);

wherein the hydrophilic coating optionally comprises component E which comprises one or more beneficial agents, wherein component E does not form a copolymer with components A, B, C (if present) and D (if present);

and wherein the hydrophilic coating is covalently attached to the surface of the substrate.

As explained in the Examples, coatings of the present invention, in at least some embodiments, have been found to be highly lubricious and durable, while also being non-toxic, stable to sterilization and aging, biocompatible and low particulating, and are easily applied to the required surface of a substrate in a surface-independent manner.

DETAILED DESCRIPTION OF THE INVENTION

Substrate

Figure 1:
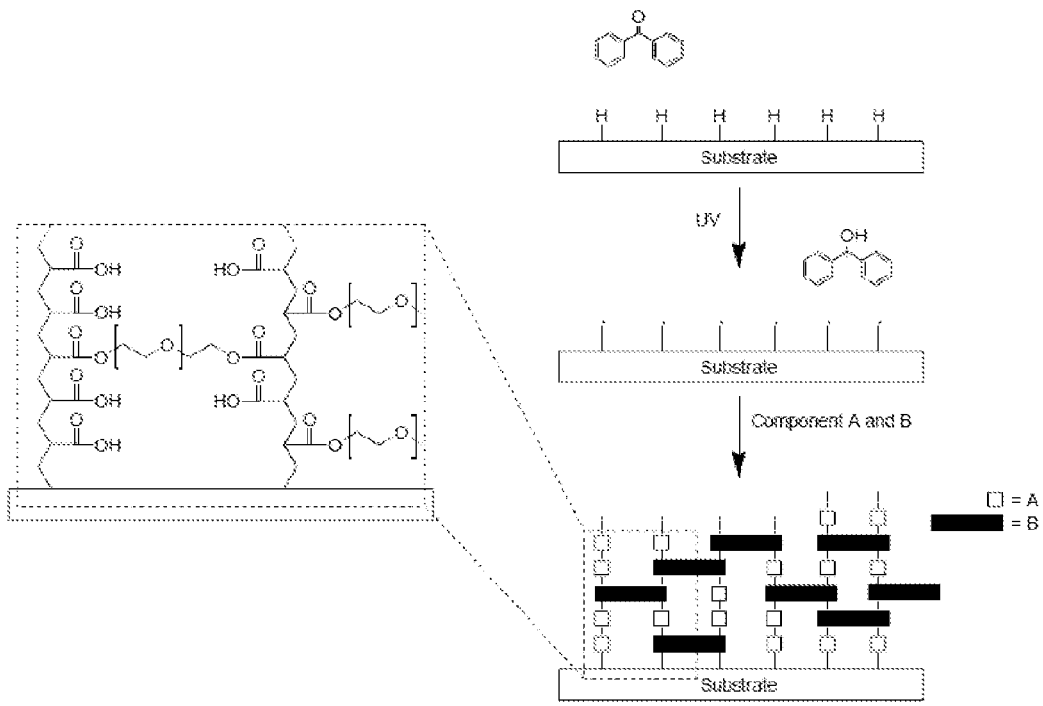
FIG. 1—shows an embodiment of the invention wherein covalent attachment between the surface of the substrate and the hydrophilic coating is formed via the reaction of surface-bound radicals on the surface of the substrate FIG. 2—shows an embodiment of the invention wherein radicals are formed in the liquid phase and polymerisation is initiated in the liquid phase and on the surface of the substrate, generating a covalently attached hydrophilic coating of components A and B.

Any substrate can potentially be coated with a hydrophilic coating of the invention, using the method of the invention, although such coatings are particularly useful for medical devices, analytical devices, separation devices, or other industrial articles including membranes and fabrics.

For the purposes of this patent application, the term "medical device" refers to intracorporeal or extra-corporeal devices but more usually to intracorporeal medical devices.

Thus, in one embodiment, the substrate is a medical device. In another embodiment, the substrate is an intracorporeal medical device. In a further embodiment, the substrate is an extracorporeal medical device.

Examples of intracorporeal medical devices which can be permanent or temporary intracorporeal medical devices include stents including bifurcated stents, balloon expandable stents, self-expanding stents, stent-grafts including bifurcated stent-grafts, grafts including vascular grafts, bifurcated grafts, dialators, vascular occluders, embolic filters, embolectomy devices, artificial blood vessels, blood indwelling monitoring devices, artificial heart valves, pacemaker electrodes, guidewires, cardiac leads, cardiopulmonary bypass circuits, cannulae, plugs, drug delivery devices, balloons, tissue patch devices, blood pumps, patches, cardiac leads, chronic infusion lines, arterial lines, devices for continuous subarachnoid infusions, feeding tubes, CNS shunts (e.g., a ventriculopleural shunt, a VA shunt, or a VP shunt), ventricular peritoneal shunts, ventricular atrial shunts, porto-systemic shunts and shunts for ascites.

Further examples of intracorporeal medical devices which can be permanent or temporary are catheters. Examples of catheters include, but are not limited to, central venous catheters, peripheral intravenous catheters, hemodialysis catheters, catheters such as coated catheters include implantable venous catheters, tunnelled venous catheters, coronary catheters useful for angiography, angioplasty, or ultrasound procedures in the heart or in peripheral veins and arteries, hepatic artery infusion catheters, CVC (central venous catheters), peripheral intravenous catheters, peripherally inserted central venous catheters (PIC lines), flow-directed balloon-tipped pulmonary artery catheters, total parenteral nutrition catheters, chronic dwelling catheters (e.g., chronic dwelling gastrointestinal catheters and chronic dwelling genitourinary catheters), peritoneal dialysis catheters, CPB catheters (cardiopulmonary bypass), urinary catheters and microcatheters (e.g. for intracranial application).

Medical devices include endovascular device delivery systems such as stents, occluders, valves, etc. diagnostics catheters containing spectroscopic or imaging capabilities, placement wires, catheters or sheaths.

In a specific embodiment, the substrate is a medical device selected from the group consisting of stents including bifurcated stents, balloon expandable stents and self-expanding stents, stent-grafts including bifurcated stent-grafts, grafts including vascular grafts and bifurcated grafts, dialators, vascular occluders, embolic filters, embolectomy devices, catheters including microcatheters, central venous catheters, peripheral intravenous catheters and hemodialysis catheters, artificial blood vessels, sheaths including retractable sheaths, blood indwelling monitoring devices, artificial heart valves, pacemaker electrodes, guidewires, cardiac leads, cardiopulmonary bypass circuits, cannulae, plugs, drug delivery devices, balloons, tissue patch devices and blood pumps.

Examples of extracorporeal medical devices are non-implantable devices such as extracorporeal blood treatment devices, and transfusion devices. Devices may have neurological, peripheral, cardiac, orthopedal, dermal and gynecological application, inter alia.

In another embodiment, the above-mentioned stents can be used in cardiac, peripheral or neurological applications. In another embodiment, said stent-grafts can be used in cardiac, peripheral or neurological applications.

In another embodiment, the above-mentioned sheaths can be an interventional diagnostic and therapeutic sheath, large and standard bore endovascular delivery sheaths, arterial introducer sheaths with and without hemostatic control and with or without steering, micro-introducer sheaths, dialysis access sheaths, guiding sheaths, and percutaneous sheaths; all for access in carotid, renal, transradial, transseptal, pediatric and micro applications.

In another embodiment, said medical device can be used in neurological, peripheral, cardiac, orthopedic, dermal, or gynecologic applications.

An analytical device can be, for example, a solid support for carrying out an analytical process such as chromatography or an immunological assay, reactive chemistry or catalysis. Examples of such devices include slides, beads, well plates and membranes. A separation device can be, for example, a solid support for carrying out a separation process such as protein purification, affinity chromatography or ion exchange. Examples of such devices include filters and columns.

The surface to be coated can be the entire surface of the substrate, or only a portion of the surface of the substrate. Certain substrates may have an external surface and an internal surface, either or both of which can be coated. For example, tubular substrates such as artificial blood vessels have an internal surface, or lumen, which can be coated independently from the external surface. A surface comprising an internal and an external surface may only require the internal surface to the coated. Conversely, only the external surface may require the coating. Using the method of the invention, it is possible to apply a different coating to e.g. the external and internal surfaces of the substrate.

In one embodiment, up to 99%, for example up to 95%, 90%, 75%, 50% or 25% of the surface of the substrate is coated with the hydrophilic coating. In one embodiment, both the external and internal surfaces of the substrate are coated. In another embodiment, only the external surface of the substrate is coated. In one embodiment, the substrate to be coated is tubular in shape having an internal surface or lumen, which can be coated independently from the external surface. The surface of the substrate can be porous or non-porous.

In another embodiment, portions of the surface of the substrate may be selectively coated by tuning the composition of the surface of the substrate e.g. a surface of a substrate comprising abstractable hydrogens may be coated whereas parts of the surface of the substrate that do not contain abstractable hydrogen atoms will not be coated with a hydrophilic coating within this invention.

Substrate Materials Useful within this Invention

The substrate may comprise or be formed of a metal or a synthetic or naturally occurring organic or inorganic polymer or a ceramic material, inter alia.

Thus, for example, it can be formed from a synthetic or naturally occurring organic or inorganic polymer or material such as polyolefins, polyesters, polyurethanes, polyamides, polyether block amides, polyimides, polycarbonates, polyphenylene sulfides, polyphenylene oxides, polyethers, silicones, polycarbonates, polyhydroxyethylmethacrylate, polyvinyl pyrrolidone, polyvinyl alcohol, rubber, silicone rubber, polyhydroxyacids, polyallylamine, polyallylalcohol, polyacrylamide, and polyacrylic acid, styrenic polymers, polytetrafluoroethylene and copolymers thereof, derivatives thereof and mixtures thereof. Some of these classes are available both as thermosets and as thermoplastic polymers. As used herein, the term "copolymer" shall be used to refer to any polymer formed from two or more monomers, e.g. 2, 3, 4, 5 and so on and so forth. Bioresorbables, such as poly(D,L-lactide) and polyglycolids and copolymers thereof are also useful. Useful polyamides include, but are not limited to, nylon 12, nylon 11, nylon 9, nylon 6/9 and nylon 6/6. Examples of some copolymers of such materials include the polyether-block-amides, available from Elf Atochem North America in Philadelphia, Pa. under the tradename of PEBAX®. Another suitable copolymer is a polyetheresteramide. Suitable polyester copolymers, include, for example, polyethylene terephthalate and polybutylene terephthalate, polyester ethers and polyester elastomer copolymers such as those available from DuPont in Wilmington, Del. under the tradename of HYTREL®. Block copolymer elastomers such as those copolymers having styrene end blocks, and midblocks formed from butadiene, isoprene, ethylene/butylene, ethylene/propene, and so forth may be employed herein. Other styrenic block copolymers include acrylonitrile-styrene and acrylonitrile-butadiene-styrene block copolymers. Also, block copolymers wherein the particular block copolymer thermoplastic elastomers in which the block copolymer is made up of hard segments of a polyester or polyamide and soft segments of polyether may also be employed herein. Other useful substrates are polystyrenes, poly(methyl)methacrylates, polyacrylonitriles, poly(vinylacetates), poly(vinyl alcohols), chlorine-containing polymers such as poly(vinyl) chloride, polyoxymethylenes, polycarbonates, polyamides, polyimides, polyurethanes, phenolics, amino-epoxy resins, polyesters, silicones, cellulose-based plastics, and rubber-like plastics.

Combinations of these materials can be employed with and without cross-linking.

Polymeric substrates may optionally be blended with fillers and/or colorants.

In one embodiment, said biocompatible substrate is a polyether-block-amides, such as PEBAX®.

Fluorinated polymers such as fluoropolymers, e.g expanded polytetrafluoroethylene (ePTFE), polytetrafluoroethylene (PTFE), fluorinated ethylene-propylene (FEP), perfluorocarbon copolymers, e.g. tetrafluoroethylene perfluoroalkylvinyl ether (TFE/PAVE) copolymers, copolymers of tetrafluoroethylene (TFE) and perfluoromethyl vinyl ether (PMVE), and combinations of the above with and without crosslinking between the polymer chains, expanded polyethylene, polyvinylchloride, polyurethane, silicone, polyethylene, polypropylene, polyurethane, polyglycolic acid, polyesters, polyamides, elastomers and their mixtures, blends and copolymers or derivatives thereof may be useful.

Other suitable substrates include proteins, such as silk and wool, agarose and alginate. Also, certain metals and ceramics may be used as substrates for the present invention. Suitable metals include, but are not limited to, biocompatible metals, titanium, stainless steel, high nitrogen stainless steel, gold, silver, rhodium, zinc, platinum, rubidium, copper and magnesium, and combinations thereof. Suitable alloys include cobalt-chromium alloys such as L-605, MP35N, Elgiloy, nickel-titanium alloys (such as Nitinol), tantalum, and niobium alloys, such as Nb-1% Zr, and others. Ceramic substrates may include, but are not limited to, silicone oxides, aluminum oxides, alumina, silica, hydroxyapapitites, glasses, calcium oxides, polysilanols, and phosphorous oxide.

In one embodiment, said biocompatible metal is a nickel-titanium alloy, such as Nitinol.

Hydrophilic Coating

The hydrophilic coating of the invention comprises components A and B, and optional components C, D and E, as described below.

Component A

Component A comprises and suitably consists of one or more $C_2$-$C_{16}$ hydrophilic monomers each bearing one or more alkene and/or alkyne groups. The alkene and/or alkyne groups of component A take part in the radical polymerisation reaction to form the copolymer. Suitably component A comprises and more suitably consists of one or more $C_2$-$C_{16}$ hydrophilic monomers each bearing one or more alkene groups.

It should be noted that the carbon atoms within the alkene and/or alkyne groups are to be included within the $C_2$-$C_{16}$ limitation. The term "hydrophilic monomer" is well known to a person skilled in the art and broadly encompasses monomers which have an affinity for water and tend to be soluble in aqueous and polar solvents. Polar solvents include but are not limited to, alcohols (such as methanol, ethanol, propanol, isopropanol), tetrahydrofuran, DMF, DMSO, EtOAc and dioxane, and aqueous solutions of all of the aforementioned solvents.

In one embodiment, component A comprises and suitably consists of one or more $C_2$-$C_{16}$ hydrophilic monomers each bearing one alkene or one alkyne group. In another embodiment, component A comprises and suitably consists of one or more $C_2$-$C_{16}$ hydrophilic monomers each bearing one alkene group. The alkene and/or alkyne groups can be terminal or non-terminal groups.

Component A typically serves the role of a structural monomer which will polymerise to form a polymer with good structural stability and durability. Thus, the higher the proportion of component A in the copolymer of components A, B and optionally C and/or D, the more durable the copolymer may be expected to be. However, if the proportion of component A is too high, the resulting copolymer and coating can lose flexibility.

The hydrophilic character of the monomer may derive from the functional groups (other than the alkene or alkyne) that it possesses. Such functional groups can be in a terminal or pendant position, or form a linkage within the molecule. As used herein, the term "hydrophilic monomer bearing a functional group" should be taken to mean a hydrophilic monomer comprising a functional group which can be integral to the monomer (i.e. a linker within the monomer) and/or a pendant or terminal functional group. Thus, in one embodiment component A comprises and suitably consists of one or more $C_2$-$C_{16}$ hydrophilic monomers each bearing one or more alkene and/or alkyne groups, and also one or more groups selected from ester, ether, carboxyl, hydroxyl, thiol, sulfonic acid, sulfate, amino, amido, phosphate, keto and aldehyde groups. It should be noted that as well as the alkene and/or alkyne groups, the additional groups are also to be included within the $C_2$-$C_{16}$ limitation. Functional groups can be neutral or charged. For example, an amino group can be neutral or can be protonated or otherwise substituted to form a quaternary ammonium compound. Likewise, carboxyl groups and phosphate groups can be present in deprotonated form and thus be negatively changed. Zwitterionic hydrophilic monomers such as zwitterionic hydrophilic monomers carrying betaine or phoshorylcholine moieties are also contemplated. In another embodiment, component A comprises and suitably consists of one or more $C_2$-$C_{16}$ hydrophilic monomers each bearing one or more alkene and/or alkyne groups, and also one or more carboxyl groups. In a further embodiment, component A comprises and suitably consists of one or more $C_2$-$C_{16}$ hydrophilic monomers each bearing one alkene group and one carboxyl group.

Hydrophilic monomers can be straight chain, cyclic or branched. In one embodiment, component A comprises and suitably consists of one or more $C_2$-$C_{16}$, $C_2$-$C_{15}$, $C_2$-$C_{14}$, $C_2$-$C_{13}$, $C_2$-$C_{12}$, $C_2$-$C_{11}$, $C_2$-$C_{10}$, $C_2$-$C_9$, $C_2$-$C_8$, $C_2$-$C_7$, $C_2$-$C_6$, $C_2$-$C_5$, $C_2$-$C_4$, $C_2$-$C_3$, $C_3$-$C_{16}$, $C_3$-$C_{15}$, $C_3$-$C_{14}$, $C_3$-$C_{13}$, $C_3$-$C_{12}$, $C_3$-$C_{11}$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$ or $C_{16}$ hydrophilic monomers each bearing one or more alkene and/or alkyne groups. In one embodiment, the hydrophilic monomers of component A each bear one or more alkene groups. In another embodiment, the hydrophilic monomers of component A each bear one or more alkyne groups. Preferably the hydrophilic monomers of component A bear alkene groups.

In one embodiment, component A comprises and suitably consists of one or more $C_2$-$C_{16}$ hydrophilic monomers each bearing one or more alkene and or alkyne groups, wherein said one or more hydrophilic monomers have Mw of 40-500 Da, for example 40-100 Da, 40-90 Da or 70-90 Da.

Suitably, component A contains a single alkene or alkyne group and will therefore not form cross-linkages within the copolymer of components A, B and optionally C and/or D.

In an embodiment, component A comprises a carboxylate group.

Specific examples of component A include but are not limited to acrylic acid, methacrylic acid, vinyl alcohol, allyl alcohol, vinyl amine, allyl amine, polyethyleneglycol acrylate, oligoetyleneglycol acrylate, 2-hydroxyethyl methacrylate (HEMA), acrylamide, methacrylamide, N-vinylpyrrolidone, glycidyl acrylate, glycidyl methacrylate, 4-styrene sulfonate. In one embodiment, component A is acrylic acid. In another embodiment, component A is methacrylic acid. In a further embodiment, component A comprises and suitably consists of acrylic acid and/or methacrylic acid.

Examples of $C_2$-$C_9$ hydrophilic monomers are shown below. Also useful within this invention are salts of below charged hydrophilic monomers.

Examples of $C_2$ hydrophilic monomers

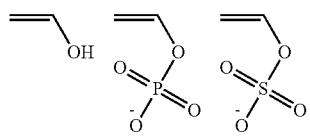

Examples of $C_3$ hydrophilic monomers

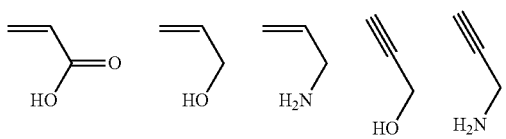

Examples of $C_4$ hydrophilic monomers

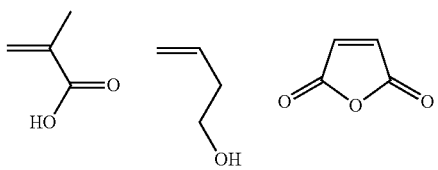

Examples of C₅ hydrophilic monomers

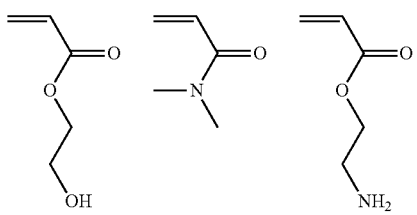

Examples of C₆ hydrophilic monomers

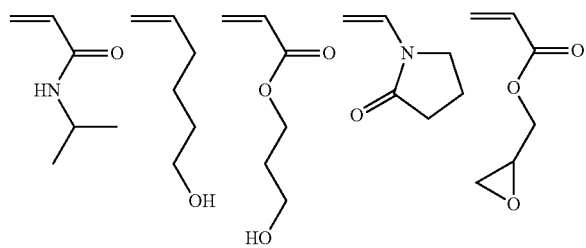

Examples of C₇ hydrophilic monomers

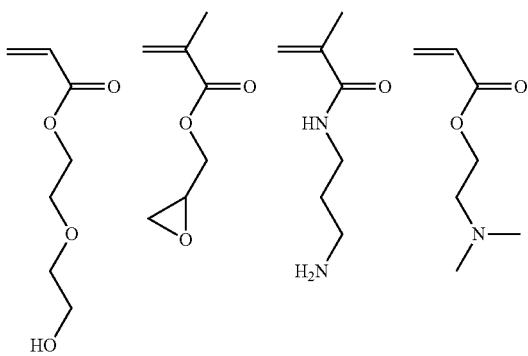

Examples of C₈ hydrophilic monomers

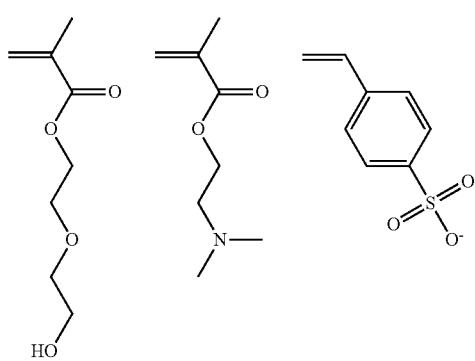

Examples of C₉ hydrophilic monomers

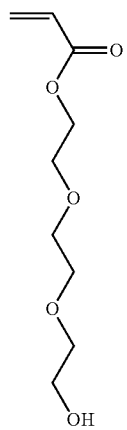

Component B

Component B comprises and suitably consists of one or more hydrophilic polymers each bearing two or more alkene and/or alkyne groups. The alkene and/or alkyne groups of component B take part in the radical polymerisation reaction to form the copolymer. In an embodiment, component B comprises and suitably consists of one or more hydrophilic polymers each bearing two or more alkene groups.

The term "hydrophilic polymer" is well known to a person skilled in the art and broadly encompasses polymers which have an affinity for water and tend to be soluble in aqueous and polar solvents. Polar solvents include, but are not limited to, alcohols (such as methanol, ethanol, propanol, isopropanol), tetrahydrofuran, DMF, DMSO, EtOAc and dioxane, and aqueous solutions of all of the aforementioned solvents.

Component B has hydrophilic character and typically will confer lubricity to the copolymer of components A, B and optionally C and/or D. Thus, the higher the proportion of component B in the copolymer of components A, B and optionally C and/or D, the more lubricious the coating may be expected to be.

In one embodiment, component B comprises and suitably consists of one or more hydrophilic polymers each bearing two alkene and/or alkyne groups. In another embodiment, component B comprises and suitably consists of one or more hydrophilic polymers each bearing two alkene groups.

In one embodiment, component B comprises and suitably consists of one or more hydrophilic polymers each bearing two or more alkene and/or alkyne groups, wherein said alkene and/or alkyne groups are terminal alkene and/or alkyne groups. It should be noted that component B may independently bear alkene or alkyne groups and can be both alkene- and alkyne-functionalised. Thus, a hydrophilic polymer "bearing two or more alkene and/or alkyne groups" is intended to cover a hydrophilic polymer with one alkene and one alkyne group.

Hydrophilic polymers each bearing two or more alkene and/or alkyne groups can be formed by functionalising a pre-formed hydrophilic polymer with alkene or alkyne groups. Such a pre-formed polymer must have suitable reactive groups, for example hydroxyl, amino, thiol, azide, oxirane, alkoxyamine and/or carboxyl groups. Such reactive groups can be at the ends of the hydrophilic polymer, along the backbone of the hydrophilic polymer, or in both positions. The pre-formed polymer with reactive groups may then be reacted with an alkene or alkyne functionalised reagent with a complementary reactive group such as a carboxylic acid, activated ester or acid chloride, amine or alcohol.

In one embodiment, component B comprises and suitably consists of one or more hydrophilic polymers each bearing two or more alkene and/or alkyne groups, wherein the hydrophilic polymer is independently selected from the group consisting of hyaluronic acid, a hyaluronic acid derivative, poly-N-vinylpyrrolidone, a poly-N-vinylpyrrolidone derivative, polyethylene oxide, a polyethylene oxide derivative, a polyalkylene glycol, a polyether derivative (e.g. polyethylene glycol (PEG), a polyethylene glycol (PEG) derivative, polypropylene glycol (PPG) or a polypropylene glycol (PPG) derivative), polyglycidol, polyvinylalcohol, a polyvinylalcohol derivative, polyacrylic acid, a polyacrylic acid derivative, silicone, a silicone derivative, polysaccharide, a polysaccharide derivative, polysulfobetaine, a polysulfobetaine derivative, polycarboxybetaine, a polycarboxybetaine derivative, a polyalcohol such as polyHEMA, a polyacid such as an alginate, dextran, agarose, poly-lysine, polymethacrylic acid, a polymethacrylic acid derivative, polymethacrylamide, a polymethacrylamide derivative, a polyacrylamide, polyacrylamide derivative, polysulfone, a polysulfone derivative, sulfonated polystyrene, a sulfonated polystyrene derivative, polyallylamine, a polyallylamine derivative, polyethyleneimine, a polyethyleneimine derivative, polyoxazoline, a polyoxazoline derivative, polyamine and a polyamine derivative. Block polymers of above mentioned polymers are also useful; e.g. poly(vinyl alcohol-co-ethylene), poly(ethyleneglycol-co-propyleneglycol), poly(vinyl acetate-co-vinyl alcohol), poly(tetrafluoroethylene-co-vinyl alcohol), poly(acrylonitrile-co-acrylamide), poly(acrylonitrile-co-acrylic acid-co-acrylamidine).

In another embodiment, component B comprises and suitably consists of one or more hydrophilic polymers each bearing two or more alkene and/or alkyne groups, wherein the hydrophilic polymer is independently selected from the group consisting of hyaluronic acid, a hyaluronic acid derivative, poly-N-vinylpyrrolidone, a poly-N-vinylpyrrolidone derivative, a polyether derivative (e.g. polyethylene glycol (PEG), a polyethylene glycol (PEG) derivative, polypropylene glycol (PPG) or a polypropylene glycol (PPG) derivative, polyvinylalcohol, and a polyvinylalcohol derivative.

Where the hydrophilic polymer is referred to as being a derivative, for example "a polyamine derivative", this is not intended to include the alkene or alkyne derivatisation—this refers to additional derivatisation. Thus, "a polyamine derivative" may include a polyamine functionalised with e.g. thiol, hydroxyl or azide groups, which may then be modified to bear alkene and/or alkyne groups.

In a further embodiment, component B comprises and suitably consists of one or more hydrophilic polymers each bearing two or more alkene and/or alkyne groups, wherein the hydrophilic polymer is independently selected from the group consisting of polyethylene glycol (PEG), a polyethylene glycol (PEG) derivative, polypropylene glycol (PPG) and a polypropylene glycol (PPG) derivative). Copolymers thereof (e.g. copolymers of ethylene glycol and propylene glycol), terpolymers thereof, and mixtures thereof, are also contemplated.

In one embodiment, component B comprises and suitably consists of one or more hydrophilic polymers each bearing two alkene groups. In another embodiment, component B comprises and suitably consists of one or more polyether hydrophilic polymers (e.g. polyethylene glycol (PEG), a polyethylene glycol (PEG) derivative, polypropylene glycol (PPG) or a polypropylene glycol (PPG) derivative) each bearing two or more alkene and/or alkyne groups. In a preferred embodiment, component B comprises and suitably consists of one or more PEG polymers each bearing two alkene groups. In another embodiment, component B comprises and suitably consists of one or more hydrophilic polymers each bearing two or more alkene and/or alkyne groups, wherein said alkene and/or alkyne groups are terminal alkene and/or alkyne groups.

When component B comprises and suitably consists of a polyether hydrophilic polymer, the polymer will generally be alkene and/or alkyne-functionalised via its end groups. Polyether polymers most often terminate with a hydroxyl group, however other end groups include but are not limited to amino and thiol. Any of these groups can be functionalised with the required alkene and/or alkyne functionality. Suitable reagents for introducing alkene functionality include alkene-functionalised reagents including a leaving group (e.g. halogen), alkene-functionalised carboxylic acids, acid chlorides and activated esters, or acrylate compounds. Suitable reagents for introducing alkyne functionality include alkyne-functionalised reagents including a leaving group (e.g. halogen), alkyne-functionalised carboxylic acids, acid chlorides and activated esters. Thus, the polyether polymer can be independently alkene or alkyne-functionalised via at least two linkages which include, but not limited to: ether, thioether, amine, ester, thioester, amide and carbamate linkages. By varying the linkage used in component B, the nature of the resulting copolymer can be varied. Component B can be either biodegradable or biostable.

The skilled person will appreciate that technical grades of di-functional polymers (such as dihydroxyl PEG) may contain small amounts of the corresponding mono-functional (e.g. mono-hydroxyl) polymer, which when functionalised with alkene or alkyne groups will form a mono-alkene or alkyne functionalised polymer. Thus, although component B is defined as consisting of one or more hydrophilic polymers each bearing two or more alkene and/or alkyne groups, a small (functionally insignificant) amount of mono alkene or alkyne functionalised hydrophilic polymer will be tolerated, and is encompassed within the definition of component B.

In one embodiment, component B comprises and suitably consists of one or more polyethylene glycol (PEG) polymers, each bearing two or more alkene and/or alkyne groups. Preferably, each PEG polymer bears two alkene groups. PEG is a polyether compound, which in linear form has general formula $H[O-CH_2-CH_2]_n-OH$. Branched versions, including hyperbranched and dendritic versions are also contemplated and are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly (ethylene glycol) can be represented in general form as $R(-PEG-OH)_m$ in which R is derived from a core moiety, such as glycerol, glycerol oligomers, or pentaerythritol, and m represents the number of arms. Multi-armed PEG molecules, such as those described in U.S. Pat. No. 5,932,462; U.S. Pat. No. 5,643,575; U.S. Pat. No. 5,229,490; U.S. Pat. No. 4,289,872; US 2003/0143596; WO 96/21469; and WO 93/21259 may also be used.

When component B comprises and suitably consists of one or more polyethylene glycol (PEG) polymers, each bearing two or more alkene and/or alkyne groups, suitably the PEG polymers are diacrylate-functionalised PEG polymers.

In one embodiment, the one or more diacrylate-functionalised PEG polymers are of formula (I):

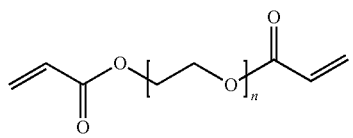

(I)

wherein n is 10-50,000 e.g. 15-5,000 e.g. 100-400, suitably 150-260.

In another embodiment, the one or more diacrylate-functionalised PEG polymers are of formula (II):

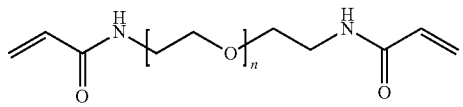

(II)

wherein n is 10-50,000 e.g. 15-5,000 e.g. 100-400, suitably 150-260.

When component B comprises and suitably consists of one or more PEG polymers each bearing two or more alkene or alkyne groups, the PEG polymers have an average molecular weight of, for example, 600-2,000,000 Da, 60,000-2,000,000 Da, 40,000-2,000,000 Da, 400,000-1,600,000 Da, 800-1,200,000 Da, 600-40,000 Da, 600-20,000 Da, 4,000-16,000 Da, or 8,000-12,000 Da.

In one embodiment, component B comprises and suitably consists of one or more hydrophilic polymers each bearing two or more alkene and/or alkyne groups, wherein each hydrophilic polymer independently has molecular weight of 600-40,000 Da, 600-20,000 Da, 4,000-16,000 Da, or 8,000-12,000 Da.

Component B may consist of two or more (e.g. two) different hydrophilic polymers each bearing two or more alkene and/or alkyne groups. For example, component B may consist of two different polyether polymers, each having a different molecular weight. Thus, in one embodiment, component B comprises and suitably consists of two different hydrophilic polymers each bearing two or more alkene and/or alkyne groups. In another embodiment, component B comprises and suitably consists of two different polyether polymers each bearing two or more alkene and/or alkyne groups. In a further embodiment, component B comprises and suitably consists of two different molecular weight PEG polymers each bearing two or more alkene and/or alkyne groups. In one embodiment, component B comprises and suitably consists of a first PEG polymer bearing two alkene groups having an average molecular weight of 600-40,000 Da, 600-20,000 Da, 4,000-16,000 Da, or 8,000-12,000 Da and a second PEG polymer bearing two alkene groups, said second PEG polymer having an average molecular weight of 60,000-2,000,000 Da, 40,000-2,000,000 Da, 400,000-1,600,000 Da or 800,000-1,200,000 Da.

Suitably, the second, higher average molecular weight PEG polymer will be present in a lower weight percentage (wt. %) that the first, lower average molecular weight PEG polymer. For example, when component B comprises and suitably consists of two different molecular weight PEG polymers, at least 99% (by weight) of component B will be lower average molecular weight polymer, for example at least 98%, 97%, 96%, 95%, 94%, 93%, 92%, 91%, 90%, 85% or 80% (by weight). The addition of the significantly higher molecular weight PEG polymer tends to have the effect of increasing the lubricity of the final hydrophilic coating. However, if the proportion of higher molecular weight PEG polymer is too great, the amount of crosslinking within the copolymer of components A, B and optionally C and/or D is reduced, which may impact on the durability of the hydrophilic coating.

Component C

Component C is an optional component in the hydrophilic coating of the invention. If present, component C comprises and suitably consists of one or more beneficial agents each bearing one or more alkene or alkyne groups (suitably one alkene or alkyne group). The alkene or alkyne group of component C takes part in the radical polymerisation reaction to form the copolymer.

The term "beneficial agent" includes any agent which imparts a particular desired effect when comprised in the hydrophilic coating of the invention. Examples of beneficial agents include an agent having pharmacological activity, a conductive agent, a lubricious agent or an adhesive agent. For example, the beneficial agents may be an agent having pharmacological activity, a conductive agent or an adhesive agent.

"An agent having pharmacological activity" as used herein, which is used interchangeable with the term "drug", is an agent that induces a bio-response.

Examples of agents having pharmacological activity include, but are not limited to, anti-thrombogenic agents, hemostatic agents, anti-angiogenic agents, angiogenic agents, anti-microbial agents, anti-proliferative agents, proliferative agents and anti-inflammatory agents.

Agents Having Pharmacological Activity

Anti-Thrombogenic Agents

Anti-thrombogenic agents may be used to prevent or alleviate the serious adverse effect of coagulation of the blood which can result when inserting a medical device into the body. Examples of anti-thrombogenic agents include heparin, heparin derivatives, hirudin, eptifibatide, tirofibran, urokinase, D-Phe-Pro-Arg chloromethylketone, an RGD peptide-containing compound, AZX100 a cell peptide that mimics HSP20 (Capstone Therapeutics Corp., USA), thrombin inhibitors, platelet receptor antagonists, anti-thrombin antibodies, anti-platelet receptor antibodies, aspirin, prostaglandin inhibitors, platelet inhibitors (clopidogrel and abciximab) and antiplatelet peptides, coumadins (vitamin K antagonists of the 4-hydroxycoumarin class like warfarin), argatroban, thrombomodulin and anti-coagulant proteins. Anti-thrombogenic agents may also include enzymes such as apyrase. Such substances may be charged (e.g. anionic) or uncharged. Other examples are glycosaminoglycans, dermatan disulfate, dermatan disulfate analogs, and derivatives thereof.

The term "heparin" refers to a heparin molecule, a fragment of a heparin molecule or a heparin derivative. Heparin derivatives can be any functional or structural variation of heparin. Representative variations include alkali metal or alkaline earth metal salts of heparin, such as sodium heparin (e.g. Hepsal or Pularin), potassium heparin (e.g. Clarin), lithium heparin, calcium heparin (e.g. Calciparine), magnesium heparin (e.g. Cutheparine), and low molecular weight heparin (prepared by e.g. oxidative depolymerization or deaminative cleavage, e.g. Ardeparin sodium or Dalteparin). Other examples include heparan sulfate, heparinoids, heparin based compounds and heparin having a hydrophobic counter-ion. Other desirable anti-coagulant entities include synthetic heparin compositions referred to as "fondaparinux" compositions (e.g. Arixtra from GlaxoSmithKline) involving anti-thrombin-mediated inhibition of factor Xa. Additional derivatives of heparin include heparins and heparin moieties modified by means of e.g. mild nitrous acid degradation (U.S. Pat. No. 4,613,665) or periodate oxidation (U.S. Pat. No.

6,653,457) and other modification reactions known in the art where the bioactivity of the heparin moiety is essentially preserved.

Hemostatic Agents

Hemostatic agents may be used to stop the bleeding, hemorrhage, or blood flow through a blood vessel or body part to prevent massive blood loss. They may cause the aggregation of platelets and the formation of clots and are used to arrest bleeding in surgical procedures.

Examples of hemostatic agents are fibrin sealants, absorbable hemostatic agents with and without thrombin, solutions of thrombin, collagen, microfibrillar collagen, gelatin, gelatin sponges, regenerated oxidized cellulose, bone wax, glucosamine containing polymers, chitosan, plant extracts, minerals, rFVIIa and anti-fibrinolytics.

Anti-Angiogenic Agents

Anti-angiogenetic agents block tumor angiogenesis and target vascular endothelial cells. Examples of anti-angiogenetic agents are sunitinib, bevacizumab, itraconazole, suramin, and tetrathiomolybdate.

Angiogenic Agents

Angiogenic agents can be used in applications where cell growth is desired. Examples of angiogenic agents include growth factors and RGD protein.

Anti-Microbial Agents

Anti-microbial agent is a general term for drugs, chemicals, or other substances that either kill or slow the growth of microbes. Among the anti-microbial agents are antibacterial drugs, antiviral agents, antifungal agents, and antiparisitic drugs. Examples of anti-microbial agents include compounds selected from the group consisting of diamidines, iodine and iodophors, peroxygens, phenols, bisphenols, halophenols, biguanides, silver compounds, triclosan, chlorhexidine, triclocarban, hexachlorophene, dibromopropamidine, chloroxylenol, phenol and cresol or combinations thereof and salts and combinations thereof an antibiotic, erythromycin orvancomycin; dopamine, bromocriptine mesylate, pergolide mesylate or another dopamine agonist; or another radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, nitrofurazone, benzalkonium chloride, antibiotics such as rifampin, gentamycin cephalosporins, aminoglycosides, nitrofurantoin and minocycline, salicylic acid, alphatocopherol, superoxide dismutase, deferoxyamine, a 21-aminosteroid (lasaroid) or another free radical scavenger, iron chelator or antioxidant; angiopeptin; a 14C-, 3H-, 131I-, 32P or 36S-radiolabelled form or other radiolabelled form of any of the foregoing; or a mixture of any of these. Other examples are cytotoxic agents, cytostatic agents and cell proliferation affectors; vasodilating agents; agents that interfere with endogenous vasoactive mechanisms; inhibitors of leukocyte recruitment, such as monoclonal antibodies; cytokines; hormones or a combination thereof.

Proliferative Agents

Proliferative agents stimulate cell growth and examples are vascular cell growth promoters such as growth factors, transcriptional activators, and translational promoters.

Anti-Proliferative Agents

Anti-proliferative agents are substances used to prevent or retard the spread of cells such as vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins. Also including agents that prevent restenosis by reducing or preventing cell proliferation, especially in smooth muscle cells, when a device is inserted within the body. Examples of such agents include, but are not limited to, anti-proliferative agents such as mycophenolate mofetil, azathioprine, paclitaxel and sirolimus. Other examples are anti-neoplastic and anti-miotic agents such as cilostazol, everolimus, dicumarol, zotarolimus, carvedilol and the major taxane domain-binding drugs, such as paclitaxel and analogues thereof, epothilone, discodermolide, docetaxel, paclitaxel protein-bound particles such as ABRAXANE® (ABRAXANE is a registered trademark of ABRAXIS BIOSCIENCE, LLC), paclitaxel complexed with an appropriate cyclodextrin (or cyclodextrin like molecule), rapamycin and analogues thereof, rapamycin (or rapamycin analogs) complexed with an appropriate cyclodextrin (or cyclodextrin like molecule), siRNA, 17.beta.-estradiol, 17.beta.-estradiol complexed with an appropriate cyclodextrin, dicumarol, dicumarol complexed with an appropriate cyclodextrin, beta.-lapachone and analogues thereof, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine.

Anti-Inflammatory Agents

Anti-inflammatory agents are drugs reducing inflammation. Many steroids, to be specific glucocorticoids, reduce inflammation or swelling by binding to glucocorticoid receptors. These drugs are often referred to as corticosteroids. Non-steroidal anti-inflammatory drugs (NSAIDs) are active by counteracting the cyclooxygenase (COX) enzyme. Some common examples of NSAIDs are, but not limited to, aspirin, ibuprofen, and naproxen. Other specific COX-inhibitors may also be contemplated. Examples of anti-inflammatory agents are dexamethasone, prednisolone, steroids such as corticosterone, budesonide, estrogen, sulfasalazine and mesalamine, sirolimus and everolimus (and related analogs).

Specific agents having pharmacological activity that may be used in this invention include, but are not limited to, heparin, heparin derivatives, thrombin, collagen, itraconazole, suramin, RGD protein, silver compounds, triclosan, chlorhexidine, growth factors, paclitaxel, sirolimus, everolimus, dexamethasone and steroids.

Adhesive Agents

Adhesive agents are chemical compounds used to increase the tack or the stickiness of the surface. They can be high or low molecular weight compounds. Surfaces with tacky properties allow attachment and make coating pull-off much harder. Adhesive agents include, but are not limited to, partially cured systems, epoxide containing systems, tackifiers and foams thereof. Many biopolymers—proteins, carbohydrates, glycoproteins, and mucopolysaccharides—may be used to form hydrogels that contribute to adhesion.

Lubricious Agents

Lubricious agents are compounds that may increase the hydrophilicity of the present invention when introduced. Examples of hydrophilic agents are hydrophilic polymer independently selected from the group consisting of hyaluronic acid, a hyaluronic acid derivative, poly-N-vinylpyrrolidone, a poly-N-vinylpyrrolidone derivative, polyethylene oxide, a polyethylene oxide derivative, a polyalkylene glycol, a polyether derivative (e.g. polyethylene glycol (PEG), a polyethylene glycol (PEG) derivative, polypropylene glycol (PPG) or a polypropylene glycol (PPG) derivative), polyglycidol, polyvinylalcohol, a polyvinylalcohol derivative, polyacrylic acid, a polyacrylic acid derivative, silicone, a silicone derivative, polysaccharide, a polysaccharide derivative, polysulfobetaine, a polysulfobetaine derivative, polycarboxybetaine, a polycarboxybetaine derivative, a polyalcohol such as polyHEMA, a polyacid such as an alginate, dextran, agarose, poly-lysine, polymethacrylic acid, a polymethacrylic acid derivative, polymethacrylamide, a polymethacrylamide derivative, a polyacrylamide, polyacrylamide derivative, polysulfone, a polysulfone derivative, sulfonated polystyrene, a sulfonated polystyrene derivative, polyallylamine, a polyallylamine derivative, polyethyleneimine, a polyethyleneimine derivative, polyoxazoline, a polyoxazoline derivative, polyamine and a polyamine derivative. Block polymers of above mentioned polymers are also useful; e.g. poly(vinyl alcohol-co-ethylene), poly(ethyleneglycol-co-propyleneglycol), poly(vinyl acetate-co-vinyl alcohol), poly(tetrafluoroethylene-co-vinyl alcohol), poly(acrylonitrile-co-acrylamide), poly(acrylonitrile-co-acrylic acid-co-acrylamidine).

Conductive Agents

Conductive agents may also be incorporated into the coating of the present invention to provide conductive surfaces for devices such as electrodes. Examples of conductive agents include polyfluorenes, polyphenylenes, polypyrenes, polyazulenes, polynaphthalenes, polypyrroles (PPY), polycarbazoles, polyindoles, polyazepines, polyanilines, polythiophenes (PT), poly(3,4-ethylenedioxythiophene) (PEDOT), poly(p-phenylene sulfide), polyacetylenes (PAC), Poly(p-phenylene vinylene) (PPV) or derivatives thereof.

Weight Ranges for Component C

In one embodiment, component C has molecular weight of 2,000,000 Da or below. In another embodiment, component C has molecular weight between 100,000 Da and 1,500,000 Da.

In one embodiment, component C has molecular weight of 100,000 Da or below e.g. 50,000 Da or below (e.g. 50-3,000 Da) e.g. 25,000 Da or below (e.g. 9,000-20,000 Da e.g. 9,000-11,000 Da) e.g. 1,000 Da or below (e.g. 150-600 Da).

In another embodiment, component C is a protein which has molecular weight between 40,000 Da and 80,000 Da. In another embodiment, component C is a polymeric conductive agent which has molecular weight between 1,000 Da and 30,000 Da.

In one embodiment, component C is present and comprises and suitably consists of heparin or a heparin derivative bearing one or more (e.g. one) alkene or alkyne groups, suitably one or more (e.g. one) alkene group. Heparin or a heparin derivative as described above can be modified by any suitable method to bear alkene or alkyne groups. Example 6 describes a specific synthesis of end-point methacrylated heparin. Example 5.7 explains how a coating of the invention comprising said heparin incorporated within the copolymer may be prepared.

Component D

Component D is an optional component in the hydrophilic coating of the invention. If present, component D comprises and suitably consists of one or more low molecular weight cross-linking agents each bearing two or more functional groups independently selected from thiol, alkene and alkyne groups. The functional groups of D take part in the radical polymerisation reaction to form the copolymer. For example, component D comprises and suitably consists of one or more low molecular weight cross-linking agents each bearing two or more thiol groups e.g. two thiol groups. The thiol groups participate in the radical polymerisation reaction via thiol ene/yne reactions to form a cross-linked copolymer.

The presence of optional component D may tend to enhance the structural stability of the copolymer and hence the structural stability of the coating. The presence of optional component D may tend to enhance the durability of the coating.

Low molecular weight cross-linking agents (including low molecular weight PEGs) will typically have a molecular weight of less than 1000 Da e.g. less than 600 Da e.g. 100-1000 Da e.g. 100-600 Da.

In one embodiment, the cross-linking agent may be, but not limited to, bisphenol A propoxylate diacrylate, 1,3-butanediol diacrylate, 1,4-butanediol diacrylate, 1,3-butanediol dimethacrylate, 1,4-butanediol dimethacrylate, N,N'-(1,2-dihydroxyethylene)bisacrylamide, di(trimethylolpropane)tetraacrylate, diurethane dimethacrylate, N,N'-ethylenebis(acrylamide), glycerol 1,3-diglycerolate diacrylate, glycerol dimethacrylate, glycerol propoxylate (1PO/OH)triacrylate, 1,6-hexanediol diacrylate, 1,6-hexanediol dimethacrylate, 1,6-hexanediol ethoxylate diacrylate, 1,6-hexanediylbis[oxy(2-hydroxy-3,1-propanediyl)]bisacrylate, hydroxypivalyl hydroxypivalate bis[6-(acryloyloxy)hexanoate], neopentyl glycol diacrylate, pentaerythritol diacrylate monostearate, pentaerythritol propoxylate triacrylate, pentaerythritol triacrylate, poly(propylene glycol)diacrylate, poly(propylene glycol)dimethacrylate, 1,3,5-triacryloylhexahydro-1,3,5-triazine, tricyclo[5.2.1.02,6]decanedimethanol diacrylate, trimethylolpropane benzoate diacrylate, trimethylolpropane ethoxylate triacrylate, trimethylolpropane propoxylate triacrylate, trimethylolpropane triacrylate, tri(propylene glycol) diacrylate or tris[2-(acryloyloxy)ethyl]isocyanurate. Acrylated or methacrylated low molecular weight PEGs are also useful.

In another embodiment, the cross-linking agent may be, but not limited to, N,N'-methylenebisacrylamide, 3-(acryloyloxy)-2-hydroxypropyl methacrylate or bis[2-(methacryloyloxy)ethyl]phosphate. Acylamides and methacrylamides derivatised from low molecular weight PEGs are also useful.

In another embodiment, the cross-linking agent may be, but not limited to, a polyallyl such as 2,4,6-triallyloxy-1,3,5-triazine, 1,3,5-triallyl-1,3,5-triazine-2,4,6(1H,3H,5H)-trione, trimethylolpropane allyl ether, trimethylolpropane diallyl ether pentaerythritol allyl ether, diallyl carbonate, diallyl maleate and diallyl succinate. Allyl functionalized low molecular weight PEGs are also useful.

In another embodiment, the cross-linking agent may be, but not limited to, a polyfunctional thiolated PEG such as hexa(ethylene glycol)dithiol, 1,2-ethanedithiol, 1,3-propanedithiol, 2,3-dimercapto-1-propanol and 1,3,5-triazine-2,4,6-trithiol.

In another embodiment, the cross-linking agent may be, but not limited to, 1,6-heptadiyne, 3-(allyloxy)-1-propyne, propargyl ether and 2-methyl-1-buten-3-yne. Alkyne functionalized low molecular weight PEGs are also useful.

In a preferred embodiment, the cross-linking agent may be, but are not limited to, alkene and/or thiol and/or alkyne and/or functionalized low molecular weight PEG.

A thiol containing Component D may be included advantageously to reduce the sensitivity of the system to oxygen inhibition of the polymerization reaction.

Component E

Component E, if present, comprises and suitably consists of one or more beneficial agents, wherein component E does not form a copolymer with components A, B, C (if present) and D (if present). The presence of component E will tend to modify the properties of the hydrophilic coating which comprises it.

In one embodiment, component E is covalently attached to the copolymer. This embodiment is particularly suitable when it is desired to avoid any elution from the coating of the component E.

In one embodiment, component E is not covalently attached to the copolymer. For example, component E is ionically associated with the copolymer. Alternatively component E can be entrapped within the copolymer without being chemically or ionically bound to the copolymer. For example component E can be absorbed into the copolymer by a process involving swelling of the preformed copolymer on the surface of the substrate with a solution comprising component E. The component E will be taken up into voids within the copolymer as it swells.

Thus in certain embodiments component E may elute from the hydrophilic coating over time.

This is particularly useful if component E is a pharmacological agent, wherein systemic administration as well as local administration of the agent is advantageous. The distribution and elution over time may be controlled.

Component E can be a mixture of sub-components in which (at least) one subcomponent is covalently attached to the copolymer and (at least) one subcomponent is not covalently attached to the copolymer.

Beneficial agents include those described under the section headed "Component C". Beneficial agents may or may not be functionalised—for example they can be functionalised when they are to be covalently attached to the copolymer.

Additional beneficial agents as component E include salts that when in contact with water will aid conductivity of the hydrophilic coating. Such salts can be, but are not limited to, lithium, sodium or potassium chloride. Metals such as gold and silver may also be used as conductive agents.

Thus, for example, component E can be reacted with the already formed copolymer of components A and B (and optional other components C and D) as a coating on the substrate, in a reaction subsequent to the polymerisation reaction.

For example, if component A were acrylic acid and component B were diacrylate-functionalised PEG polymer then the resulting copolymer of components A and B would have pendant carboxylic acid groups. Those carboxylic acid groups on the surface of the copolymer could then react with a suitably functionalised component E (e.g. using a coupling agents such as carbodiimide and an amine-functionalised component E). Alternatively, component E could be functionalised with thiol groups then linked to residual alkene or alkyne groups on the surface of the copolymer of components A and B and optional C and/or D under UV irradiation via a thiol-ene or thiol-yne reaction.

Component E can be introduced by covalent coupling of component E to the coating using carbodiimide chemistry to form an amide linkage, reductive amination reactions to form an amine linkage, azide-alkyne reactions to form a triazole linkage and thiol-alkene/yne reactions to form a thioether linkage.

The aforementioned methods are merely exemplary and the skilled person could apply any suitable coupling technique to covalently attach component E to the copolymer. In this aspect of the embodiment, component E can tend to reside mostly on the outer surface of a coating of the polymer on the substrate. In another aspect, component E can be distributed throughout the coating.

In one embodiment, component E is present and comprises and suitably consists of or comprises heparin or a heparin derivative which can be covalently coupled, end-point or single-point or multi-point, to the copolymer as a coating on the substrate. In another embodiment, component E is present and comprises and suitably consists of or comprises heparin or a heparin derivative which may covalently coupled, end-point or single-point or multi-point, to a polyamine such as polyethyleneimine which can be ionically associated with the copolymer as a coating on the substrate. Heparin or a heparin derivative as described above can be modified by any suitable method to facilitate coupling to the coating. Examples 5.2-5.4 and Example 5.8 describe how heparin may be attached to a copolymer of the invention.

Embodiment Variations for the Hydrophilic Coating

In one embodiment component C is present and component D is not present. In one embodiment component D is present and component C is not present. In one embodiment components C and D are not present. In one embodiment components C and D are present.

In one embodiment component E is present. In one embodiment component E is not present.

Other Aspects of the Hydrophilic Coating

The relative proportions of component A and component B must be such that the coating has structural integrity while retaining its hydrophilic properties. For example, if the relative proportion of component A is too high compared with the proportion of component B, the coating can be less flexible and not sufficiently hydrophilic. Conversely, if the relative proportion of component B is too high compared to the proportion of component A, then the coating may not have sufficient structural integrity to withstand delamination. If component C is present, the relative proportions of components A, B and C and optionally D much be such that coating exhibits the beneficial property associated with component C but is still hydrophilic and structurally stable.

Exemplary (non-limiting) ratios of components are set out in the following Tables A and B:

TABLE A

| Exemplary ratio | Component (low w/w ratio-high w/w ratio) | | | | |
|---|---|---|---|---|---|
| | A | B | C | D | E |
| 1 | 1 | 0.1-4 e.g. 0.75-3.5 e.g. 0.75-2.5 e.g. 1-2 | — | — | — |
| 2 | 1 | 0.1-4 | 0.001-10 | — | — |
| 3 | 1 | 0.1-4 | — | 0.01-1 | — |
| 4 | 1 | 0.1-4 | — | — | 0.001-10 |
| 5 | 1 | 0.1-4 | 0.001-10 | 0.01-1 | — |
| 6 | 1 | 0.1-4 | 0.001-10 | — | 0.001-10 |
| 7 | 1 | 0.1-4 | — | 0.01-1 | 0.001-10 |
| 8 | 1 | 0.1-4 | 0.001-10 | 0.01-1 | 0.001-10 |

TABLE B

| Exemplary coating | A structural monomer | B hydrophilic polymer | C or E anti-thrombogenic agents | hemostatic agents | anti-angiogenic agents | angiogenic agents | anti-microbial agents | anti-proliferative agents | proliferative agents | anti-inflammatory agents | adhesive agents | lubricious agents | conductive agents |
|---|---|---|---|---|---|---|---|---|---|---|---|---|---|
| 1 | 1 | 0.1 | 0.01 | — | — | — | — | — | — | — | — | — | — |
| 2 | 1 | 1 | 6.5 | — | — | — | — | — | — | — | — | — | — |
| 3 | 1 | 1 | — | 1 | — | — | — | — | — | — | — | — | — |
| 4 | 1 | 2 | — | — | 0.01 | — | — | — | — | — | — | — | — |
| 5 | 1 | 0.75 | — | — | — | 0.01 | — | — | — | — | — | — | — |
| 6 | 1 | 1.5 | — | — | — | — | 0.1 | — | — | — | — | — | — |
| 7 | 1 | 2 | — | — | — | — | — | 0.001 | — | — | — | — | — |
| 8 | 1 | 4 | — | — | — | — | — | — | 0.01 | — | — | — | — |
| 9 | 1 | 1.5 | — | — | — | — | — | — | — | 0.1 | — | — | — |
| 10 | 1 | 1 | — | — | — | — | — | — | — | — | 1 | — | — |
| 11 | 1 | 0.75 | — | — | — | — | — | — | — | — | — | 10 | — |
| 12 | 1 | 3 | — | — | — | — | — | — | — | — | — | — | 1 |
| 13 | 1 | 1 | 4 | — | — | — | 0.01 | — | — | — | — | — | — |
| 14 | 1 | 1.5 | 2 | — | — | — | 0.1 | — | — | 0.1 | — | — | — |
| 15 | 1 | 1 | 10 | — | — | — | — | 0.01 | — | — | — | — | — |

The above mentioned ratios refer to the mass ratio of components A, B, C and D (as appropriate) present in the polymerisation solution before polymerisation takes place. The ratio of components A, B, C and D present in the resulting coating (or at the least the relative proportions of the copolymer derived from components A, B, C and D) may reasonably be expected to be substantially similar to the mass ratio of the individual components in the polymerisation solutions before the coating is formed. The ratio involving E refers to the mass ratio of E in solution, with respect to the ratio of components A, B, C and D in the polymerisation solution, in any subsequent step involving reaction or association of E with the copolymer of compounds A, B, C and D.

The dry thickness of the hydrophilic coating on the substrate can be controlled by limiting the quantities of components A, B and optionally C and D in the polymerisation solution and/or by limiting the polymerisation time and/or by appropriate modification of the conditions of incorporation of E where present. Suitably, the hydrophilic coating is at least 100 µm thick when dry, for example at least 50 µm, 25 µm 10 µm, 5 µm, 1 µm, 0.5 µm or 0.1 µm. In one embodiment, the coating of the copolymer is 0.1-5 µm thick, for example 0.1-2.5 µm or 0.5-2.5 µm.

Method of Forming the Hydrophilic Coating

The present invention provides a method of forming a hydrophilic coating which is covalently attached to the surface of a substrate, wherein said method comprises the steps of:

(a) contacting the surface with a mixture comprising components A and B, optional component C, optional component D and a radical initiator; wherein component A comprises and suitably consists of one or more $C_2$-$C_{16}$ hydrophilic monomers each bearing one or more alkene and/or alkyne groups;

component B comprises and suitably consists of one or more hydrophilic polymers each bearing two or more alkene and/or alkyne groups;

component C, if present, comprises and suitably consists of one or more beneficial agents each bearing one or more (e.g. one) alkene or alkyne groups; and component D, if present, comprises and suitably consists of one or more low molecular weight cross-linking agents each bearing two or more functional groups independently selected from thiol, alkene and alkyne groups; and (b) initiating radical polymerisation involving the alkene and/or alkyne groups of components A, B and C (if present) and involving the functional groups of component D (if present) in order to form a cross-linked copolymer of component A, component B, and optional components C and D; wherein said copolymer is covalently linked to the surface; and (c) optionally incorporating into the hydrophilic coating a component E which comprises and suitably consists of one or more beneficial agents, wherein component E does not form a copolymer with components A, B, C (if present) and D (if present).

The invention also provides a substrate with a hydrophilic coating obtainable by the method described above.

The present invention also provides a device obtainable by the aforementioned method.

It should be noted that all aspects of the invention as described above and herein refer equally to a substrate of the invention and the method of the invention.

The hydrophilic coating of the invention can be formed by contacting the surface of the substrate with a solution comprising components A and B and optionally components C and D, and a radical initiator (referred to herein as the polymerisation solution). Suitably, the reaction solvent is a polar solvent such as an alcohol (for example methanol, ethanol, propanol or isopropanol), THF or DMF, or aqueous solutions of any of the aforementioned solvents. Thus, in one embodiment the polymerisation solvent is selected from methanol, ethanol, propanol, isopropanol, THF or DMF. In another embodiment, the solvent is selected from ethanol, propanol or isopropanol, or aqueous solutions thereof. In another embodiment, the solvent is ethanol. In a further embodiment, the solvent is water per se. Thus, the coating of the present invention can be prepared using Class 3 or Class 2 solvents avoiding the use of organic solvents listed as Class 1 in the USP chapter describing residual solvents. Suitably, the coating of the invention can be prepared using Class 3 solvents alone, thereby avoiding the use of organic solvents listed as Class 2 and Class 1, and thereby circumventing the need for further purification steps to remove traces of residual solvent from the final hydrophilic coating.

The method of the invention results in the formation of a hydrophilic coating which is covalently attached to the surface of a substrate. The covalent attachment is achieved via reaction between groups on the surface of the substrate with alkene and/or alkyne groups on components A, B and C (if present) and with functional groups of component D (if present).

The hydrophilic coating of the present invention is formed by free radical polymerisation (referred to herein as radical polymerisation) of components A, B and optionally C and D to form a copolymer that is covalently linked to the surface. In an embodiment, the radical polymerisation is initiated by abstracting hydrogen atoms from the surface comprising abstractable hydrogen atoms (which can be the surface of the substrate itself or a surface priming coating of a polymer comprising abstractable hydrogen atoms) using a free radical initiator (referred to herein as a radical initiator) sometimes referred to as a "Norrish Type II" or "Type II" radical initiator. In another embodiment, the radical polymerisation is initiated by generation of radicals in the bulk which radicals react with polymerisable groups in the bulk and at the surface. Initiators for such a process are thermal initiators and/or radical initiators. These radical initiators are sometimes called "Norrish Type I" or "Type I" radical initiators.

Free radical initiators ("radical initiators") are molecules that readily re-arrange/decompose to form free radical species (the initiating species), which in turn react with component A, B and (optionally) C and D (embodiment (i)) or reactive groups on the surface of the substrate (embodiment (ii)) to form further radical species. These two steps are collectively known as initiation. In a free radical polymerisation reaction, the free radical species generated by the initiating species react further in a chain reaction addition of component A, B and (optionally) C and D.

A photoinitiator is a compound that yields free radicals when exposed to UV or visible light. Based on the mechanism of radical formation, photoinitiators are generally divided into two classes: Type I photoinitiators undergo a unimolecular bond cleavage upon irradiation to yield free radicals. Type II photoinitiators undergo a bimolecular reaction where the excited state of the photoinitiator interacts with a second molecule (a coinitiator, usually a H-donor) to generate free radicals via hydrogen abstraction mechanisms. Subsequent polymerisation is usually initiated by the radicals produced from the coinitiator. UV photoinitiators of both Type I and Type II are available. However, visible light photoinitiators belong almost exclusively to the Type II class of photoinitiators.

Suitable UV photoinitiators include benzophenones, xanthones, thioxanthones, benzoin ethers, benzyl ketals, α-dialkoxyacetophenones, α-hydroxyalkylphenones, α-aminoalkylpheneones and acyl phosphine oxides.

Once the surface to be coated is in contact with the polymerisation solution, polymerisation is initiated by any suitable means for the particular initiator used. For example, when the radical initiator is a photoinitiator polymerisation is initiated by exposure of the polymerisation solution to UV light. When UV light is used to initiate polymerisation, any suitable UV source can be used, for example a Fusion UV-lamp or Oriel UV-lamp providing UV-A and/or UV-B and/or UV-C radiation. If a thermal initiator is used, heat can be provided by any suitable means such as an oven or a heating element. When a photoinitiator is used to initiate polymerisation, preferably the reaction proceeds at room temperature.

To circumvent the problem of oxygen inhibition which may result in insufficient curing, inert curing conditions may be used.

In one embodiment, the polymerisation takes place under inert atmosphere e.g. polymerisation under argon atmosphere, e.g. polymerisation under nitrogen atmosphere.

In another embodiment, polymerisation solutions may be purged with inert gas prior to polymerisation to increase polymerisation kinetics and improve curing. Polymerisation solutions may be purged with e.g. argon gas or nitrogen gas.

Embodiment (i)

In a first embodiment, the covalent attachment between the surface of the substrate and the hydrophilic coating is formed via the reaction of surface-bound radicals on the surface of the substrate with a component of the hydrophilic coating, and wherein the surface bound radicals are generated via abstraction of hydrogen atoms from the surface of the substrate.

As illustrated in FIG. 1 in this embodiment polymerisation is initiated when a radical initiator in a liquid phase in contact with the surface abstracts hydrogen atoms from the surface of the substrate to form surface bound radicals. The surface bound radicals react with at least one of components A, B and C and D (if present and capable of such reaction—in FIG. 1 only components A and B are illustrated) to covalently bind the copolymer to the surface. The copolymer can be covalently linked to the surface via all components A, B and C and D if present (or at least via components of the copolymer that previously existed as either component A or component B or component C or component D if present). The relative amounts of each of component will to a certain extent determine the proportion of covalent linkages via component A and/or component B and/or component C and/or component D if present. However, which component preferentially reacts with the surface bound radicals is also determined by the relative reactivity of the components which is determined by the reactivity of the alkene and/or alkyne functionalities on the components. If the proportion of components A and B (and C and D if present and capable of such reaction) were equal, then the component with the most reactive alkene or alkyne group would be expected to react preferentially with the surface bound radicals.

Suitably, the alkene and/or alkyne groups of components A, B, C and D (if present and capable of reacting) will react with the surface bound radicals at a substantially similar rate. Thus, the proportion of copolymer linked to the surface by components A, B, C and D (if present and capable of reacting) or at least via components of the copolymer that previously existed as either component A or component B or component C or component D (if present and capable of reacting) is directly related to the proportions of each component present in the polymerisation solution. For example, when component A is acrylic acid and component B is diacrylate-functionalised PEG, the alkene groups on each component will react with the surface bound radicals at an essentially similar rate and the copolymer will be bound to the surface via both components A and B.

Thus, in one embodiment, the invention provides a method of forming a hydrophilic coating which is covalently attached to the surface of a substrate, the substrate having a surface comprising abstractable hydrogen atoms; wherein said method comprises the steps of:

(a) contacting the surface with a mixture comprising components A and B, optional component C, optional component D and a radical initiator capable of abstracting hydrogen atoms from the surface to generate surface-bound radicals; wherein component A comprises and suitably consists of one or more $C_2$-$C_{16}$ hydrophilic monomers each bearing one or more alkene and/or alkyne groups;

component B comprises and suitably consists of one or more hydrophilic polymers each bearing two or more alkene and/or alkyne groups;

component C, if present, comprises and suitably consists of one or more beneficial agents each bearing one or more (e.g. one) alkene or alkyne groups; and component D, if present, comprises and suitably consists of one or more low molecular weight cross-linking agents each bearing two or more functional groups independently selected from thiol, alkene and alkyne groups; and (b) initiating radical polymerisation involving the alkene and/or alkyne groups of components A, B and C (if present) and involving the functional groups of component D (if present) in order to form a cross-linked copolymer of component A, component B, and optional components C and D; wherein said copolymer is covalently linked to the surface via reaction of the surface bound radicals; and (c) optionally incorporating into the hydrophilic coating a component E which comprises and suitably consists of one or more beneficial agents, wherein component E does not form a copolymer with components A, B, C (if present) and D (if present).

As described above, in this embodiment a substrate with a surface comprising abstractable hydrogen atoms is required.

"Abstractable hydrogen atoms" are defined as covalently bound hydrogen atoms that can be abstracted or removed by an entity, being in an excited state, and thereby generating a free radical (at least initially) at the atom which was previously covalently bound to the hydrogen atom. Abstractable hydrogen atoms are usually those which, when abstracted, leave behind a stabilised radical. Radical stability depends on a number of factors, including the nature of the atom bearing the radical (for example, its hybridisation), the nature of the atoms adjacent to the radical (for example, unsaturation which will allow radical delocalisation) and steric constraints, which may hinder the radical centre from reacting further.

The substrate having a surface comprising abstractable hydrogen atoms may have an "intrinsic surface comprising abstractable hydrogen atoms" meaning the material from which the surface of the substrate is made (prior to any coating process) comprises abstractable hydrogen atoms.

Thus, in one embodiment, the surface of the substrate itself comprises abstractable hydrogen atoms (as used herein). Substrates having an intrinsic surface comprising abstractable hydrogen atoms are formed from (or at least a part of the surface is formed from) a substrate material having abstractable hydrogen atoms. Examples of substrate materials that may be modified to carry abstractable hydrogen atoms and/or having an intrinsic surface comprising abstractable hydrogen atoms include, but are not limited to, polyolefins, polyesters, polyurethanes, polyamides, polyether block amides, polyimides, polycarbonates, polyphenylene sulfides, polyphenylene oxides, polyethers, silicones, polycarbonates, polyhydroxyethylmethacrylate, polyvinyl pyrrolidone, polyvinyl alcohol, rubber, silicone rubber, polyhydroxyacids, polyallylamine, polyallylalcohol, polyacrylamide, and polyacrylic acid, styrenic polymers, polytetrafluoroethylene and copolymers thereof, derivatives thereof and mixtures thereof. Some of these classes are available both as thermosets and as thermoplastic polymers. As used herein, the term "copolymer" shall be used to refer to any polymer formed from two or more monomers, e.g. 2, 3, 4, 5 and so on and so forth. Bioresorbables, such as poly(D,L-lactide) and polyglycolids and copolymers thereof are also useful. Useful polyamides include, but are not limited to, nylon 12, nylon 11, nylon 9, nylon 6/9 and nylon 6/6. Examples of some copolymers of such materials include the polyether-block-amides, available from Elf Atochem North America in Philadelphia, Pa. under the tradename of PEBAX®. Another suitable copolymer is a polyetheresteramide. Suitable polyester copolymers, include, for example, polyethylene terephthalate and polybutylene terephthalate, polyester ethers and polyester elastomer copolymers such as those available from DuPont in Wilmington, Del. under the tradename of HYTREL® Block copolymer elastomers such as those copolymers having styrene end blocks, and midblocks formed from butadiene, isoprene, ethylene/butylene, ethylene/propene, and so forth may be employed herein. Other styrenic block copolymers include acrylonitrile-styrene and acrylonitrile-butadiene-styrene block copolymers. Also, block copolymers wherein the particular block copolymer thermoplastic elastomers in which the block copolymer is made up of hard segments of a polyester or polyamide and soft segments of polyether may also be employed herein. Other useful substrates are polystyrenes, poly(methyl)methacrylates, polyacrylonitriles, poly(vinylacetates), poly(vinyl alcohols), chlorine-containing polymers such as poly(vinyl)chloride, polyoxymethylenes, polycarbonates, polyamides, polyimides, polyurethanes, phenolics, amino-epoxy resins, polyesters, silicones, cellulose-based plastics, and rubber-like plastics.

Combinations of these materials can be employed with and without cross-linking.

Polymeric substrates may optionally be blended with fillers and/or colorants.

In one embodiment, said biocompatible material carrying abstractable hydrogen atoms is a polyether-block-amides, such as PEBAX®.

In another embodiment, the material is a protein, such as silk or wool, agarose, or alginate. Also, certain metals and ceramics, which could be modified to carry abstractable hydrogen atoms, may be used as substrates for the present invention. Suitable metals include, but are not limited to, biocompatible metals, titanium, stainless steel, high nitrogen stainless steel, gold, silver, rhodium, zinc, platinum, rubidium, copper and magnesium, and combinations thereof. Suitable alloys include cobalt-chromium alloys such as L-605, MP35N, Elgiloy, nickel-titanium alloys (such as Nitinol), tantalum, and niobium alloys, such as Nb-1% Zr, and others. Ceramic substrates may include, but are not limited to, silicone oxides, aluminum oxides, alumina, silica, hydroxyapapitites, glasses, calcium oxides, polysilanols, and phosphorous oxide.

In one embodiment, said biocompatible metal is a nickel-titanium alloy, such as Nitinol.

In another embodiment, substrates that may be modified to carry abtractable hydrogen atoms and/or having an intrinsic surface comprising abstractable hydrogen atoms include include, but are not limited to, fluorinated polymers such as fluoropolymers, e.g expanded polytetrafluoroethylene (ePTFE), polytetrafluoroethylene (PTFE), fluorinated ethylene-propylene (FEP), perfluorocarbon copolymers, e.g. tetrafluoroethylene perfluoroalkylvinyl ether (TFE/PAVE) copolymers, copolymers of tetrafluoroethylene (TFE) and perfluoromethyl vinyl ether (PMVE), and combinations of the above with and without crosslinking between the polymer chains, expanded polyethylene, polyvinylchloride, polyurethane, silicone, polyethylene, polypropylene, polyurethane, polyglycolic acid, polyesters, polyamides, elastomers and their mixtures, blends and copolymers or derivatives thereof may be useful.

Alternatively, the substrate can be coated with a surface coating of a polymer comprising abstractable hydrogen atoms. Thus, in an alternative embodiment, the surface of the substrate is a surface coating of a polymer comprising abstractable hydrogen atoms. The surface coating of a polymer comprising abstractable hydrogen atoms is also referred to herein as "a surface priming coating of a polymer comprising abstractable hydrogen atoms" or as "a surface priming coating of {specific polymer comprising abstractable hydrogen atoms}", indicating that the hydrophilic coating of the invention is applied onto the surface coating of a polymer comprising abstractable hydrogen atoms. Application of the polymer comprising abstractable hydrogen atoms may result in a more uniformly applied subsequent coating of the copolymer of components A, B and optionally C and D. A uniform coating with sufficient adhesion is desirable from a regulatory perspective where a particular coating uniformity can be required to meet performance specifications. Also, the strong adhesion between the priming layer and the substrate is desirable from regulatory perspective since this will prevent delamination and particulation.

In this embodiment, suitably the substrate to be coated does not have an intrinsic surface comprising abstractable hydrogen atoms or has an insufficient quantity of abstractable hydrogen atoms, therefore the surface priming coating of the polymer provides the required surface comprising abstractable hydrogen atoms. However, a substrate having an intrinsic surface comprising abstractable hydrogen atoms may also have a surface priming coating of a polymer comprising abstractable hydrogen atoms. Thus, in a further embodiment, a substrate having a surface comprising abstractable hydrogen atoms is coated with a surface priming coating of a polymer comprising abstractable hydrogen atoms. This has the additional benefit of providing a more uniform distribution of abstractable hydrogen atoms on a surface.

In at least some aspects of this embodiment, the application of the hydrophilic coating is substrate independent, i.e. as long as at least a part of the substrate can be coated with a surface coating of a polymer comprising abstractable hydrogen atoms, then (in principle) that part of the substrate can be provided with a hydrophilic coating. Thus, in this embodiment, the quantity or type of abstractable hydrogen atoms on the surface of a substrate need not be evaluated prior to application of the hydrophilic coating—the surface coating of the polymer provides the required abstractable hydrogen atoms.

Substrates having a surface priming coating of a polymer comprising abstractable hydrogen atoms are suitably prepared by subjecting the surface of the substrate with the appropriate monomer, under polymerisation conditions. Examples of polymers comprising abstractable hydrogen atoms include polymers comprising catechol functionality and/or quinone functionality and/or semi-quinone functionality. In one embodiment the polymer comprising abstractable hydrogen atoms is selected from the group consisting of polymers comprising catechol functionality, polymers comprising quinone-functionality, and polymers comprising semi-quinone functionality.

In one embodiment, the polymer comprising abstractable hydrogen atoms comprises catechol functionality, wherein said catechol functionality is illustrated by formula (III):

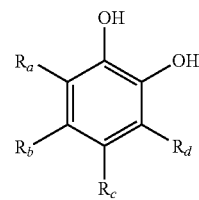
(III)

wherein, at least one of $R_a$, $R_b$, $R_c$ and $R_d$ are linked to the polymer and the remaining $R_a$, $R_b$, $R_c$ or $R_d$ are suitably H.

In one embodiment, the polymer comprising abstractable hydrogen atoms comprises semi-quinone functionality, wherein said semi-quinone functionality is illustrated by formula (IVa) or formula (IVb):

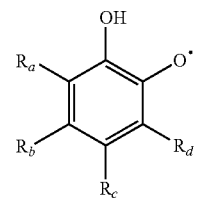
(IVa)

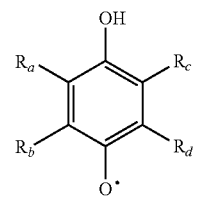
(IVb)

wherein, at least one of $R_a$, $R_b$, $R_c$ and $R_d$ are linked to the polymer and the remaining $R_a$, $R_b$, $R_c$ or $R_d$ are suitably H.

In one embodiment, the polymer comprising abstractable hydrogen atoms comprises quinone functionality, wherein said quinone functionality is illustrated by formula (Va) or formula (Vb):

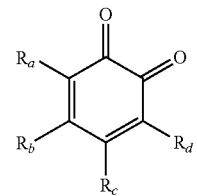
(Va)

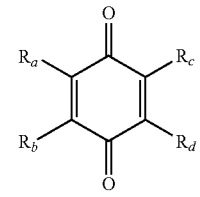
(Vb)

wherein, at least one of $R_a$, $R_b$, $R_c$ and $R_d$ are linked to the polymer and the remaining $R_a$, $R_b$, $R_c$ or $R_d$ are suitably H.

In one embodiment, the polymer comprising abstractable hydrogen atoms comprises catechol functionality formula (III) and/or semi-quinone functionality formula (IVa) and/or formula (IVb) and/or quinone functionality formula (Va) and/or (Vb).

Polydopamine

Figure 3:
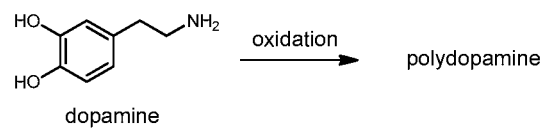
FIG. 3—shows various proposed structures for polydopamine.
Figure 3:
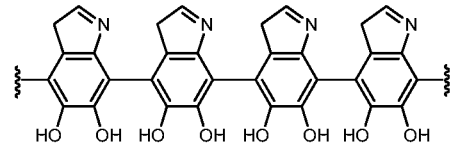
Figure 3:
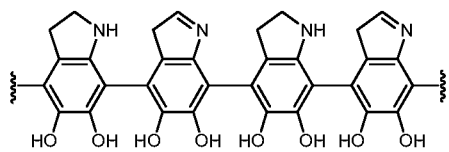
Figure 3:
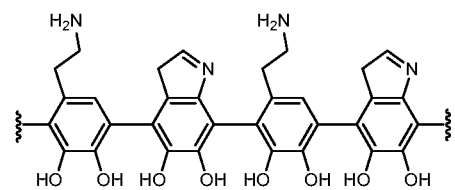
Figure 3:
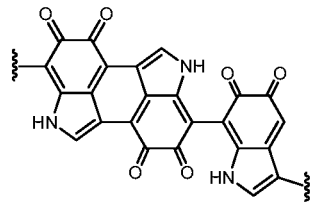
Figure 3:
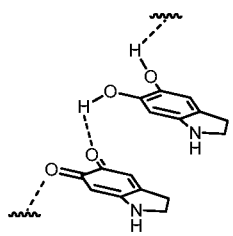

In one embodiment, the polymer comprising abstractable hydrogen atoms is polydopamine. Polydopamine is an example of a polymer comprising catechol functionality. In another embodiment, the polymer comprising abstractable hydrogen atoms comprises polydopamine. As discussed in the background of invention, polydopamine is formed by the polymerisation of the monomer dopamine. The exact structure of polydopamine is not well understood, and a number of structures have been proposed, as illustrated in FIG. 3.

Polymerisation of dopamine occurs under oxidative conditions, and mere exposure to the air (i.e. oxygen) is sufficient to initiate polymerisation. It is generally acknowledged that the initial oxidation of dopamine occurs on the catechol moiety, which then react with another molecule of dopamine, or can undergo an intermolecular cyclisation (via the pendant primary amine) to form a nitrogen-containing bicycle. Structure A of polydopamine (as described in WO2010/006196) suggests that polydopamine consists of repeating 5,6-dihydroxy-3H-indole units, cross-linked through positions 4 and 7. Structure B (as described by Zhao et al. Polym. Chem., 2010, 1, 1430-1433) suggests a similar polymer, but every other 5,6-dihydroxy-3H-indole unit is replaced with a 5,6-dihydroxyindoline unit. Structure C is proposed by the present inventors as another possible structure for polydopamine, which again is similar to Structure A, but every other 5,6-dihydroxy-3H-indole unit is replaced with an uncyclised dopamine molecule. This structure of polydopamine therefore comprises primary amine functionalities. Structure D (described in Kang et al. Langmuir, 2009, 25, 9656-9659) is also proposed by the present inventors and suggests attachment between dopamine molecules at the five-membered nitrogen ring, as well as between the catechol rings. This structure also suggests that quinone rings as well as catechol rings are present in the polymeric structure. Finally, Structure E (described by Dreyer et al. Langmuir, 2012, 28, 6428-6435) illustrates a completely different structure in which polydopamine is not a covalent polymer but is instead a supramolecular aggregate of monomers, consisting primarily of 5,6-dihydroxyindoline and its dione derivative.

It should be noted that in the context of the present invention, the representation of the structure of polydopamine is immaterial for working the method and coating of the invention, and the discussion above is merely included for background reference.

In one aspect, the invention provides a substrate having a first coating and a second coating, wherein the first coating is a surface priming coating of polydopamine and the second coating is a hydrophilic coating comprising a cross-linked copolymer of components A and B, and optional components C and D; wherein component A comprises and suitably consists of one or more $C_2$-$C_{16}$ hydrophilic monomers each bearing one or more alkene and/or alkyne groups;

component B comprises and suitably consists of one or more hydrophilic polymers each bearing two or more alkene and/or alkyne groups;

component C, if present, comprises and suitably consists of one or more beneficial agents each bearing one or more (e.g. one) alkene or alkyne groups; and component D, if present, comprises and suitably consists of one or more low molecular weight cross-linking agents each bearing two or more functional groups independently selected from thiol, alkene and alkyne groups;

wherein the cross-linked copolymer is formed by radical polymerisation involving the alkene and/or alkyne groups of components A, B and C (if present) and involving the functional groups of component D (if present);

wherein the hydrophilic coating optionally comprises component E which comprises and suitably consists of one or more beneficial agents, wherein component E does not form a copolymer with components A, B, C (if present) and D (if present);

and wherein the second coating is covalently attached to the first coating.

It should be generally noted that "a substrate having a first coating and a second coating . . . " should not be taken to mean "a substrate consisting of a first coating and a second coating . . . "—one or more additional coatings can be applied to the substrate prior to application of the first coating, and/or one or more additional coatings can be applied to the substrate after application of the second coating. For example, in the aspect of the invention above, there can be one or more additional coatings between the substrate and the surface priming coating of polydopamine, and/or one or more additional coating can be applied on top of the second (hydrophilic) coating.

As referred to herein, "polydopamine" is suitably formed by polymerisation of dopamine and/or a dopamine analogue. Preferably, polydopamine is formed by polymerisation of dopamine Dopamine analogues include molecules involved in the same or similar biochemical pathways as dopamine and those that are similar in structure to dopamine, including oxidised derivatives of tyrosine. In one embodiment, a dopamine analogue is a compound of formula (II), wherein one or more of $R^1$-$R^9$ are not H:

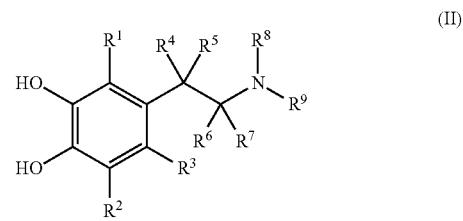

(II)

In another embodiment, a dopamine analogue is a compound of formula (II), wherein $R^1$-$R^9$ are independently selected from the group consisting of: H, $C_1$-$C_8$alkyl, $C_2$-$C_8$alkenyl, $C_2$-$C_8$alkynyl, —OH, —$CO_2H$, —C(O)$C_1$-$C_8$alkyl, —C(O)$C_2$-$C_8$alkenyl, —C(O)$C_2$-$C_8$alkynyl. Suitably, the compound of formula (II) comprises at least one abstractable hydrogen atom.

Naturally occurring dopamine analogues include:

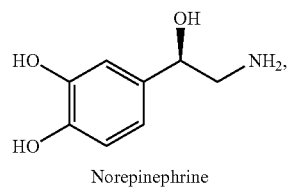

Norepinephrine

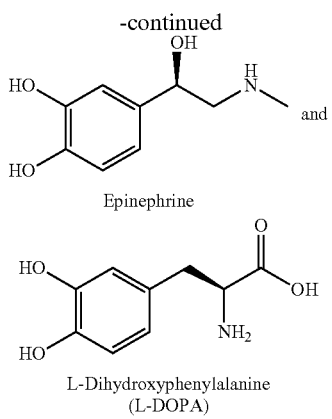

Epinephrine

L-Dihydroxyphenylalanine
(L-DOPA)

Methods for Preparing a Polydopamine Coating

As mentioned above, dopamine in aqueous alkaline solution exposed to the air (i.e. oxygen) will polymerise to form polydopamine without additional reactants. However, the rate of polymerisation can be increased by the addition of an oxidant to the solution containing dopamine. Suitable oxidants include but are not limited to ammonium persulfate and sodium persulfate. Thus, in one embodiment, a surface coating of polydopamine is formed by contacting the surface of the substrate with a mixture comprising oxidant and dopamine and/or a dopamine analogue.

Polymerisation of dopamine has also been observed to be quicker in alkaline aqueous solution, presumably due to deprotonation and activation of the catechol hydroxyl groups to oxidation. However, as described in Example 1.8, the present inventors have advantageously found that the use of an oxidant allows the polymerisation of dopamine to proceed in a controlled manner at neutral or even acidic pH, within a reasonable time frame. Suitable oxidants include ammonium persulfate and sodium persulfate.

Thus, in one embodiment, the surface coating of polydopamine is formed by contacting the surface of the substrate with a mixture comprising oxidant and dopamine and/or a dopamine analogue, at pH 4-10, for example pH 7. In another embodiment, the surface coating of polydopamine is formed at pH <7 e.g. pH 4-7. In a further embodiment, the surface coating of polydopamine is formed at pH 5-6.9 e.g. 5.5-6.5. The pH of the dopamine and/or dopamine analogue solution can be adjusted using any suitable acid or base, such as HCl or NaOH, respectively.

Coating a substrate with a surface coating of polydopamine under acidic or neutral conditions rather than the prior art basic conditions advantageously allows substrates which are base-sensitive to be coated with a hydrophilic coating of the invention. However, the present inventors have found that polymerisation of dopamine (or a dopamine analogue) under acidic or neutral conditions (i.e. pH <7) has the additional benefit of greatly reducing the precipitation of polydopamine particles or aggregates formed in the bulk and on the surface of the coating of polydopamine.

Based on the results set forth in the Examples, the inventors concluded that a pH value of around 6 was optimum for allowing a convenient polymerisation time of dopamine for achieving a coating of adequate thickness before particulation occurs to a significant extent. Although the polymerisation reaction is slower at more acidic pH, the inventors have observed that the reaction is more controlled due to the slower kinetics and the precipitation of polydopamine particles and aggregates can be minimised for a given time of polymerisation. As discussed in the background of invention, particulation on the surface of coatings can be a problem in certain applications. Furthermore, as discussed in the Examples, and confirming what was found by Wei et al, Polym. Chem., 2010, 1, 1430-1433, the slower polymerisation at acidic pH under oxidative conditions produces coatings at least as uniform as those observed for polymerisation under the faster alkaline conditions. The coating prepared at acidic pH under oxidative conditions is more reproducible since the process time at which particulation of polydopamine occurs is prolonged. This is advantageous from a manufacturing perspective.

The amount of oxidant affects the rate of polymerisation and can also influence the amount of particulation, as shown in Examples 1.9 and discussed in Example 1a. In the examples, the amount of dopamine in solution is between 1 g/L to 5 g/L and the amount of APS in solution is between 0.6 g/L and 3 g/L. In one embodiment, particulation appears to be low, for an acceptable rate of reaction, using 1 g/L of dopamine and 0.6 g/L of APS. The polymerisation rate may be increased by increasing the dopamine and/or APS concentration. The concentration of dopamine or analogue may typically be 0.5-10 g/L and the concentration of APS may typically be 0.1-5 g/L.

Polymerisation of dopamine can be performed in aqueous solutions or in aqueous/organic mixtures such as mixtures of water with methanol, ethanol, propanol and/or isopropanol.

The pH of the solution can be controlled with buffer—see, for example, http://www.sigmaaldrich.com/life-science/core-bioreagents/biological-buffers/learning-center/buffer-reference-center.html.

As discussed in Examples 1 and 1a, MES buffer has been found to be suitable. Other possible buffers include ACES, PIPES, MOPSO, Bis-Tris propane, BES, MOPS, TES and HEPES.

The time required to form a polydopamine coating will vary depending on the specific reaction conditions used. For example, the addition of an oxidant may speed up polymerisation, or allow the use of a neutral or even acidic pH. The polydopamine coating is preferably formed within a time period that is feasible for efficient manufacture. For example, the desired polydopamine coverage can be formed within 24 hours, 12 hours, 6 hours, 5 hours, 4 hours, 3 hours, 2 hours, 1 hour or 30 min. As a general principle, the longer the polymerisation time, the thicker the coating of polydopamine formed. However, after a certain period of polymerisation, polydopamine will precipitate out of the solution in particulate form, causing various problems as discussed above. Thus, the optimum time for polymerisation of dopamine is long enough to obtain sufficient coverage of polydopamine, but not so long as to allow uncontrolled particulate polydopamine to be formed in solution. Suitably, polymerisation time is no longer than 24 hours, for example up to 12 hours, 6 hours, 5 hours, 4 hours, 3 hours, 2 hours, 1 hour or 30 min.

Suitably, the thickness of the polydopamine coating is between 5 and 100 nm, for example between 10 and 50 nm.

Preferably the polydopamine coating is formed at room temperature, although the polymerisation can be carried out at higher/lower temperatures.

Detailed methods for forming a polydopamine coating on various substrates are provided in Examples 1.1 to 1.13 and an optimised procedure is provided in Example 1.11.

A possible alternative approach for forming polydopamine using electric charges (voltage) is described in Kang et al. Angewandte Chemie, 2012, vol. 124, pp 1-5.

Radical Initiators Capable of Extracting Hydrogen Atoms from a Surface

According to an embodiment, the polymerisation of components A, B and optionally C and D is initiated by a radical initiator which abstracts hydrogen atoms from the surface of the substrate, to generate surface-bound radicals. Surface-bound radicals are radicals which are bound, or confined to the surface from which the hydrogen atom has been abstracted. The surface-bound radicals then react with at least one of components A, B and optionally C and D to form a copolymer of the relevant components which is covalently bound to the surface.

Preferably the radical initiator is not covalently bound to the surface comprising abstractable hydrogen atoms, either prior to the polymerisation reaction or after.

Suitable type II photoinitiators based on benzophenone include, but are not limited to, benzophenone, benzophenone-3,3'-4,4'-tetracarboxylic dianhydride, 4-benzoylbiphenyl, 4,4'-bis(diethylamino)benzophenone, 4,4'-bis[2-(1-propenyl)phenoxy]benzophenone, 4-(diethylamino)benzophenone, 4,4'-dihydroxybenzophenone, 4-(dimethylamino)benzophenone, 3,4-dimethylbenzophenone, 3-hydroxybenzophenone, 4-hydroxybenzophenone, 2-methylbenzophenone, 3-methylbenzophenone, 4-methylbenzophenone, methyl benzoylformate and Michler's ketone. Other suitable benzophenones are Omnipols from IGM resins.

Suitable type II photoinitiators based on xanthone include, but are not limited to: 9-xanthenone, 1-hydroxy-3,7-dimethoxyxanthone, 1-hydroxy-3,5-dimethoxyxanthone, 1-hydroxy-3,5,6,7-tetramethoxyxanthone, 1-hydroxy-3,5,6,7,8-pentamethoxyxanthone, 1-hydroxy-3,7,8-trimethoxyxanthone and 2-benzoylxanthone.

Suitable type II photoinitiators based on thioxanthone include, but are not limited to: 1-chloro-4-propoxy-9H-thioxanthen-9-one, 2-chlorothioxanthen-9-one, 2,4-diethyl-9H-thioxanthen-9-one, isopropyl-9H-thioxanthen-9-one, 10-methylphenothiazine and thioxanthen-9-one. Other suitable thioxanthones are Omnipols from IGM resins.

Miscellaneous other photoinitiators which may be suitable include, but are not limited to: anthraquinone-2-sulfonic acid sodium salt monohydrate, 2-tert-butylanthraquinone, camphorquinone, diphenyl(2,4,6-trimethylbenzoyl)phosphine oxide, 9,10-phenanthrenequinone and phenylbis(2,4,6-trimethylbenzoyl)phosphine oxide.

Cationic photoinitiators which may be suitable include, but are not limited to: bis(4-tert-butylphenyl)iodonium perfluoro-1-butanesulfonate, bis(4-tert-butylphenyl)iodonium p-toluenesulfonate, bis(4-tert-butylphenyl)iodonium triflate, boc-methoxyphenyldiphenylsulfonium triflate, (4-bromophenyl)diphenylsulfonium triflate, (tert-butoxycarbonylmethoxynaphthyl)-diphenylsulfonium triflate, (4-tert-butylphenyl)diphenylsulfonium triflate, diphenyliodonium 9,10-dimethoxyanthracene-2-sulfonate, diphenyliodonium hexafluorophosphate, diphenyliodonium nitrate, diphenyliodonium perfluoro-1-butanesulfonate, diphenyliodonium p-toluenesulfonate, diphenyliodonium triflate, (4-fluorophenyl)diphenylsulfonium triflate, (4-methoxyphenyl)diphenylsulfonium triflate, 2-(4-methoxystyryl)-4,6-bis(trichloromethyl)-1,3,5-triazine, (4-methylphenyl)diphenylsulfonium triflate, (4-methylthiophenyl)methyl phenyl sulfonium triflate, 1-naphthyl diphenylsulfonium triflate, (4-phenoxyphenyl)diphenylsulfonium triflate, (4-phenylthiophenyl)diphenylsulfonium triflate, triarylsulfonium hexafluoroantimonate salts, mixed 50 wt. % in propylene carbonate, triarylsulfonium hexafluorophosphate salts, mixed 50% in propylene carbonate, triphenylsulfonium perfluoro-1-butanesulfonate, triphenylsulfonium triflate, tris(4-tert-butylphenyl)sulfonium perfluoro-1-butanesulfonate and tris(4-tert-butylphenyl)sulfonium triflate.

In one embodiment, the radical initiator is selected from the group consisting of benzophenone and derivatives thereof and xanthone and derivatives thereof.

Benzophenone

In one embodiment, the initiator is benzophenone. Benzophenone is a Type II photoinitiator and is widely used because of the high quantum efficiency of the hydrogen abstraction/proton transfer, particularly with amines. A representative reaction scheme of photoinitiated polymerisation using benzophenone is illustrated in Scheme 1 below.

Scheme 1

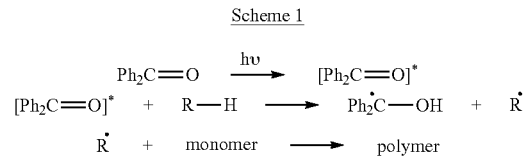

As shown in Scheme 1, when exposed to UV light the triplet excited state of benzophenone is formed, which can abstract a hydrogen from another molecule (a coinitiator) to form a ketyl radical ([Ph$_2$C.—OH]) and a coinitiator radical (R.). Ketyl radicals are not usually very reactive toward vinyl (or unsaturated) monomers due to steric hindrance and delocalisation of the unpaired electron. Therefore, the coinitiator radical will usually initiate polymerisation. In the context of the present invention, R—H represents the substrate having a surface comprising abstractable hydrogen atoms. Thus, benzophenone in its triplet excited state abstracts hydrogen atoms from said surface, forming surface bound radicals on the surface of the substrate. These surface bound radicals then react with at least one of components A, B and optionally C and/or D ("monomer" in Scheme 1) to form a copolymer of components A, B and optionally C and/or D, which is covalently bound to the surface of the substrate ("polymer" in Scheme 1). The representation of benzophenone as a radical initiator shown in Scheme 1 is equally applicable to other radical initiators. Preferably, the radical initiator is a Type II initiator.

In the method of the invention, a hydrogen atom is abstracted from the surface of the substrate to be coated thereby generating a surface bound radical. This radical then reacts with at least one of components A, B, C (if present) and D (if present) to form a covalent point of attachment between the surface and the coating. As such, the amount of radical initiator present in the polymerisation solution can impact on the amount of the covalent bonds between the surface and the coating an overall coverage, and consequently can impact on the durability and lubricity of the final hydrophilic coating.

As described in Example 2, an experiment was conducted to measure the absorbance of various concentrations of benzophenone in ethanol. As discussed in detail in Example 2, the inventors found that the concentration of benzophenone is preferably at least 1 mmol/L in order for the benzophenone to effectively express its hydrogen abstraction properties. The concentrations were determined in solution. The actual concentration of benzophenone, prior to curing, at surface after evaporation of solvent is believed to be higher than 1 mmol/L.

However, it does not follow that iterative increases in the amount of benzophenone in the polymerisation solution will continually enhance the properties of the final hydrophilic coating. Benzophenone is very hydrophobic due to its two aromatic rings and shows poor solubility in water. If the concentration of benzophenone is too high this will lead to side reactions such as radical-radical terminations, including the reaction of the interim benzophenone radical with surface bound radical, resulting in benzhydrol being covalently bonded to the surface of the substrate. This leads to hydrophobic regions on the surface of the final coating, reducing its hydrophilic character (via reducing its ability to absorb water) and its lubricity. An additional disadvantage of using high concentrations of benzophenone is the increased amount of low molecular weight extractables. Thus, the upper limit of benzophenone in the polymerisation mixture is suitably about 0.5-5 wt. %. In one embodiment, the concentration of benzophenone is 0.1-100 mM.

Figure 4:
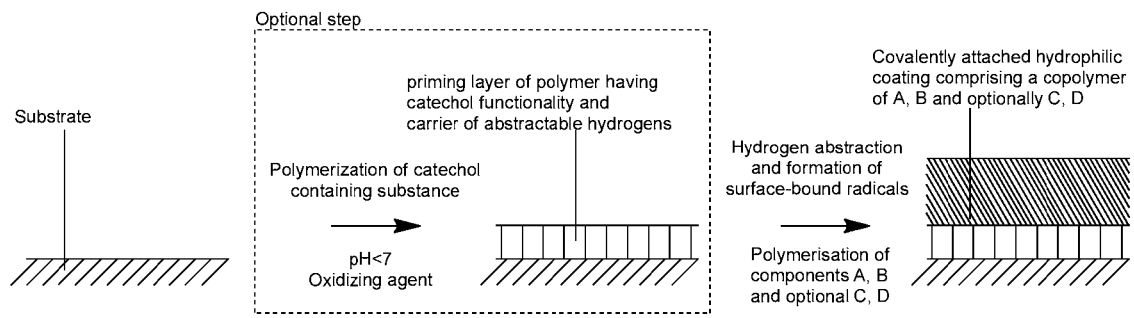
FIG. 4—shows a schematic representation of an embodiment of the invention.

Aspects of this embodiment of the invention are shown schematically in FIG. 4.

Substrates coated with coatings of the invention according to this embodiment were prepared according to the methods described in the Examples.

Embodiment (ii)

In a second embodiment, reactive groups on the surface of the substrate react with at least one of components A and B and optional components C and D to covalently bind the copolymer to the surface in a process initiated by free radicals formed in a liquid phase in contact with the surface.

Figure 2:
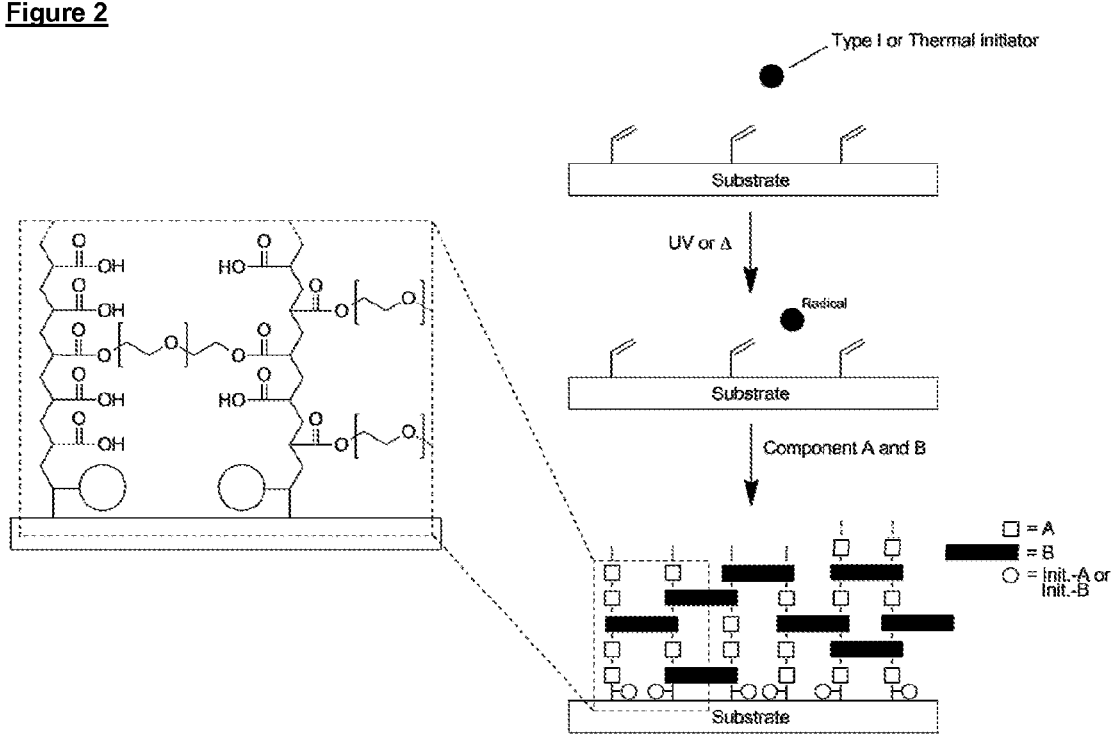

As illustrated in FIG. 2, in this embodiment polymerisation is initiated between polymerisable functional groups on the surface of the substrate and alkene and/or alkyne groups on components A, B and C (if present) and functional groups of component D (if present), resulting in the copolymer of components A, B and optionally C and/or D being covalently attached to the surface of the substrate (FIG. 2 illustrates only alkene groups on the surface of the substrate, and components A and B). In effect, the polymerisable functional groups on the surface of the substrate act as anchoring groups for covalent attachment of the copolymer. Suitable functional groups on the surface of the substrate include alkene, alkyne and thiol groups.

Thus, in another embodiment, the present invention provides a method of forming a hydrophilic coating which is covalently attached to the surface of a substrate, the substrate having a surface comprising polymerisable functional groups, wherein said method comprises the steps of:
(a) contacting the surface with a liquid phase mixture comprising components A and B, optional component C, optional component D and a radical initiator; said radical initiator being capable of generating radicals in the liquid phase, wherein
component A comprises and suitably consists of one or more $C_2$-$C_{16}$ hydrophilic monomers each bearing one or more alkene and/or alkyne groups;
component B comprises and suitably consists of one or more hydrophilic polymers each bearing two or more alkene and/or alkyne groups;
component C, if present, comprises and suitably consists of one or more beneficial agents each bearing one or more (e.g. one) alkene or alkyne groups; and
component D, if present, comprises and suitably consists of one or more low molecular weight cross-linking agents each bearing two or more functional groups independently selected from, thiol, alkene and alkyne groups; and
(b) initiating radical polymerisation involving the alkene and/or alkyne groups of components A, B and C (if present), involving the polymerisable functional groups of the surface of the substrate and involving the functional groups of component D (if present) in order to form a cross-linked copolymer of component A, component B, and optional components C and D; wherein said copolymer is covalently linked to the surface; and
(c) optionally incorporating into the hydrophilic coating a component E which comprises and suitably consists of one or more beneficial agents, wherein component E does not form a copolymer with components A, B, C (if present) and D (if present).

As discussed above, the requirement for abstractable hydrogen atoms at the surface is avoided when the surface includes groups which can act as anchoring groups for covalent attachment of the copolymer. For example, surfaces can include alkene and/or alkyne or thiol groups which can take part in the polymerisation reaction. In an embodiment, the surface is a polydopamine surface in which the polydopamine is functionalised with alkene and/or alkyne groups or thiol groups. Such a polydopamine surface can be prepared by polymerisation of dopamine and dopamine analogues including at least a proportion of an alkene and/or alkyne or thiol group functionalised dopamine (or analogue). Suitably, a synthetic dopamine analogue is formed by functionalising the primary amine of dopamine.

Example dopamine analogues of this sort are illustrated below:

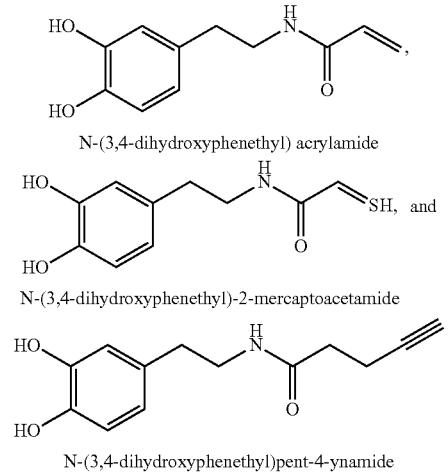

N-(3,4-dihydroxyphenethyl) acrylamide

N-(3,4-dihydroxyphenethyl)-2-mercaptoacetamide

N-(3,4-dihydroxyphenethyl)pent-4-ynamide

Such dopamine analogues can be polymerised using the methods for preparing a polydopamine coating described above for embodiment (ii).

Radical Initiators Capable of Generating Radicals in the Liquid Phase

Radical initiators capable of generating radicals in the liquid phase include photoinitiators (Type I and Type II radical initiators) and thermal initiators.

Examples of Type I radical initiators include photoinitiators based on benzil, benzoin and acetophenone.

Photoinitiators based on benzil and benzoin include, but are not limited to: benzoin, benzoin ethyl ether, benzoin methyl ether, 4,4'-dimethoxybenzoin and 4,4'-dimethylbenzil.

Photoinitiators based on acetophenone include, but are not limited to: 2-benzyl-2-(dimethylamino)-4'-morpholinobutyrophenone, 3,6-bis(2-methyl-2-morpholinopropionyl)-9-octylcarbazole, 4'-tert-butyl-2',6'-dimethylacetophenone, 2,2-diethoxyacetophenone, 2,2-dimethoxy-2-phenylacetophenone, diphenyl(2,4,6-trimethylbenzoyl)

phosphine oxide/2-hydroxy-2-methylpropiophenone, 4'-ethoxyacetophenone, 3'-hydroxyacetophenone, 4'-hydroxyacetophenone, 1-hydroxycyclohexyl phenyl ketone, 2-hydroxy-4'-(2-hydroxyethoxy)-2-methylpropiophenone, 2-hydroxy-2-methylpropiophenone, 2-methyl-4'-(methylthio)-2-morpholinopropiophenone and 4'-phenoxyacetophenone.

Thermal initiators may also be used to initiate radical polymerisation of components A and B and optional components C and D. Thermal initiators undergo homolytic cleavage upon heating to generate free radicals which start the polymerisation process. Ideally a thermal initiator should be relatively stable at room temperature but should decompose rapidly enough at the polymerization temperature to ensure a viable reaction rate. The use of a thermal initiator rather than a photoinitiator can be preferred depending on the substrate to be coated. Substrates such as tubing have inner surfaces which may prove difficult or indeed impossible to expose to visible or UV light. Using a thermal initiator can be more practical in this situation because heat can be evenly distributed to all parts of the substrate.

Examples of thermal initiators include tert-amyl peroxybenzoate, 4,4-azobis(4-cyanovaleric acid), 1,1'-azobis(cyclohexanecarbonitrile), 2,2'-azobisisobutyronitrile (AIBN), benzoyl peroxide 2,2,2-bis(tert-butylperoxy)butane, 1,1-bis(tert-butylperoxy)cyclohexane, 2,5-bis(tert-butylperoxy)-2,5-dimethylhexane, 2,5-bis(tert-butylperoxy)-2,5-dimethyl-3-hexyne, bis(1-(tert-butylperoxy)-1-methylethyl)benzene, 1,1-bis(tert-butylperoxy)-3,3,5-trimethylcyclohexane, tert-butyl hydroperoxide, tert-butyl peracetate, tert-butyl peroxide, tert-butyl peroxybenzoate; tert-butylperoxy isopropyl carbonate, cumene hydroperoxide, cyclohexanone peroxide, dicumyl peroxide, lauroyl peroxide, 2,4-pentanedione peroxide, peracetic acid and potassium persulfate.

Other Embodiments

In a further embodiment, the covalent attachment between the surface of the substrate and the hydrophilic coating is formed via polymerisation involving both embodiments (i) and (ii), for example when the surface of the substrate comprises both abstractable hydrogen atoms and reactive functional groups.

In both embodiments (i) and (ii), the copolymer formed by polymerisation of components A, B and optionally C and D is a random copolymer, whereby the probability of finding a given type of component at a particular point in the polymer chain is equal to the mole fraction of that component in the polymerisation solution.

In one embodiment, the surface of the substrate comprises both abstractable hydrogen atoms and reactive groups which can react with reactive groups of the components in the polymerisation solution. In this embodiment, the choice of radical initiator will dictate the initiation pathway which leads to covalent attachment of the hydrophilic coating to the surface of the substrate. Thus, if a Type II initiator is selected, the covalent attachment will be formed as described for embodiment (i). If a Type I or thermal initiator is selected, the covalent attachment will be formed as described for embodiment (ii). If both a Type II initiator and a Type I or thermal initiator are selected, the covalent attachment will be formed via mixture of the processes described in embodiments (i) and (ii).

Further Aspects of the Method of the Invention

Prior to coating, the surface of the substrate can be cleaned or pretreated in order to improve adhesion to the polymer comprising abstractable hydrogen atoms, or adhesion to the coating optionally comprising the beneficial agent. Prior cleaning or pretreatment of the surface may also improve the uniformity of the coating of either.

Suitable cleaning agents or pre-treatment agents include solvents as ethanol or isopropanol (IPA), solutions with high pH such as solutions comprising a mixture of an alcohol and an aqueous solution of a hydroxide compound (e.g. sodium hydroxide), sodium hydroxide solution per se, solutions containing tetramethyl ammonium hydroxide (TMAH), basic Piranha (ammonia and hydrogen peroxide), acidic Piranha (a mixture of sulfuric acid and hydrogen peroxide), and other oxidizing agents including sulfuric acid and potassium permanganate or different types of peroxysulfuric acid or peroxydisulfuric acid solutions (also as ammonium, sodium, and potassium salts e g ammonium persulfate), or combinations thereof.

Two specific pretreatment methods—Methods A and Method B—are described in the General Procedures. Method A involves treating the substrate to be coated with IPA, while in Method B the substrate is treated with IPA then a solution of APS. As discussed in Example 1a, pretreatment Method B produced a more uniform coating of polydopamine that when Method A was used. Thus, in one embodiment, prior to forming the surface coating of polydopamine the surface of the substrate is pretreated with an oxidant. In another embodiment, prior to forming the surface coating of polydopamine the surface of the substrate is treated with IPA and an oxidant. In a further embodiment, prior to forming the surface coating of polydopamine, the surface to be coated is pretreated with IPA and ammonium persulfate.

When the substrate is coated with a surface priming coating of a polymer comprising abstractable hydrogen atoms, the alignment of the substrate during this priming step can influence the amount of particulation that is observed on the surface of the substrate. When the surface priming coating of a polymer comprising abstractable hydrogen atoms is polydopamine, the present inventors have observed that a horizontal alignment of the substrate during priming, will lead to deposition (via sedimentation) and adherence of polydopamine particles/aggregates formed in the bulk solution. Extensive rinsing is necessary to remove particles/aggregates which are known to have a detrimental effect. A vertical alignment of the substrates is preferred in the priming step to minimize adherence of polydopamine particles/aggregates formed in the bulk solution. The vertical alignment approach does not require the same extensive rinsing since a lower number of aggregates/particles will be present on the primed substrate.

Properties of the Hydrophilic Coating

The lubricity of coatings can be measured using the Lubricity Test as described in the General Procedures and Example 3b.

In an embodiment the hydrophilic coating is lubricious, for example the coating has a lubricity of <100 g e.g. <50 g e.g. <15 g using the Lubricity Test.

More generally, the coating may have a lubricity of <200 g using the Lubricity Test. An acceptable lubricity can be of a higher value when the coating contains a beneficial agent which confers a property other than lubricity (e.g. in case the beneficial agent is a pharmacologic agent).

The durability of coatings can be measured using the Durability Test as described in the General Procedures and Example 3b. In one embodiment, the coating has durability of <50 g e.g. <25 g e.g. <15 g using the Durability Test.

As illustrated by the examples, the coating of the present invention was applied to PEBAX and stainless steel shafts and all were found to have good durability and lubricity.

Without wishing to be bound by theory, the present inventors believe that the good durability of the coating of the invention is a result of the covalent linkages between the copolymer of monomer components A and B and optionally C and D, and the surface of the substrate. In an embodiment, said covalent linkages are formed by the reaction of surface bound radicals (on the surface of the substrate) with monomer components A and B and optionally C and D.

In one embodiment, the coating includes heparin and has a heparin density of >0.1 µg/cm$^2$ e.g. >0.5 µg/cm$^2$ in the Heparin Density Evaluation Test. In one embodiment, the coating is anti-thrombogenic and has a value of >70% remaining platelets in the Blood Contact Evaluation Test.

In another embodiment, the coating includes anti-microbial agents and shows an anti-microbial effect when measuring the zone of inhibition up to 15 days.

In an additional embodiment, the coating is biocompatible as measured according to ISO10993-5.

Hydrophilic coatings according to the invention, in at least some embodiments, are expected to have one or more advantages of:
- having low susceptibility to particulation e.g. as measured according to the Particulation Test;
- high durability e.g. as measured using the Durability Test
- having good coating uniformity e.g. as measured using staining techniques and visual inspection;
- high lubricity e.g. as measured using the Lubricity Test or the Wet Glove Test;
- when component C and/or E is present and is an anticoagulant such as heparin, good anti-thrombogenicity e.g. as measured using the Blood Contact Evaluation Test;
- when component C and/or E is present and is an anti-microbial agent, good anti-microbial activity e.g. as measured using the Zone of Inhibition test;
- being stable to sterilisation;
- good biocompatibility and low cytotoxicity e.g. as measured according to ISO10993-5.

Methods according to the invention, in at least some embodiments, are expected to have one or more advantages of:
- obviating the requirement for organic solvent other than solvents listed as Class 3 and Class 2 solvents in the USP chapter describing residual solvents (in particular obviating the requirement for organic solvent other than solvents listed as Class 3) and the extra reaction steps required for the removal of such residual organic solvent;
- wide applicability, as the coating can be applied to the surface of many different substrates.

DEFINITIONS AND ABBREVIATIONS

'$C_1$-$C_8$alkyl' is defined as a straight or branched aliphatic carbon chain containing 1-8 carbon atoms, for example methyl, ethyl, n-propyl, isopropyl, n-butyl, isobutyl, t-butyl, pentyl, isopentyl, hexyl, heptyl and octyl and the corresponding alkylene radicals such as methylene, ethylene, etc.

'$C_2$-$C_8$alkene' is defined as a straight or branched aliphatic carbon chain containing 2-8 carbon atoms and at least one carbon-carbon double bond.

'$C_2$-$C_8$alkyne' is defined as a straight or branched aliphatic carbon chain containing 2-8 carbon atoms and at least one carbon-carbon triple bond.

AA acrylic acid
APS ammonium persulfate
BP benzophenone
DMF dimethylformamide
DMSO dimethyl sulfoxide
d.i. deionised
EDC 1-ethyl-3-[3-dimethylaminopropyl]carbodiimide hydrochloride
EO ethylene oxide
EtOAc ethyl acetate
FTIR Fourier transform infrared spectroscopy
HEMA 2-hydroxyethyl methacrylate
IPA isopropanol
min minute
MES 2-(N-morpholino)ethanesulfonic acid
NHS N-hydroxysuccinimide
PBS phosphate buffered saline
PEG polyethylene glycol
RH relative humidity
TEA triethylamine
TASSF test average steady state force
THF tetrahydrofuran
tris tris(hydroxymethyl)aminomethane
QCM quartz crystal microbalance

EXAMPLES

General Procedures

Chemicals

Dopamine hydrochloride (dopamine), benzophenone, ethanol 96%, isopropanol, chlorhexidine, triethylamine, acryloyl chloride, sodium cyanoborohydride, hydrochloric acid 37%, pyridine, methacrylic acid anhydride, heparin sodium salt, N-(3-dimethylaminopropyl)-N'-ethylcarbodiimide hydrochloride, 2-aminoethyl methacrylate hydrochloride, tetrahydrofuran, 2-(N-morpholino)ethanesulfonic acid sodium salt, phosphate buffered saline, silver carbonate, acrylic acid and dihydroxyl functionalized PEG variants (4 kDa, 8 kDa and 20 kDa) were purchased from Sigma-Aldrich and used as received. Polyethylene glycol (diacrylated PEG) with molecular weight of 10 kDa was purchased from Creative PEG Works and used as received. Diacrylated PEG with molecular weight 8 kDa was synthesized according to Example 7. Tris(hydroxymethyl)aminomethane and ammonium persulfate were purchased from VWR and used as received. Polyethyleneimine was purchased from BASF.

Materials

PVC tubing (i.d. 3 mm) was purchased from Action Technology.

PEBAX shafts (BaSO$_4$ filled, non-filled, pigmented, non-pigmented) were purchased from Arkema Glass slides were purchased from VWR.

QCM gold crystals were purchased from Q-Sense.

Evaluation Methods

The parameter being evaluated by each method is given in parentheses.

Lubricity Test (Lubricity)

Lubricity testing is performed on a Harland FTS5000 friction tester. Prior to the testing, all shafts are submerged in a d.i. water bath set to 37° C. for 1 min to absorb water unless otherwise stated. The lubricity is given as Test Average Steady State Force (TASSF). It is calculated by taking the average of the cycle force for cycle 1-15. The parameters for the pull friction test are; cycles=15, stroke length=1-5 cm (varies in examples), velocity=0.8 cm/s, acceleration=0.2 s, force=300 g and pause=0 s. See Example 3b and Table 2.

Wet Glove Test (Lubricity)

The Wet Glove Test is an alternative way of testing lubricity. A lubricious coating (<100 g in the Lubricity Test) feels slippery using a wet glove after being submerged into water.

Durability Test (Durability)

Durability is calculated by taking the average force of cycles 13, 14 and 15 and subtracting this value with the obtained value with the average force of cycles 3, 4 and 5 when performing the Lubricity Test. Silicone rubber pads with a durometer of 60 are used for the experiments, see Example 3b and Table 2.

Visual Inspection of Samples (Polydopamine Priming Homogeneity and Coverage)

Visual inspection of the samples was carried out to assess the homogeneity of the polydopamine priming layer, i.e. the surface coverage, see Example 3a Visual Inspection of Solutions (Polydopamine Priming Kinetics and Precipitation of Particles)

Visual inspection of the polymerization solutions was carried out to assess colour change of the priming solutions, i.e. the priming kinetics. Visual inspections were also used to assess formation of particles in the polymerization solution, see Example 3a.

Particulation Test (Particulation in Solution)

A model way to evaluate the particulates that a patient may be exposed to during deployment of a medical device is to conduct simulated-use studies with a simulated deployment system. In such a system, devices designed to travel through the bloodstream are subjected to a tortuous path consisting of either a glass or plastic vein that mimics how the device will travel through the patient's vascular system. We included a variety of angles that are representative of clinical usage across a typical catheter length.

After the experiment, filtered deionised water is flushed through the tortuous path to collect particles from the sample. Particles in the collection media can be analyzed by an Accusizer Particle Sizer (780/SIS PSS NICOMP, Santa Barbara, Calif. USA) according to test method described by United States Pharmacopeia (USP) monograph 788 for small volume injectables. The preparation complies (indicated as "Yes") with the test if the average number of particles present in the units tested does not exceed 6000 per container equal to or greater than 10 µm and does not exceed 600 per container equal to or greater than 25 µm, see Example 3b and Table 2.

Particles in the collection media may also be analysed by visual inspection. In this case, fractions of the solution from the tortuous path containing particles are filtered off onto a filter membrane followed by visual inspection of the particles using microscopy techniques. The filter papers are divided into sections. Careful counting of visible particles is performed within one or more representative sections and the total amount of particles is determined by multiplying the particles from that section by the total number of sections.

It should be noted that preparations that do not comply with the USP standard (i.e. are not indicated as a "Yes" in Table 2) can still have utility in applications where the amount of particulation on the surface of the substrate to be coated is not a consideration e.g. for coating certain non-medical substrates or devices or in medical devices where levels of particulation are not subject to regulatory review.

UATR-FTIR Spectroscopy (Coating Composition)

FTIR analyses of coatings were performed on a Perkin Elmer UATR 100S. Each sample was scanned 3*16 times and processed to yield an average spectrum for each coating. The samples were normalized between 1775 $cm^{-1}$ and 1700 $cm^{-1}$ in order to obtain comparable data, see Example 3a and FIG. 7.

Scanning Electron Microscopy with Energy Dispersive X-Ray Spectroscopy (SEM-EDS)
(Surface Particulation and Elemental Composition)

SEM images of appropriate polydopamine-primed samples were captured using a Hitachi TM3000 table top SEM. Quantification of surface elements was performed using EDS Quantax 70 from Bruker, see Example 1a.

Contact Angle Determination (Coating Coverage)

Static water contact angle measurement was performed on a FTA200 instrument manufactured by First Ten Ångstrom. D.i. water (droplet size approximately 10 µl) is deposited on samples using a syringe. A high resolution camera is then used to capture an image of the droplet. The static contact angle (angle between liquid/solid interface and the liquid/air interface) is determined using an image analysis program, see Example 1a.

Staining Techniques (Coating Uniformity)

Coated substrates can be subjected to Toluidine blue stain solution (200 mg/L in water) by immersing in the solution for 2 minutes followed by extensive water rinse. A blue or violet colour is observed on the surface of coatings that contain a net negative charge e.g. polyacrylic acid or heparin functionality, see Example 3a Coated substrates can be subjected to an acidic Ponceau S stain solution (200 mg/L in water) by immersing in the solution for 2 minutes followed by extensive water rinse. A red color is observed on the surface of coatings with a net positive charge, e.g. quaternary nitrogen functionality, see Example 5a.

Tape Testing (Dry State Adhesion)

An adhesive tape type (Sellotape Diamond Ultra Clear) is firmly pressed onto the pieces for 10 s and peeled off. The degree of coating material attached to the tape and remaining on the substrate can be compared to determine the relative adhesion between various coatings of the invention, see Example 1a.

Quartz Crystal Microbalance with Dissipation (QCM-D) (Primer Thickness)

Quartz Crystal Microbalance with dissipation techniques (QCM-D) is used to evaluate the thickness of polydopamine priming layer. Primer thickness is monitored on crystals covered with gold (QSX 301, Q-Sense), see Example 1a.

X-Ray Photoelectron Spectroscopy with Depth Profiling (XPS) (Primer and Coating Composition)

X-ray Photoelectron Spectroscopy (XPS or ESCA) is the most widely used surface characterization technique providing non-destructive chemical analysis of solid materials. Samples are irradiated with mono-energetic X-rays causing photoelectrons to be emitted from the top 1-10 nm of the sample surface. An electron energy analyzer determines the binding energy of the photoelectrons. Qualitative and quantitative analysis of all elements except hydrogen and helium is possible, at detection limits of ~0.1-0.2 atomic percent. Analysis spot sizes range from 10 µm to 1.4 mm. It is also possible to generate surface images of features using elemental and chemical state mapping. Depth profiling is possible using angle-dependent measurements to obtain non-destructive analyses within the top 10 nm of a surface, or throughout the coating depth using destructive analysis such as ion etching.

Zone of Inhibition (ZOI) (Eluting Anti-Microbial Function)

Coated samples are evaluated in a zone of inhibition (ZOI) test which uses agar-plates inoculated with bacteria to test whether the coated samples influence the growth of particular bacteria. If the bacteria are susceptible to a particular sample, an area of clearing surrounds the sample where bacteria are not capable of growing (called a zone of inhibition), see Example 5.6 and Example 5a.

Surface Inhibition (Non Eluting Anti-Microbial Function)

Coated samples from the ZOI test are gently rinsed with buffer. Then the samples are placed on a fresh agar plate (without inoculated bacteria) and the growth of adhered bacteria is evaluated. If the bacteria are susceptible to components in the surface coating, no or a low amount of colonies are observed.

Heparin Density Evaluation Test (Quantitative Heparin Attachment)

Quantification of surface immobilized heparin can be performed essentially as described in Smith R. L. and Gilkerson E (1979), Anal Biochem 98, 478-480, see Examples 5.2-5.4 and Example 5a.

Doxorubicin Staining (Drug Incorporation/Elution)

Drug containing coatings can be prepared by soaking the coating in a solution of the drug. In the case of soaking with doxorubicin, red colouring of the coating indicates that doxorubicin is successfully incorporated into the coating. The drug can be released by subjecting the coating to a 2M NaCl solution. The reduced level of red colour indicates that the doxorubicin is eluted out from the coating. Fluorescence may also be used for detecting the incorporation and subsequent release of doxorubicin, see Example 5.5 and Example 5a.

Blood Contact Evaluation Test (Platelet Loss)

Blood contact evaluation was performed on samples modified with heparin to evaluate the anti-thrombogenic properties. Firstly the catheter was washed with 0.15M saline solution for 15 min to ensure that all loosely bound heparin was rinsed off and a stable coating remains. The washed coatings were placed in heparinized Falcon tubes containing whole blood and left to rotate on a rocking tube roller set to 20 rpm (see Ekdahl K. N., Advances in Experimental Medicine and Biology, 2013, 735, 257-270 for a representative procedure). The platelets from fresh blood and from the blood collected from the tubes were counted in a cell counter to measure the loss of platelets. A great loss in platelets indicates poor performance of the coating, see Examples 5.2-5.4 and Example 5a.

Biocompatibility Evaluation (Cell Cytotoxicity)

$BaSO_4$ filled PEBAX shafts prepared using the method of the invention are cut into appropriate lengths yielding a total surface area of 30 $cm^2$. The same process is carried out on a native $BaSO_4$ filled PEBAX shaft as a reference. The coatings are evaluated using the Minimal Essential Medium (MEM) elution test as described in ISO10993, see Example 3b.

Pretreatment Methods

Method A: IPA Rinse

Substrates were rinsed with IPA for 5 minutes. The substrates were rinsed with d.i. $H_2O$ and dried at room temperature.

Method B: IPA and APS Rinse

Substrates were rinsed with IPA for 5 minutes followed by rinsing using a solution of APS (50 g/L) in d.i. $H_2O$ for 10 minutes. The substrate were rinsed in $H_2O$ and dried at room temperature.

Example 1

Formation of a Surface Priming Coating of a Polymer Comprising Abstractable Hydrogen Atoms on a Substrate In the following Examples, surface priming coatings of polydopamine were formed on various substrates. QCM crystal and PVC tubing substrates were aligned horizontally when subjected to the polymerization solution. All other substrates with aligned vertically. The uniformity, adhesion and other properties of the polydopamine coatings were then analyzed and the results are summarized in Example 1a.

Example 1.1

Preparation of a Surface Priming Coating of Polydopamine at pH 8 on PEBAX Shafts Using Pretreatment Method A PEBAX shafts were pretreated according to method A. The pretreated shafts were submerged in a d.i. water solution of tris buffer (1.21 g/L) and APS (0.6 g/L), and the pH adjusted to 8.0 using HCl (1M). Dopamine (1 g/L) was added to the solution and the polymerization was allowed to proceed for either 15, 30, 60 or 120 minutes. The polydopamine primed shafts were rinsed using EtOH and dried at room temperature before being analyzed.

Example 1.2

Preparation of a Surface Priming Coating of Polydopamine at pH 8 on PEBAX Shafts Using Pretreatment Method B PEBAX shafts were pretreated according to method B. The pretreated shafts were submerged in a d.i. water solution of tris buffer (1.21 g/L) and APS (0.6 g/L), and the pH adjusted to 8.0 using HCl (1M). Dopamine (1 g/L) was added to the solution and the polymerization was allowed to proceed for either 15, 30, 60 or 120 minutes. The polydopamine primed coated shafts were rinsed using EtOH and dried at room temperature before being analyzed.

Example 1.3

Preparation of a Surface Priming Coating of Polydopamine at pH 8 on Glass Slides Using Pretreatment Method A Glass slides were pretreated according to method A. The pretreated slides were submerged in a d.i. water solution of tris buffer (1.21 g/L) and APS (0.6 g/L), and the pH adjusted to 8.0 using HCl (1M). Dopamine (1 g/L) was added to the solution and the polymerization was allowed to proceed for either 15, 30, 60 or 120 minutes. The polydopamine primed slides were rinsed using EtOH and dried at room temperature before being analyzed.

Example 1.4

Preparation of a Surface Priming Coating of Polydopamine at pH 8 on Glass Slides Using Pretreatment Method B Glass slides were pretreated according to method B. The pretreated slides were submerged in a d.i. water solution of tris buffer (1.21 g/L) and APS (0.6 g/L), and the pH adjusted to 8.0 using HCl (1M). Dopamine (1 g/L) was added to the solution and the polymerization was allowed to proceed for either 15, 30, 60 or 120 minutes. The polydopamine primed slides were rinsed using EtOH and dried at room temperature before being analyzed.

Example 1.5

Preparation of a Surface Priming Coating of Polydopamine at pH 8 on PVC Tubing Using Pretreatment Method A

PVC tubing was pretreated according to method A. The pretreated PVC tubing was subjected to a d.i. water solution of tris buffer (1.21 g/L) and APS (0.6 g/L), and the pH adjusted to 8.0 using HCl (1M). Dopamine (1 g/L) was added to the solution and the polymerization was allowed to proceed for either 15, 30, 60 or 120 minutes. The polydopamine primed PVC tubing was rinsed by circulating EtOH though the tubing at a rate of 100 mL/min and dried at room temperature, before being analyzed.

Example 1.6

Preparation of a Surface Priming Coating of Polydopamine at pH 8 on PVC Tubing Using Pretreatment Method B

PVC tubing was pretreated according to method B. The pretreated PVC tubing was subjected to a d.i. water solution of tris buffer (1.21 g/L) and APS (0.6 g/L), and the pH adjusted to 8.0 using HCl (1M). Dopamine (1 g/L) was added to the solution and the polymerization was allowed to proceed for either 15, 30, 60 or 120 minutes. The polydopamine primed PVC tubing was rinsed by circulating EtOH though the tubing at a rate of 100 mL/min and dried at room temperature, before being analyzed.

Example 1.7

Preparation of a Surface Priming Coating of Polydopamine on (QCM) Gold Crystals at pH 8 with No Pretreatment

QCM gold crystals were subjected to a d.i. water solution of pH 8.0 tris buffer (1.21 g/L) containing APS (0.6 g/L) followed by addition of dopamine (1 g/L) and the polymerization was allowed to proceed for 120 minutes.

Example 1.8

Preparation of a Surface Priming Coating of Polydopamine on $BaSO_4$-Filled PEBAX Shafts at pH 7, 6, 5 and 4 Using Pretreatment Method B

$BaSO_4$-filled PEBAX shafts were pretreated according to method B. Tris (1.21 g/L) was added to d.i. water followed by the addition of APS (0.6 g/L). The solution was divided and poured into four separate beakers. The pH for each beaker was adjusted to 7, 6, 5 or 4 using HCl (1M) then the pretreated $BaSO_4$-filled PEBAX shafts were submerged into the solutions followed by the addition of dopamine (1 g/L). The changes in color of the four solutions were monitored over time.

Example 1.9

Preparation of a Surface Priming Coating of Polydopamine on $BaSO_4$-Filled PEBAX Shafts at pH 6 Using Pretreatment Method B

$BaSO_4$-filled PEBAX shafts were pretreated according to method B. Four d.i water solutions containing tris (1.21 g/L) and different amount of dopamine and APS were prepared as follows:

TABLE 1

| Solution No. | dopamine (g/L) | APS (g/L) | dopamine:APS* |
|---|---|---|---|
| 1 | 1 | 0.6 | 1:0.6 |
| 2 | 1 | 3 | 1:3 |
| 3 | 5 | 0.6 | 1:0.12 |
| 4 | 5 | 3 | 1:0.6 |

*weight ratio

The solutions were adjusted to pH 6 then the pretreated $BaSO_4$-filled PEBAX shafts were submerged into the solutions followed by addition of the appropriate amount dopamine. Each solution was analyzed visually for colour change and particulation.

Example 1.10

Preparation of a Surface Priming Coating of Polydopamine on $BaSO_4$-Filled PEBAX Shafts at pH 6.9 Using Pretreatment Method B

$BaSO_4$-filled PEBAX shafts were pretreated according to method B. The pretreated shafts were submerged in a d.i. water solution of tris buffer (1.21 g/L) and APS (0.6 g/L), and the pH adjusted to 6.9 using HCl (1M). Dopamine (1 g/L) was added to the solution and the polymerization was allowed to proceed for 4 hours. During the polymerization, the pH of the solution was observed to decrease over time, therefore NaOH was added sequentially in sufficient amounts to maintain neutral or slightly acidic pH. The polydopamine primed coated shafts were rinsed using EtOH and dried at room temperature before being analyzed.

Example 1.11

Preparation of a Surface Priming Coating of Polydopamine on $BaSO_4$-Filled PEBAX Shafts at pH 6 in MES Buffer Using Pretreatment Method B

$BaSO_4$-filled PEBAX shafts were pretreated according to method B. The pretreated shafts were submerged in a d.i water solution of MES buffer (9.76 g/L) and NaCl (8.76 g/L), and the pH adjusted to 6.0 using HCl (1M). Dopamine (1 g/L) was added to the solution and the shafts were withdrawn from the solution after 5 hours. The polydopamine coated shafts were rinsed using EtOH and dried at room temperature before being analyzed. The polymerization in bulk was allowed to proceed for 24 hours.

Example 1.12

Preparation of a Surface Priming Coating of Polydopamine on Stainless Steel Coupons at pH 6.0 in a Mixture of IPA and Water Using Pretreatment Method B

MES (4.88 g/L) and NaCl (4.38 g/L) were dissolved in d.i. water and the pH was set to 6.0 followed by doubling of the volume by the addition of IPA. The mixture was allowed to stir for 2 minutes prior to the addition of dopamine (0.5 g/L). Stainless steel coupons pretreated according to method B was submerged into the water/IPA buffer solution and the reaction was allowed to proceed for 4 hours where after the coupons were rinsed with EtOH and dried at room temperature before being analyzed.

Example 1.13

Preparation of a Surface Priming Coating of Polydopamine on Titanium Coupons at pH 6.0 in a Mixture of IPA and Water Using Pretreatment Method B MES (4.88 g/L) and NaCl (4.38 g/L) were dissolved in d.i. water and the pH was set to 6.0 followed by doubling of the volume by the addition of IPA. The mixture was allowed to stir for 2 minutes prior to the addition of dopamine (0.5 g/L). Titanium coupons pretreated according to method B was submerged into the water/IPA buffer solution and the reaction was allowed to proceed for 4 hours where after the coupons were rinsed with EtOH and dried at room temperature before being analyzed.

Example 1.14

Preparation of Polydopamine Primer for Hydrogen Abstraction on PTFE Coupons in a Mixture of IPA and Water PTFE may be primed with polydopamine essentially using the procedure described in Example 1.12.

Example 1a

Evaluation of Polydopamine Priming Coatings of Examples 1.1 to 1.13

Coating uniformity of the polydopamine coatings was assessed by visual inspection and/or contact angle measurements; and adhesion was assessed using tape testing, using the procedures described in the General Procedures section. The amount of precipitation observed in the polymerization solution was assessed visually or with SEM-EDS techniques. In all cases the polymerization reaction was stopped by removing the substrate from the solution.

Visual Inspection of Solutions and Substrates

All solutions were initially colourless before the addition of dopamine Once the dopamine was added a colour change was observed, indicating that polymerization of the dopamine to form polydopamine was taking place. In general, a colour change of colourless→yellow→orange→brown was observed as polymerization proceeded.

For all of examples 1.1-1.13 a colour change was observed, indicating that polymerization to form polydopamine occurred. A visual assessment of the rate of colour change of the polymerization solution from colourless→yellow→orange→brown was used to compare the rate of polymerization under different reaction conditions (i.e. to assess the priming kinetics). Additionally, the resulting brown colour tone on the surface of the substrate after the polymerization reaction was indicative of the amount and/or uniformity of the priming coating of polydopamine A less brown colour tone of the substrate is indicative for a thinner polydopamine coating and a more intense brown colour tone is indicative for a thicker polydopamine coating.

In the inventors' experience, a darker colour is linked with greater precipitation.

Effect of pH on Polymerization

In Example 1.8 the effect of the pH of the solution on the rate of polymerization was assessed by visual inspection of the four solutions of pH 7, 6, 5 and 4. The largest colour change, i.e. fastest conversion of dopamine into its oxidative state, was observed for the beaker that contained the solution set to pH 7. The beaker containing the pH 4 solution changed its colour the least and showed the slowest reaction kinetics. The solution in the pH 7 beaker shifted from colourless to orange after one hour whereas the solution in the pH 4 beaker became slightly yellowish after one hour. The colour for the pH 5 and pH 6 solutions was more orange than the pH 4 solution but less than the pH 7 solution. Leaving the solutions for 6 hours resulted in shifts to orange coloured solutions for all pHs with the pH 7 solution being the strongest.

Effect of Buffering on Polymerization

During polymerization of dopamine in Example 1.10, the pH of the solution is observed to decrease. In order to compensate for the decreased pH, NaOH was added to keep the pH constant throughout the polymerization process. No formation of polydopamine particles/aggregates were seen at the end of the polymerization. The shafts primed according to Example 1.10 were uniform as indicated by visual inspection.

As described in Example 1.11, when MES buffer was added to the dopamine solution the pH of the solution was maintained throughout the polymerization without the addition of NaOH, indicating the efficient buffering of the MES buffer. Visual inspection of the dopamine solution indicated that a continuous polymerization occurred. No formation of polydopamine particles/aggregates were seen at the end of the polymerization. The shafts were uniformly primed with polydopamine based on visual inspection.

Evaluation of Solvent Mixtures on Polymerization

In Example 1.12 and 1.13, stainless steel and titanium coupons were primed with polydopamine using a solvent mixture of water and IPA. The polymerization kinetics was not significantly affected by the addition of IPA as measured using the visual inspection test on the solution. The polydopamine primed coupons showed uniform coverage based on visual inspection.

Evaluation of the Adhesion Properties of Polydopamine Coatings

PEBAX shaft and glass slides primed according to Example 1.1-1.4 were subjected to a tape test as described in the general procedures. The adhesive tape was applied to the primed substrates followed by removal of it using a peel-off angle of 90°. It was found that all samples performed well and showed no visual negative effect, in terms of delamination or poor adhesion to the substrate, upon removal of the adhesive tape.

Evaluation of the Thickness of the Polydopamine Coating

A Quartz crystal microbalance coated with gold was mounted in a QSense QCM-D followed by priming of the gold surface according to Example 1.7. The priming solution was allowed to pass over the crystal while monitoring the wet priming thickness over time, as described in the General procedures. It was found that the thickness of the polydopamine layer did not increase after 40 minutes, having a final wet thickness of polydopamine of about 20 nm. The polydopamine-coated gold crystal was dried overnight in a dessicator and the thickness measured again (dry thickness). The dry thickness was found to be in agreement with the calculated wet thickness of about 20 nm.

Evaluation of Chemical Composition and Thickness of the Polydopamine Coating.

The chemical composition and thickness of the polydopamine coating may be determined using XPS depth profiling techniques.

Evaluation of Particulation

During the preparation of a polydopamine-coated PEBAX shaft according to Example 1.11 (which was prepared at pH 6), filter paper capturing of particles from the polydopamine solution were collected after 5 hours and 24 hours. It was found by SEM-EDS and visual inspection techniques, that the amount and size of polydopamine particles formed after 24 hours was significantly higher than after 5 hours. In the case of the 5 hour sample, no visible particles could be seen on the filter paper only a slight color change of the fibers of the filter paper due to absorption of the colored dopamine solution into the filter fibers.

From experience in evaluating the extent of particulation in different samples, the inventors concluded that the extent of particulation increases with greater extent of polymerization (which is apparent from greater colour change).

Effect of Oxidant (APS) and Dopamine on Polymerisation

In Example 1.9 (see Table 1) the effect of the amount of dopamine and APS in the priming solution (pH 6) was assessed. Solution labelled No. 1 contains 1 g/L dopamine and 0.6 g/L of APS, solution labelled No. 2 contains 1 g/L dopamine and 3 g/L of APS, solution labelled No. 3 contains 5 g/L dopamine and 0.6 g/L of APS and solution labelled No. 4 contains 5 g/L dopamine and 3 g/L of APS. Solution No. 4 changed its colour fastest due to highest concentration of dopamine and APS and was dark brown colour after 6 hours. Further, it was found that a faster colour change, when keeping the dopamine concentration constant, was observed for the solutions with higher amount of APS (No. 1→No. 2 and No. 3→No. 4). This indicates that the reaction kinetics can be increased by the addition of oxidizing agent (APS). It was also found that a faster colour change, when keeping the APS concentration constant, was observed for the solutions with higher amount of dopamine (No. 1→No. 3 and No. 2→No. 4). However, fast polymerization kinetics may lead to greater precipitation of polydopamine in the bulk solution. Therefore, control of the polymerization kinetics is crucial in order to ensure that a final product with desired properties is obtained. The substrates submerged into solutions No. 1-4 showed uniform coverage of polydopamine primer, however, the thickness of the priming layer varied for the four different solutions since the colour of the primed substrates varied in intensity. A controlled system, with low formation of particles/aggregates at a given polymerization time, may be obtained if the reaction kinetics are slowed down. i.e. decreasing the amount of dopamine and/or the amount of APS in the solution. Solution No. 1 appears to give the most acceptable rate of reaction with an apparently low rate of particulation (based on the extent of colour change).

Comparison of Pretreatment Methods A and B

Figure 5:
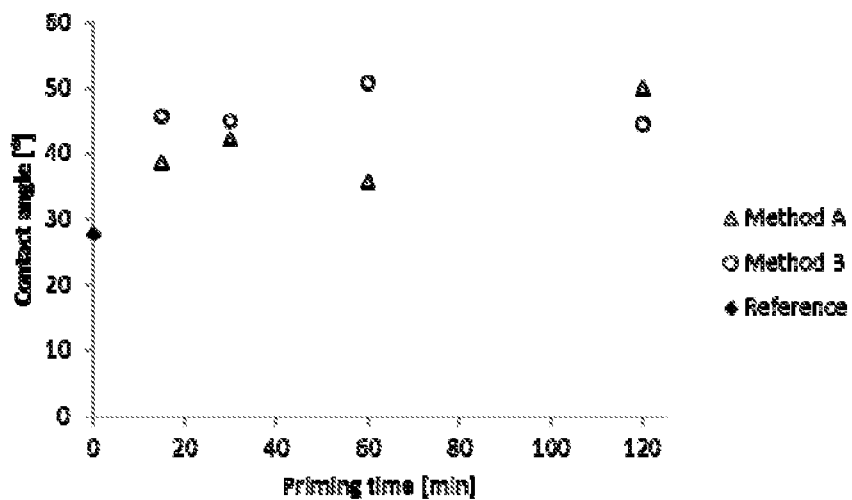
FIG. 5—shows contact angle measurements of a polydopamine priming coating on glass slides which had been pretreated using method A or method B (see Example 1a)

Glass slides with polydopamine coatings prepared according to Examples 1.3 and 1.4 were analyzed using the contact angle measurement procedure outline in the General Procedures. The results for Example 1.3 (pretreatment Method A) and Example 1.4 (pretreatment Method B) are shown in FIG. 5.

A surface with complete polydopamine coverage will have a contact angle of around 50° (Lee et al, Science, 2007, 318, 426). Comparing the contact angles for methods A and B, it is evident that following pretreatment method A, slightly lower static contact angles were observed when compared to the slides that had been pretreated using method B, indicating that following pretreatment B, more complete coverage of polydopamine on the surface of the slide was obtained. Furthermore, slides which had been pretreated using method B reached a steady static contact angle after 15 minutes of dopamine polymerization, compared with slides pretreated using method A, which reached a similar static contact angle after 120 minutes. This indicates that as well as achieving better overall coverage of polydopamine, slides pretreated using method B also achieved the coating more rapidly. The contact angle of an unprimed glass slide is shown as a reference data point in FIG. 5. It is evident that a polydopamine primed glass slide (using either pretreatment method A or method B) has a surface which exhibits a higher contact angle than if the surface was unprimed, demonstrating priming coverage.

Example 2

Figure 6:
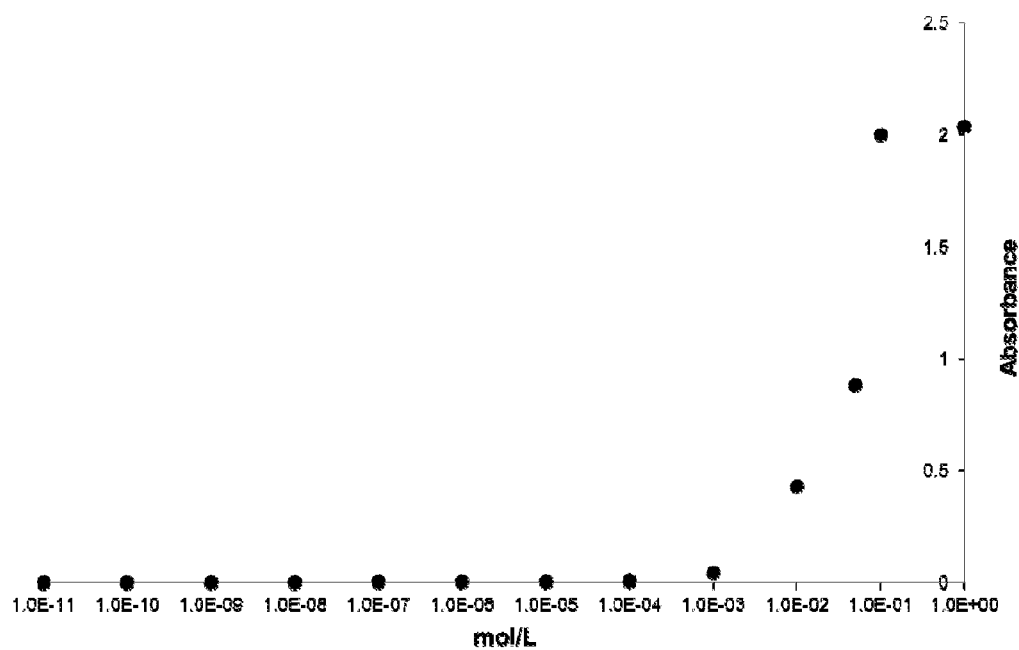
FIG. 6—shows the UV absorbance of benzophenone as a function of concentration (see Example 2)

Determination of the Amount of Benzophenone to be Used in Forming Hydrophilic Coatings of the Invention Benzophenone was dissolved in EtOH at different concentrations ($1.0E^{-11}$ mol/L to 1 mol/L). The UV absorbance of benzophenone was monitored as a function of concentration and the results are illustrated in FIG. 6. It is evident from FIG. 6 that absorbance only appears to take place at concentrations of benzophenone above $1.0E^3$ mol/L (1 mmol/L). Thus, within this invention, it appears that the concentration of benzophenone had to be at least 1 mmol/L and preferably 1-100 mM, in order for the benzophenone to express its hydrogen abstractable properties to form surface bound radicals which react to covalently bind the copolymer of components A, B and C (if present) and D (if present) to the surface.

Example 3

Formation of a Hydrophilic Coating on a Polydopamine-Primed Substrate

In the following Examples, substrates coated with a priming coating of polydopamine prepared according to Example 1 were subjected to a method of the invention to form a hydrophilic coating of the invention. In each case, component A was acrylic acid, component B was a diacrylated PEG polymer and the radical initiator benzophenone (a radical initiator capable of abstracting hydrogen atoms from the surface of the polydopamine). The solvent used was ethanol and in each case the radical polymerization was initiated by UV light. The resulting hydrophilic coatings were analyzed and the results are summarized in Examples 3a and 3b.

Example 3.1

Formation of a Hydrophilic Coating on Polydopamine-Primed PEBAX Shafts Using Benzophenone (1 Wt %) and a Low Intensity Lamp Various solutions of 8 kDa diacrylated PEG polymer (30 mg-1050 mg, see Example 7 for preparation), acrylic acid (300 mg) (mass ratios of 0.1:1-3.5:1), benzophenone (1 wt %) in EtOH (2 mL-6 mL) were prepared. PEBAX shafts prepared according to Example 1.2 were then manually dipped into the solutions before being removed and cured using a 365 nm B-100AP UV-lamp (supplied by UVP) for 10 minutes. The intensity was recorded to ~15 mW/cm² using a sensor and radiometer.

Example 3.2

Formation of a Hydrophilic Coating on Polydopamine-Primed PEBAX Shafts Using Benzophenone (1 Wt %) and a Medium Intensity Lamp Two solutions of containing 10 kDa diacrylated PEG (450 mg and 1350 mg, respectively), acrylic acid (300 mg and 1800 mg, respectively) (mass ratios of 1.5:1 and 0.75:1, respectively), and benzophenone (1 wt %) in EtOH (10.5 mL and 29 mL, respectively) were prepared. PEBAX shafts prepared according to Example 1.2 were then dipped into either solution (dwell time 5 s) before being removed (withdrawal speed 5 cm/s and 2.5 cm/s respectively) and cured using an RDX UV curing system (240-400 nm) (supplied by Harland Medical) for 75 seconds. The intensity was recorded to ~55 mW/cm$^2$ using a sensor and radiometer. The coated shafts were allowed to swell for 10 minutes in a 37° C. PBS solution prior to evaluation.

Example 3.3

Formation of a Hydrophilic Coating on Polydopamine-Primed PEBAX Shafts Using Benzophenone (3 Wt %) and a Medium Intensity Lamp Formulations consisting of 10 kDa diacrylated PEG (360 mg-9.0 g), acrylic acid (3.6 g) (mass ratios of 0.1:1-2.5:1), and benzophenone (3 wt %) in EtOH (24 mL, 36 mL, 42 mL or 48 mL) were prepared. PEBAX shafts prepared according to Example 1.10 were then dipped into the solutions (dwell time 5 s) before being removed (withdrawal speed 5-15 cm/s) and cured using an RDX UV curing system (240-400 nm) (supplied by Harland Medical) for 90 seconds. The intensity was recorded to ~55 mW/cm$^2$ using a sensor and radiometer.

Example 3.4

Formation of a Hydrophilic Coating on Polydopamine-Primed BaSO$_4$-Filled PEBAX Shafts Using Benzophenone (1 Wt %) and a High Intensity Lamp Formulations consisting of 8 kDa diacrylated PEG (75 mg-1.2 g, see Example 7 for preparation), acrylic acid (300 mg) (mass ratios of 0.25:1-4:1) and benzophenone (1 wt %) in EtOH (2 mL-16 mL) were prepared. BaSO$_4$-filled PEBAX shafts prepared according to Example 1.2 were manually dipped into the solutions before being removed and cured using a Fusion Lamp for 6 seconds. The intensity was recorded to ~200 mW/cm$^2$ using a sensor and radiometer. The coated shafts were allowed to swell for 10 minutes in water bath set to 37° C. prior to evaluation.

Example 3.5

Formation of a Hydrophilic Coating on Polydopamine-Primed BaSO$_4$-Filled PEBAX Shafts Using Benzophenone (1 Wt %) and a High Intensity Lamp A formulation consisting of 8 kDa diacrylated PEG (450 mg, see Example 7 for preparation), acrylic acid (300 mg) (mass ratio of 1.5:1) and benzophenone (1 wt %) in EtOH (6 mL) and a formulation consisting of 8 kDa diacrylated PEG (900 mg), acrylic acid (300 mg) (mass ratio of 3:1) and benzophenone (1 wt %) in EtOH (10 mL) were prepared. BaSO$_4$-filled PEBAX shafts prepared according to Example 1.2 were manually dipped into the solutions before being removed and cured for using a Fusion Lamp for 6 seconds. The intensity was recorded to ~200 mW/cm$^2$ using a sensor and radiometer. The coated shafts were allowed to swell for 10 minutes in water bath set to 37° C. prior to evaluation.

Example 3.6

Sterilization and Aging Treatment of a Hydrophilic Coating of the Invention

BaSO$_4$-filled shafts with a hydrophilic coatings prepared according to Example 3.5 were EO sterilized (standard sterilization process used for medical devices), then subjected to 46 days of aging in a climate chamber (RH=75%, 55° C.). The coated shafts were allowed to swell for 10 minutes in water bath set to 37° C. prior to evaluation.

Example 3.7

Formation of a Hydrophilic Coating on Polydopamine Primed Stainless Steel Shafts Using Benzophenone (1 Wt %) and a Low Intensity Lamp Stainless steel shafts were prepared according to Example 1.2 with dopamine polymerization for 30 minutes. A solution of 8 kDa diacrylated PEG polymer (300 mg, see Example 7 for preparation), acrylic acid (100 mg) (mass ratios of 3:1), benzophenone (1 wt %) in EtOH (2 mL) was prepared followed by manually dipping of the stainless steel shafts into the solutions before being cured using a 365 nm B-100AP UV-lamp (supplied by UVP) for 30 minutes. The intensity was recorded to ~15 mW/cm$^2$ using a sensor and radiometer.

Example 3a

Evaluation of the Surface Coverage and Composition of Hydrophilic Coatings of the Invention Surface Coverage Hydrophilic coatings prepared according to any of the procedures under Example 3 were stained with toluidine blue according to the Staining test. For all of the examples it was observed that hydrophilic coatings stain uniformly, verifying that negatively charged groups are present on the surface of the PEBAX shaft (i.e. good surface coverage of the hydrophilic coating).

Coating Composition

Figure 7:
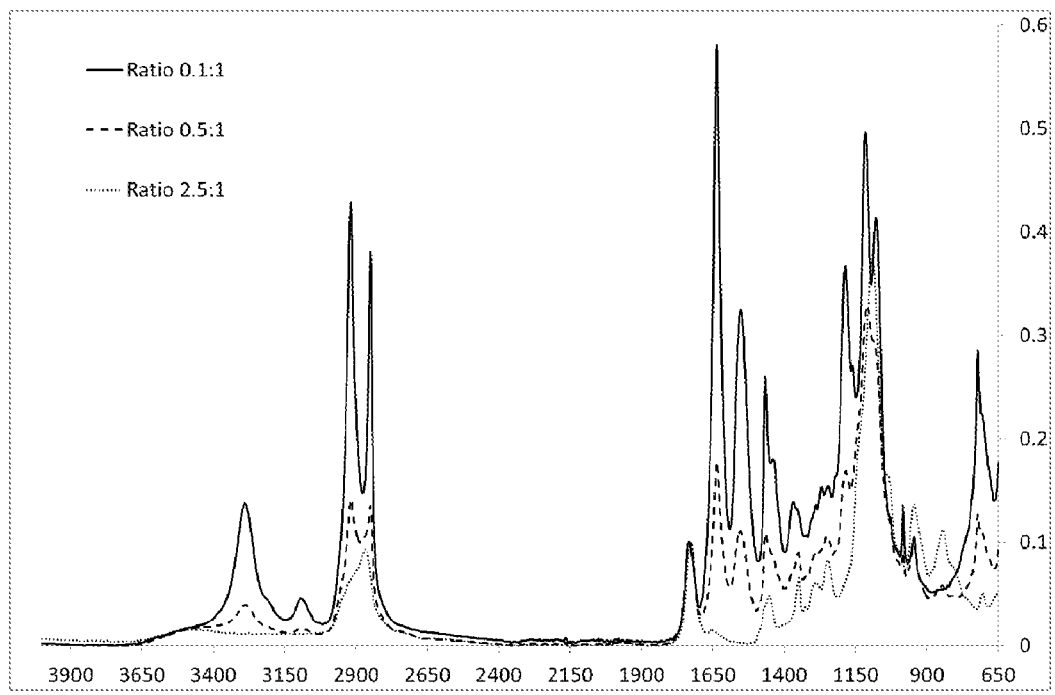
FIG. 7—shows FTIR analysis of the hydrophilic coatings prepared according to Example 3.3

The hydrophilic coatings prepared according Example 3.3 were analysed using FTIR techniques and the spectra are shown in FIG. 7. It was found that distinct peaks associated to ethers (C—O, ~1110 cm$^{-1}$), carbonyls (C=O, ~1730 cm$^{-1}$), and methylenes (C—H, 3000-2800 cm$^{-1}$) could be clearly visualized. Also, signals from N—H (3400-3200 cm$^{-1}$) and amide (NC=O, ~1640 cm$^{-1}$) associated with the substrate could also be visualized; however, these peaks tend to disappear as the coating gets thicker with increased PEG content. The weight ratios of PEG:AA in solution correlates well with their corresponding FTIR coating peaks. To clarify, FTIR analysis of coatings within this invention can be used to determine the weight ratios of PEG:AA of an unknown solution used for preparation of coatings within this invention.

Example 3b

Evaluation of the Physical Properties of the Hydrophilic Coatings of the Invention Hydrophilic coatings of the invention prepared according to Examples 3.1-3.7 were evaluated using the methods described in the general procedures.

The results are summarised in Table 2 below:

TABLE 2

| Example | PEG MW | PEG [mg] | AA [mg] | Ratio w/w PEG:AA | BP [mol/L] | EtOH [mL] | Lubr. [g] | Dura. [g] | Pass USP 788 |
|---|---|---|---|---|---|---|---|---|---|
| Control | | | | | | | | | |
| BaSO$_4$-filled PEBAX (control) | N/A | N/A | N/A | N/A | N/A | N/A | 376.0* | 7.2* | N/T |
| Polydopamine primer (control) | N/A | N/A | N/A | N/A | N/A | N/A | 340.2* | 35.4* | N/T |
| Example 3.1 - 1 wt % benzophenone, low intensity lamp | | | | | | | | | |
| 3.1.1 | 8 kDa | 30 | 300 | 0.1:1 | 0.91E$^{-2}$ | 2 | 14.2* | 2* | N/T |
| 3.1.2 | 8 kDa | 75 | 300 | 0.25:1 | 1.00E$^{-2}$ | 2 | 7.3* | −0.5* | N/T |
| 3.1.3 | 8 kDa | 225 | 300 | 0.75:1 | 0.72E$^{-2}$ | 4 | 7.8* | 7.7* | N/T |
| 3.1.4 | 8 kDa | 450 | 300 | 1.5 | 0.69E$^{-2}$ | 6 | 10.2* | 7.4* | N/T |
| 3.1.5 | 8 kDa | 900 | 300 | 3:1 | 3.29E$^{-2}$ | 2 | 108.6* | −2.5* | N/T |
| 3.1.6 | 8 kDa | 1050 | 300 | 3.5:1 | 3.70E$^{-2}$ | 2 | 31.5* | 35.5* | N/T |
| Example 3.2 - 1 wt % benzophenone, medium intensity lamp | | | | | | | | | |
| 3.2.1 | 10 kDa | 450 | 300 | 1.5:1 | 0.39E$^{-2}$ | 10.5 | 7.0* | −1.0* | N/T |
| 3.2.2 | 10 kDa | 1350 | 1800 | 0.75:1 | 0.60E$^{-2}$ | 29 | 29.0* | −8.0* | N/T |
| Example 3.3 - 3 wt % benzophenone, medium intensity lamp | | | | | | | | | |
| 3.3.1 | 10 kDa | 2700 | 3600 | 0.75:1 | 4.3E$^{-2}$ | 24 | 6.1** | 10.3** | Yes |
| 3.3.2 | 10 kDa | 3600 | 3600 | 1:1 | 4.9E$^{-2}$ | 24 | 8.8** | 11.5** | Yes |
| 3.3.3 | 10 kDa | 5400 | 3600 | 1.5:1 | 6.2E$^{-2}$ | 24 | 6.5** | 5.2** | Yes |
| 3.3.4 | 10 kDa | 7200 | 3600 | 2:1 | 7.4E$^{-2}$ | 24 | 8.2** | −2.4** | Yes |
| 3.3.5 | 10 kDa | 9000 | 3600 | 2.5:1 | 8.6E$^{-2}$ | 24 | 114.9** | 97.8** | No |
| 3.3.6 | 10 kDa | 360 | 3600 | 0.1:1 | 1.8E$^{-2}$ | 36 | 143.4* | −39.7* | N/T |
| 3.3.7 | 10 kDa | 900 | 3600 | 0.25:1 | 2.1E$^{-2}$ | 36 | 77.1* | −31.7* | N/T |
| 3.3.8 | 10 kDa | 1800 | 3600 | 0.5:1 | 2.5E$^{-2}$ | 36 | 17.6** | 0.4** | N/T |
| 3.3.9 | 10 kDa | 2700 | 3600 | 0.75:1 | 2.9E$^{-2}$ | 36 | 3.7** | −0.7** | N/T |
| 3.3.10 | 10 kDa | 3600 | 3600 | 1:1 | 3.3E$^{-2}$ | 36 | 4.7** | 1.2** | N/T |
| 3.3.11 | 10 kDa | 5400 | 3600 | 1.5:1 | 4.1E$^{-2}$ | 36 | 3.6** | 1.2** | N/T |
| 3.3.12 | 10 kDa | 7200 | 3600 | 2:1 | 4.9E$^{-2}$ | 36 | 4.0** | 0.1** | N/T |
| 3.3.13 | 10 kDa | 9000 | 3600 | 2.5:1 | 5.8E$^{-2}$ | 36 | 4.5* | 1.9* | N/T |
| 3.3.14 | 10 kDa | 360 | 3600 | 0.1:1 | 1.6E$^{-2}$ | 42 | 18.8* | −3.0* | N/T |
| 3.3.15 | 10 kDa | 900 | 3600 | 0.25:1 | 1.8E$^{-2}$ | 42 | 14.6* | −4.8* | N/T |
| 3.3.16 | 10 kDa | 1800 | 3600 | 0.5:1 | 2.1E$^{-2}$ | 42 | 5.1** | 7.5** | N/T |
| 3.3.17 | 10 kDa | 2700 | 3600 | 0.75:1 | 2.5E$^{-2}$ | 42 | 2.9** | 1.0** | N/T |
| 3.3.18 | 10 kDa | 3600 | 3600 | 1:1 | 2.8E$^{-2}$ | 42 | 3.2** | 0.9** | N/T |
| 3.3.19 | 10 kDa | 5400 | 3600 | 1.5:1 | 3.5E$^{-2}$ | 42 | 2.8* | 0.7* | N/T |
| 3.3.20 | 10 kDa | 7200 | 3600 | 2:1 | 4.2E$^{-2}$ | 42 | 4.3* | 1.6* | N/T |
| 3.3.21 | 10 kDa | 360 | 3600 | 0.1:1 | 1.4E$^{-2}$ | 48 | 23** | −6.5** | Yes |
| 3.3.22 | 10 kDa | 900 | 3600 | 0.25:1 | 1.5E$^{-2}$ | 48 | 14.7** | 28.0** | Yes |
| 3.3.23 | 10 kDa | 1800 | 3600 | 0.5:1 | 1.9E$^{-2}$ | 48 | 9.7** | 25.0** | Yes |
| 3.3.24 | 10 kDa | 2700 | 3600 | 0.75:1 | 2.2E$^{-2}$ | 48 | 9.2** | 24.2** | Yes |
| 3.3.25 | 10 kDa | 3600 | 3600 | 1:1 | 2.5E$^{-2}$ | 48 | 8.0** | 11.1** | Yes |
| 3.3.26 | 10 kDa | 5400 | 3600 | 1.5:1 | 3.1E$^{-2}$ | 48 | 2.9** | 0.6** | Yes |
| 3.3.27 | 10 kDa | 7200 | 3600 | 2:1 | 3.7E$^{-2}$ | 48 | 5.2** | 3.4** | Yes |
| 3.3.28 | 10 kDa | 9000 | 3600 | 2.5:1 | 4.3E$^{-2}$ | 48 | 3.0** | 0.7** | Yes |
| Example 3.4 - 1 wt % benzophenone, high intensity lamp | | | | | | | | | |
| 3.4.1 | 8 kDa | 75 | 300 | 0.25:1 | 1.02E$^{-2}$ | 2 | 14.5** | 13.2** | N/T |
| 3.4.2 | 8 kDa | 225 | 300 | 0.75:1 | 0.72E$^{-2}$ | 4 | 5.6** | 1.6** | N/T |
| 3.4.3 | 8 kDa | 450 | 300 | 1.5:1 | 0.69E$^{-2}$ | 6 | 8.7** | 0.5** | N/T |
| 3.4.4 | 8 kDa | 900 | 300 | 3:1 | 0.66E$^{-2}$ | 10 | 10.0** | −1.3** | N/T |
| 3.4.5 | 8 kDa | 1200 | 300 | 4:1 | 0.51E$^{-2}$ | 16 | 10.7** | −1.3** | N/T |
| Example 3.5 - 1 wt % benzophenone, high intensity lamp | | | | | | | | | |
| 3.5.1 | 8 kDa | 450 | 300 | 1.5:1 | 0.69E$^{-2}$ | 6 | 8.7** | 0.5** | N/T |
| 3.5.2 | 8 kDa | 900 | 300 | 3:1 | 0.66E$^{-2}$ | 10 | 10.0** | −1.3** | N/T |
| Example 3.6 - 1 wt % benzophenone, high intensity lamp after sterilisation and aging | | | | | | | | | |
| 3.6.1 | 8 kDa | 450 | 300 | 1.5:1 | 0.69E$^{-2}$ | 6 | 9.1** | 0.5** | N/T |
| 3.6.2 | 8 kDa | 900 | 300 | 3:1 | 0.66E$^{-2}$ | 10 | 7.4** | 1.0** | N/T |
| Example 3.7 - 1 wt % benzophenone, low intensity lamp, stainless steel rod | | | | | | | | | |
| 3.7.1 | 8 kDa | 300 | 100 | 3:1 | 1.1E$^{-2}$ | 2 | 6.5* | −2.8* | N/T |

Figure 8:
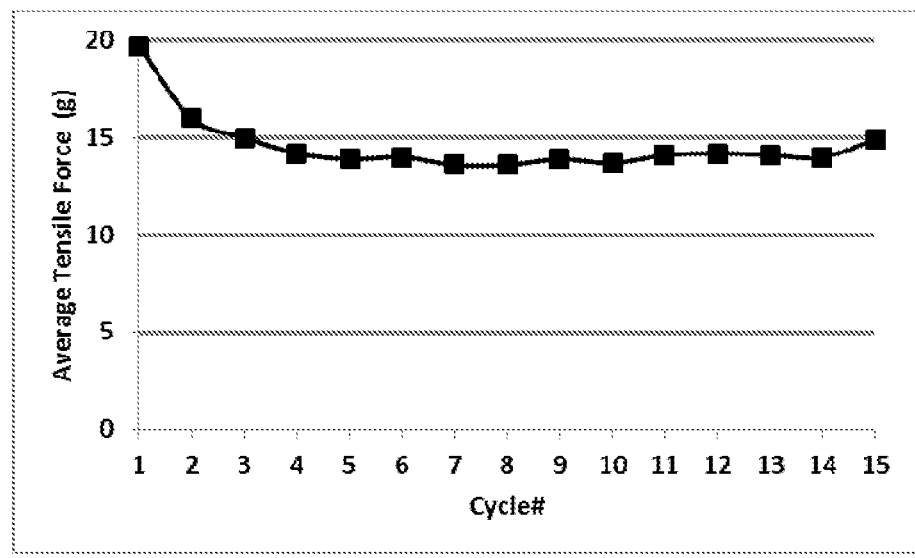
FIG. 8—shows lubricity values over 15 cycles for the hydrophilic coating prepared according to Example 3.3.15
Figure 9:
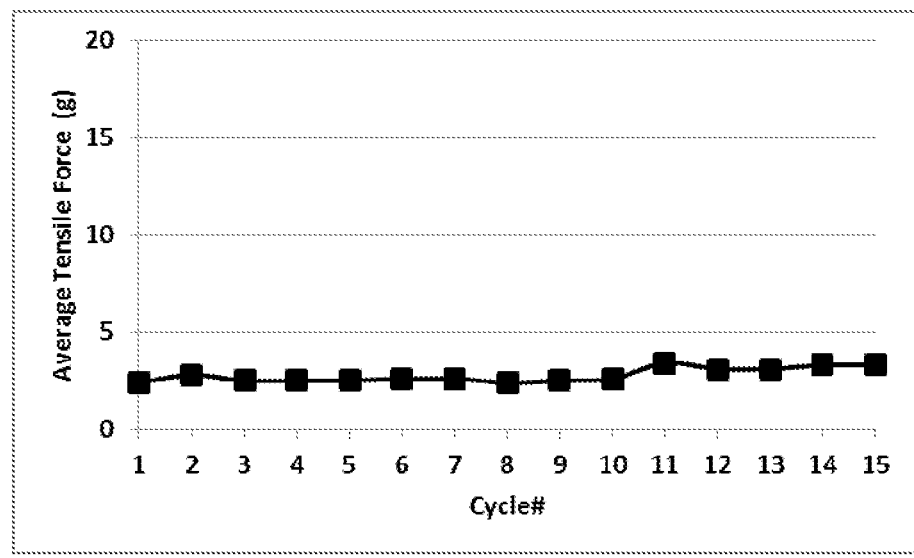
FIG. 9—shows lubricity values over 15 cycles for the hydrophilic coating prepared according to Example 3.3.19

*data based on n = 1 measurements
**data based on n = 2 measurements
N/T = Not tested Lubricity and Durability The lubricity and durability of the coatings were evaluated using the Lubricity and Durability tests described in the general procedures. Table 2 of Example 3a illustrates that, generally, as may reasonably be expected, as the proportion of acrylic acid relative to the acrylate-functionalised PEG is increased, the durability of the coating increases but its lubricity decreases. Conversely, as the proportion of acrylate-functionalised PEG relative to acrylic acid increases, the coating produced is lubricious, but not as durable e.g. Examples 3.3.19 (PEG:AA 1.5:1) and 3.3.15 (PEG:AA 0.25:1) show that as the proportion of PEG (relative to acrylic acid) was decreased six fold, the lubricity of the coating decreased (indicated by a higher lubricity value) and the durability of the coating increased (indicated by a lower durability value). However, a durability value <15 g is considered to be good. The lubricity and durability over 15 cycles for Examples 3.3.15 and 3.3.19 are shown in FIGS. 8 and 9, respectively.

Optimum ratio of acrylate functionalised PEG to acrylic acid was found to be in the range of 2.5:1 and 0.5:1 w/w. The lubricity and durability for coatings with ratios outside this range may also yield coatings with desired properties if prepared from solutions of adequate dilution.

To the inventors' surprise, after sequential cycles in the Lubricity test, the coatings were actually found to increase in lubricity. This is illustrated in Example 3.3.15 of Table 2 (see FIG. 8), from which it is evident that the lubricity of the coating increased, with a lubricity value of 19.7 g in the first cycle and 14.9 g in the $15^{th}$ cycle (wherein a lower lubricity (g) value indicates a more lubricious coating).

The amount of solvent used in the polymerisation solution is crucial for the coating properties in terms of lubricity, durability and particulation and is a parameter that can be varied by the skilled person. If a given ratio of PEG to acrylic acid yields poor coating properties at a certain polymer solution concentration, it may typically express good coating properties if the concentration is altered.

Intensity of the UV Lamp

The inventors have shown that coatings within this invention may be prepared regardless of UV lamp intensity tested. Intensity varying from 15 mW (low intensity) to 200 mW (high intensity) was used.

Amount of Solvent

The concentration of component A and B, and optionally C and D may be varied in the polymerisation solution by adding various amounts of solvent. Generally, an optimum in the amount of solvent will generate a lubricious coating with good durability. Outside the optimum dilution, the copolymer may wear off due to delamination (high concentration) or due to insufficient coating thickness (low concentration).

Particulation

The surface particulation of the coatings was evaluated using the Particulation test described in the general procedures. All of the Examples tested (apart from Example 3.3.5) passed the USP 788 test, indicating that the coatings had demonstrated acceptable levels of particulation. Regarding Example 3.3.5, the higher particulation value was not surprising given the high proportion of PEG in the relatively low solution volume.

Sterilization and Aging

Figure 10:
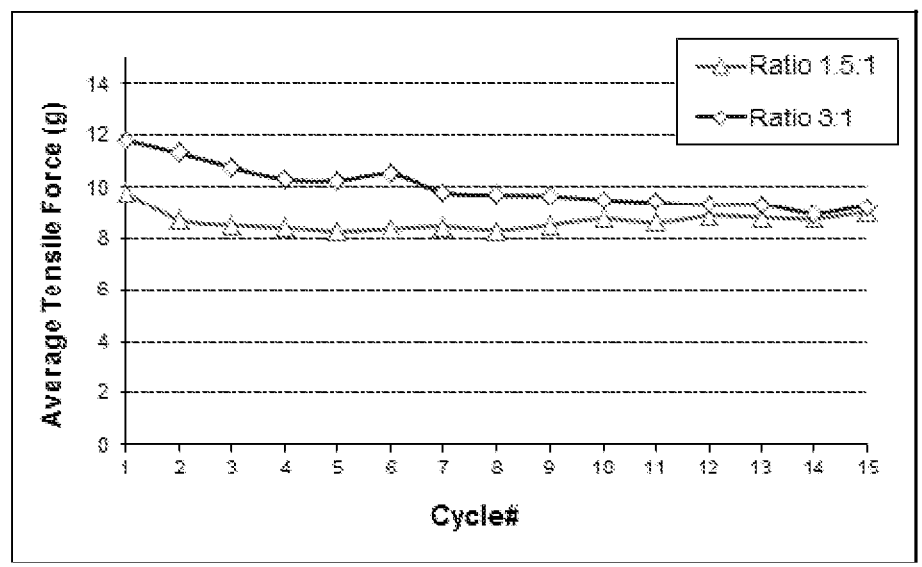
FIG. 10—shows lubricity values over 15 cycles for the hydrophilic coatings prepared according to Example 3.5
Figure 11:
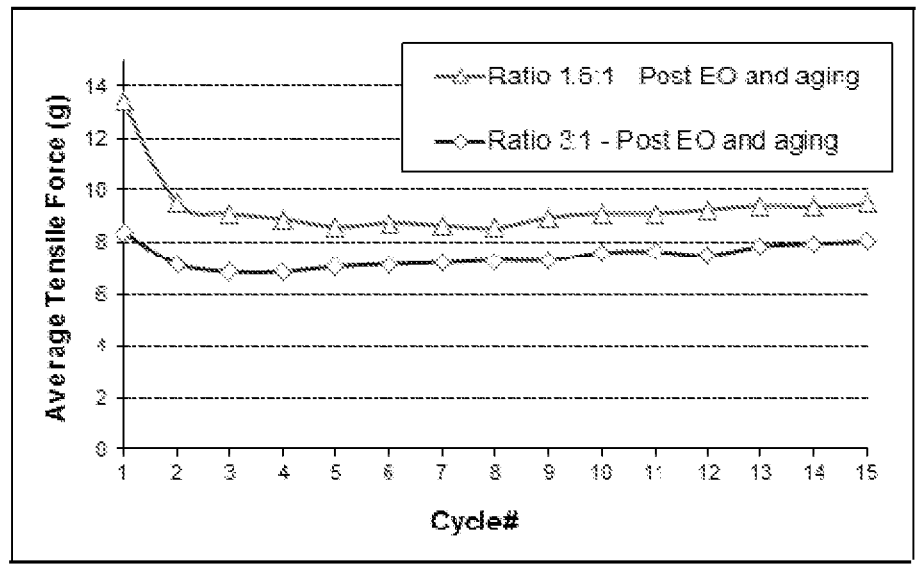
FIG. 11—shows lubricity values over 15 cycles for the hydrophilic coatings prepared according to Example 3.6

FIG. 10 illustrates the lubricity and durability over 15 cycles for Example 3.5 and FIG. 11 illustrates the lubricity over 15 cycles for Example 3.6 (in which the samples of Example 3.5 were sterilized and aged). Comparing of the lubricity and durability values between FIGS. 10 and 11 (and the values in Table 2) it is evident that the sterilization and aging process had little, if any, effect on the lubricity and durability of the hydrophilic coatings.

Biocompatibility

PEBAX shafts with a hydrophilic coating prepared according to Example 3.2 were evaluated in a cytotoxicity tests. The shafts were cut into pieces yielding a total surface area of 30 $cm^2$/sample. The cut shafts were subjected to a minimal essential medium (MEM) elution test according to ISO 10993 part 5. All tested samples were found to be nontoxic in the MEM elution test.

Example 5

Formation of a Hydrophilic Coating Comprising a Beneficial Agent

In the following Examples, a hydrophilic coating comprising a beneficial agent was formed on a substrate already coated with a surface priming coating of polydopamine.

Example 5.1

Formation of a Thrombogenic Coating

A hydrophilic coating prepared according to Example 3.3.18 (ratio 1:1 of PEG:AA, 3 wt % BP, 42 mL EtOH; cured for 90 seconds at 55 $mW/cm^2$) was soaked in a solution of polyethyleneimine in water (0.010 wt %/L, pH 6) for ~1 min followed by an extensive rinse in water.

Example 5.2

Formation of an Anti-Thrombogenic Coating Using Native Heparin

A hydrophilic coating prepared according to Example 3.3.14 was soaked in 50 mL of a solution containing polyethyleneimine (0.01 wt %/L, pH 6) for 10 min prior to rinsing using running d.i. water. Attachment of native heparin was performed essentially as Example 2.11 in US2012/231043 (herein incorporated by reference in its entirety). The coating was thereafter subjected to extensive rinsing using d.i. water followed by a borate-phosphate buffer solution rinse (pH 8).

Example 5.3

Formation of an Anti-Thrombogenic Coating Using Heparin-Polyethyleneimine Conjugate An anti-thrombogenic coating may essentially be prepared by using a heparin-polyethyleneimine conjugate from Example 3.3 in US2012/231043 (herein incorporated by reference in its entirety) and using the procedure described in Example 5.2 from above. Such coating is foreseen to show anti-thrombogenic properties.

Example 5.4

Formation of an Anti-Thrombogenic Coating Using End Point Attachment of Heparin

A hydrophilic coating prepared according to Example 3.3.14 was soaked in 50 mL of a solution containing polyethyleneimine (0.01 wt %/L, pH 7) for 10 min prior to rinsing using running d.i. water. The positively charged coating was thereafter submerged in a water solution (1 L) containing aldehyde functionalised heparin prepared essentially as described in Example 2 of U.S. Pat. No. 4,613,665 (herein incorporated by reference in its entirety) (325 mg) and NaCl (29.2 g) and allowed to react for ~5 minutes prior to addition of NaCNBH$_3$ (5 mL of a 2.5 wt % solution in d.i. water) followed by additional reaction time of ~1 hour. Any ionically bound heparin was removed via extensive rinsing using a borate-phosphate buffer solution (pH 8).

Example 5.5

Formation of a Doxorubicin Eluting Coating

A coating prepared according to Example 3.3.18 was placed in a water solution of doxorubicin (1 mg/25 mL of water) for 2 minutes followed by careful rinsing of the drug loaded coating using water to remove excess prior to visual inspection of the coating. As described in the general procedures Doxorubicin staining (drug incorporation/elution), the red colouring of the coating indicated that doxorubicin was successfully incorporated into the coating.

Example 5.6

Formation of Anti-Microbial Coating

A coating prepared according to Example 3.3.18 was allowed to soak in a solution of silver carbonate and chlorhexidine in EtOH (96%) for 30 seconds. The incorporation of chlorhexidine and silver carbonate was confirmed by evaluating the coating components using SEM-EDS techniques.

Example 5.7

Formation of Anti-Thrombogenic Coating Using Methacrylated Heparin

An anti-thrombogenic coating may be prepared by using the procedure according to Example 3.3 with the addition of methacrylated heparin from Example 6. Such coating is foreseen to show anti-thrombogenic properties.

Example 5.8

Formation of Anti-Thrombogenic Coating Using Methacrylated Heparin

An anti-thrombogenic coating may be prepared by using the procedure according to Example 5.1 followed by admixing of methacrylated heparin from Example 6 and benzophenone. The methacrylated heparin will be covalently attached to the coating upon UV irradiation. Such coating is foreseen to show anti-thrombogenic properties.

Example 5a

Evaluation of Hydrophilic Coatings Comprising a Beneficial Agent

Coating Comprising a Thrombogenic Agent
The polyethyleneimine coating prepared according to Example 5.1 was evaluated, primarily in terms of surface coverage. The coating stained well using Ponceau S indicating the presence of a net positive charge on the surface. The coated shaft was also evaluated for its thrombogenic abilities by placing it in a test tube containing whole blood, donated from a healthy volunteer, which resulted in a significant reduction in clotting time when compared to a control of whole blood not subjected to the thrombogenic coating. The clotting time was decreased by almost 40% (7 minutes until complete thrombus compared to moderate thrombus formed after 11 minutes for the control). This experiment was repeated once to confirm the thrombogenic nature of the coating.

Coating Comprising Native Heparin as Anti-Thrombogenic Agent
The coating prepared according to Example 5.2 was evaluated for its anti-thrombogenic properties. The heparinized shafts were analysed with respect to its surface density of heparin. This heparin density was measured to be 1.4 µg/cm$^2$. The heparin containing coating was subjected to whole blood donated from a healthy donor followed by monitoring potential formation of blood clots. The coated shaft was placed in a Falcon tube containing whole blood and placed on a rocker tube roller for 20 minutes followed by counting of the remaining amount of thrombocytes in the blood. It was found that no blood clots was formed after the 20 minutes, however, a decrease in the amount of remaining platelets was detected (platelet loss=~25%).

Coating Comprising End-Point Attached Heparin as Anti-Thrombogenic Agent
The coating prepared according to Example 5.4 was evaluated for its anti-thrombogenic properties. The heparinized shafts were analysed with respect to its surface density of heparin. This heparin density was measured to be 2.6 µg/cm$^2$. The heparin containing coating was subjected to whole blood donated from a healthy donor followed by monitoring potential formation of blood clots. The coated shaft was placed in a Falcon tube containing whole blood and placed on a rocker tube roller for 20 minutes followed by counting of the remaining amount of thrombocytes in the blood. It was found that no blood clots was formed after the 20 minutes, however, a decrease in the amount of remaining platelets was detected (platelet loss=~25%).

Coating Comprising Doxorubicin as Beneficial Agent
The coating prepared according to Example 5.5 was evaluated for its drug eluting properties. The doxorubicin loaded coating was subjected to 2M NaCl solution to induce release of drug followed by drying in vacuum prior to an additional visual inspection. The reduced level of red colour indicated that the doxorubicin had been eluted out from the coating.

Coating Comprising an Anti-Microbial Agent as Beneficial Agent
Coatings prepared according to Example 5.6 were evaluated for their anti-microbial activity against *Staphylococcus aureus* bacteria. Two replicates of the coating were subjected to *Staphylococcus aureus* bacteria followed by monitoring the zone of inhibition over time. The two replicates showed an anti-microbial effect over 7 and 15 days, respectively. Uncoated PEBAX shaft, polydopamine primed PEBAX shaft and a coated shaft according to Example 3.3.18 (ratio 1:1 of PEG:AA, 3 wt % BP, 42 mL EtOH) were used as controls. None of the controls showed anti-microbial properties longer than 1 day.

Coatings prepared according to Example 5.6 were also evaluated for their anti-microbial activity against *Pseudomonas aeruginosa* bacteria. Two replicates of the coating were subjected to *Pseudomonas aeruginosa* bacteria followed by monitoring the zone of inhibition over time. The two replicates showed an anti-microbial effect over 3 and 4 days, respectively. Uncoated PEBAX shaft, polydopamine primed PEBAX shaft and a coated shaft according to Example 3.3.18

(ratio 1:1 of PEG:AA, 3 wt % BP, 42 mL EtOH) were used as controls. None of the controls showed anti-microbial properties longer than 1 day.

Example 6

Synthesis of End-Point Methacrylated Heparin

Aldehyde functionalised heparin prepared essentially as described in Example 2 of U.S. Pat. No. 4,613,665 (herein incorporated by reference in its entirety) (5.00 g) was dissolved in 15 mL acetate buffer (pH 5) by vigorously stirring. 2-aminoethyl methacrylate hydrochloride (250 mg) was added to the heparin solution followed by 10 mL of a 2.5% sodium cyanoborohydride solution in d.i. water. The reaction scheme is illustrated in Scheme 2. The solution was stirred overnight at room temperature before being transferred to a dialysis bag (MWCO 1,000 Da) and dialyzed for one hour against 3 L of aqueous 1M NaCl. After one hour, the solution of 1M NaCl was replaced by a new solution and the dialysis was continued for an additional one hour. As a last step in the purification sequence, the NaCl solution was replaced by d.i. water and the dialysis was continued overnight. The specific activity of heparin after modification was determined to be >100 IU/mg.

Example 7

Synthesis of 8 kDa Diacrylated PEG Polymer

Dihydroxyl functionalised PEG (8 kDa, 20 g) was dissolved in THF (50 mL), TEA (3.5 mL) and pyridine (15 mL). Acryloyl chloride (1.1 g) was added dropwise to the solution. The reaction scheme is illustrated in Scheme 3. The reaction was allowed to proceed for 4 hours prior to filtering off the precipitated salt and precipitation of the solution into 1 L of diethyl ether. The precipitate (beige/white power) was dried under vacuum overnight. The introduction of acrylic end-groups were verified using FTIR techniques. FTIR revealed an absorption at around 1720 cm$^{-1}$ indicating the incorporation of carbonyl groups (esters) into the PEG chains.

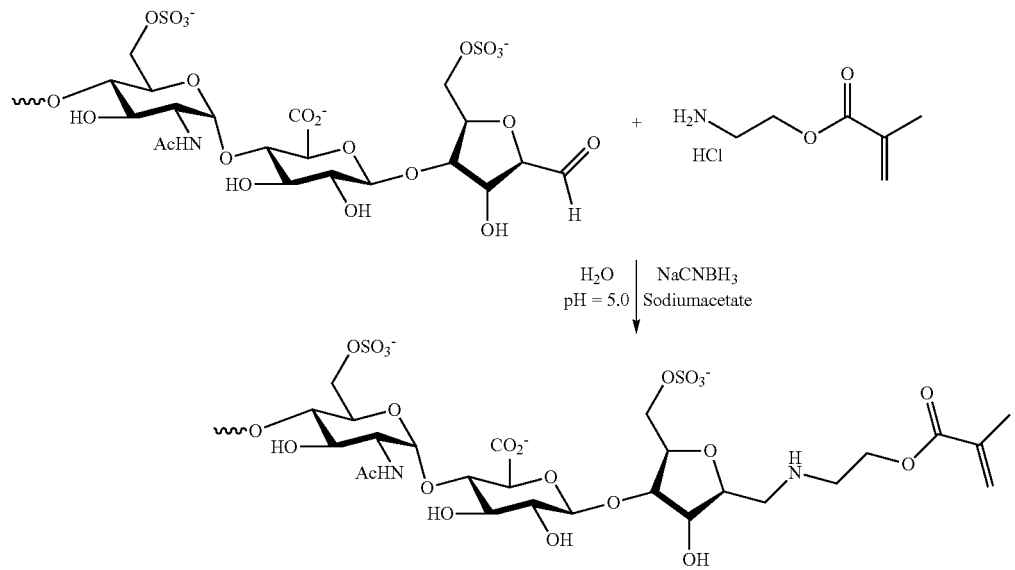

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The invention embraces all combinations of preferred and more preferred groups and suitable and more suitable groups and embodiments of groups recited above.

The invention claimed is:

1. A substrate with a surface having a hydrophilic coating comprising a cross-linked copolymer of components A and B, and optional components C and D; wherein component A comprises one or more $C_2$-$C_{16}$ hydrophilic monomers each bearing one or more alkene and/or alkyne groups;

component B comprises one or more hydrophilic polymers each bearing two or more alkene and/or alkyne groups;

component C, if present, comprises one or more beneficial agents each bearing one or more alkene or alkyne groups; and component D, if present, comprises one or more low molecular weight cross-linking agents each bearing two or more functional groups independently selected from thiol, alkene and alkyne groups;

wherein the cross-linked copolymer is formed by radical polymerisation involving the alkene and/or alkyne groups of components A, B and C (if present) and involving the functional groups of component D (if present);

wherein the hydrophilic coating optionally comprises component E which comprises one or more beneficial agents, wherein component E does not form a copolymer with components A, B, C (if present) and D (if present);

and wherein the hydrophilic coating is covalently attached to the surface of the substrate.

2. A substrate according to claim 1, wherein the covalent attachment between the surface of the substrate and the hydrophilic coating is formed via the reaction of surface-bound radicals on the surface of the substrate with a component of the hydrophilic coating, and wherein the surface bound radicals are generated via abstraction of hydrogen atoms from the surface of the substrate.

3. A substrate according to claim 1, having a first surface priming coating of polydopamine, to which the hydrophilic coating is covalently attached.

4. A substrate according to claim 1, wherein component A comprises one or more $C_2$-$C_{16}$ hydrophilic monomers each bearing one or more alkene and/or alkyne groups, and also one or more groups selected from ester, ether, carboxyl, hydroxyl, thiol, sulfonic acid, sulfate, amino, amido, phosphate, keto and aldehyde groups.

5. A substrate according to claim 4, wherein component A comprises acrylic acid and/or methacrylic acid.

6. A substrate according to claim 1, wherein component B comprises one or more hydrophilic polymers each bearing two or more alkene and/or alkyne groups, wherein the hydrophilic polymer is independently selected from the group consisting of hyaluronic acid, a hyaluronic acid derivative, poly-N-vinylpyrrolidone, a poly-N-vinylpyrrolidone derivative, a polyether derivative, polyvinylalcohol, and a polyvinylalcohol derivative.

7. A substrate according to claim 6, wherein component B comprises one or more PEG polymers each bearing two alkene groups.

8. A substrate according to claim 7 wherein component B comprises one or more diacrylate-functionalised PEG polymers.

9. A substrate according to claim 1, wherein component B comprises one or more hydrophilic polymers each bearing two or more alkene and/or alkyne groups, and wherein each hydrophilic polymer independently has molecular weight of 600-40,000 Da.

10. A substrate according to claim 1 wherein said beneficial agent of component C is an agent having pharmacological activity, a conductive agent or an adhesive agent.

11. A substrate according to claim 10, wherein the agent having pharmacological activity is an anti-thrombogenic agent, an anti-angiogenic agent, an anti-proliferative agent or an anti-microbial agent.

12. A substrate according to claim 1, wherein component D comprises one or more low molecular weight cross-linking agents each bearing two or more thiol groups.

13. A substrate according to claim 1, wherein said beneficial agent of component E is an agent having pharmacological activity, a conductive agent or an adhesive agent, wherein the agent having pharmacological activity is an anti-thrombogenic agent, an anti-angiogenic agent, an anti-proliferative agent or an anti-microbial agent.

14. A substrate according to claim 1, wherein the hydrophilic coating is lubricious and has a lubricity of <100 g, using the Lubricity Test.

15. A substrate according to claim 14, wherein the hydrophilic coating has durability of <50 g, using the Durability Test.

16. A substrate according to claim 1, wherein the substrate is a medical device.

17. A method of forming a hydrophilic coating which is covalently attached to the surface of a substrate; wherein said method comprises the steps of:

(a) contacting the surface with a mixture comprising components A and B, optional component C, optional component D and a radical initiator; wherein component A comprises one or more $C_2$-$C_{16}$ hydrophilic monomers each bearing one or more alkene and/or alkyne groups;

component B comprises one or more hydrophilic polymers each bearing two or more alkene and/or alkyne groups;

component C, if present, comprises one or more beneficial agents each bearing one or more alkene or alkyne groups; and component D, if present, comprises one or more low molecular weight cross-linking agents each bearing two or more functional groups independently selected from thiol, alkene and alkyne groups; and (b) initiating radical polymerisation involving the alkene and/or alkyne groups of components A, B and C (if present) and involving the functional groups of component D (if present) in order to form a cross-linked copolymer of component A, component B, and optional components C and D; wherein said copolymer is covalently linked to the surface; and (c) optionally incorporating into the hydrophilic coating a component E which comprises one or more beneficial agents, wherein component E does not form a copolymer with components A, B, C (if present) and D (if present).

18. A method according to claim 17, wherein the substrate is a substrate having a surface comprising abstractable hydrogen atoms.

19. A method according to claim 17, wherein component A comprises one or more $C_2$-$C_{16}$ hydrophilic monomers each bearing one or more alkene and/or alkyne groups, and also one or more groups selected from ester, ether, carboxyl, hydroxyl, thiol, sulfonic acid, sulfate, amino, amido, phosphate, keto and aldehyde groups, and wherein component B comprises one or more hydrophilic polymers each bearing two or more alkene and/or alkyne groups, wherein the hydrophilic polymer is independently selected from the group consisting of hyaluronic acid, a hyaluronic acid derivative, poly-N-vinylpyrrolidone, a poly-N-vinylpyrrolidone derivative, a polyether derivative, polyvinylalcohol, and a polyvinylalcohol derivative.

20. A substrate with a hydrophilic coating obtainable according to the method of claim 17.

21. A substrate according to claim 1, wherein the ratio of component B to component A is between 2.5:1 and 0.5:1 w/w.

22. A substrate according to claim 6, wherein the polyether derivative is polyethylene glycol (PEG), a polyethylene glycol (PEG) derivative, polypropylene glycol (PPG), or a polypropylene glycol (PPG) derivative.

23. A substrate according to claim 8, wherein the one or more diacrylate-functionalised PEG polymers are of formula (I):

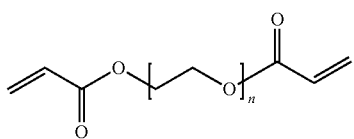

wherein n is 10-50,000 or are of formula (II):

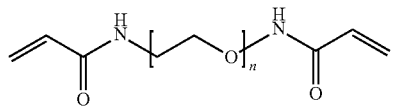

wherein n is 10-50,000.

24. A substrate according to claim 9, wherein each hydrophilic polymer independently has a molecular weight of 4,000-16,000 Da.

25. A substrate according to claim 11, wherein the agent having pharmacological activity is heparin.

26. A method according to claim 19, wherein component A comprises acrylic acid and/or methacrylic acid and component B comprises one or more PEG polymers each bearing two alkene groups.

27. A method according to claim 19, wherein the polyether derivative is polyethylene glycol (PEG), a polyethylene glycol (PEG) derivative, polypropylene glycol (PPG) or a polypropylene glycol (PPG) derivative.

* * * * *